United States Patent
Wu

(10) Patent No.: US 10,064,954 B2
(45) Date of Patent: Sep. 4, 2018

(54) POLYMER-CYCLODEXTRIN-LIPID CONJUGATES

(71) Applicant: Nian Wu, North Brunswick, NJ (US)

(72) Inventor: Nian Wu, North Brunswick, NJ (US)

( * ) Notice: Subject to any disclaimer, the term of this patent is extended or adjusted under 35 U.S.C. 154(b) by 0 days.

(21) Appl. No.: 15/184,015

(22) Filed: Jun. 16, 2016

(65) Prior Publication Data

US 2016/0375150 A1 Dec. 29, 2016

Related U.S. Application Data

(60) Provisional application No. 62/183,400, filed on Jun. 23, 2015.

(51) Int. Cl.
| | |
|---|---|
| *A61K 47/48* | (2006.01) |
| *A61K 47/60* | (2017.01) |
| *A61K 47/54* | (2017.01) |
| *A61K 47/69* | (2017.01) |

(52) U.S. Cl.
CPC ...... *A61K 47/48969* (2013.01); *A61K 47/542* (2017.08); *A61K 47/554* (2017.08); *A61K 47/60* (2017.08); *A61K 47/6951* (2017.08)

(58) Field of Classification Search
CPC .. A61K 47/6951; A61K 47/60; A61K 47/554; A61K 47/542
See application file for complete search history.

(56) References Cited

U.S. PATENT DOCUMENTS

| | | | |
|---|---|---|---|
| 8,304,565 B2 | 11/2012 | Wu et al. | |
| 8,883,177 B2 | 11/2014 | Wu | |
| 9,175,027 B2 | 11/2015 | Wu | |
| 2009/0291132 A1 | 11/2009 | Keller et al. | |
| 2010/0076209 A1 | 3/2010 | Wu et al. | |
| 2010/0210518 A1 | 8/2010 | Keller et al. | |
| 2010/0240883 A1 | 9/2010 | Wu et al. | |
| 2010/0330033 A1 | 12/2010 | Wu et al. | |
| 2011/0040113 A1 | 2/2011 | Wu et al. | |
| 2012/0202890 A1 | 8/2012 | Wu | |
| 2012/0202979 A1 | 8/2012 | Wu | |
| 2015/0064283 A1 | 3/2015 | Wu | |
| 2015/0157721 A1 | 6/2015 | Wu | |

OTHER PUBLICATIONS

Mayur, Research and Reviews: Journal of Pharmacy and Pharmaceutical Sciences, vol. 1, Issue 1, Oct.-Dec. 2012.*

* cited by examiner

*Primary Examiner* — Layla D Berry
(74) *Attorney, Agent, or Firm* — Cesari and McKenna, LLP

(57) ABSTRACT

The invention comprises compounds, methods of making, and methods of using. A group of polymer-cyclodextrin-lipid conjugates having a center backbone and three or four appended functional groups are disclosed, wherein one of the hydrophilic components is cyclodextrin. The compounds may have a backbone with three or four appended functional groups: one or two lipophilic compounds including sterols or "fat soluble" vitamins or fatty acids, one or two hydrophilic polymer and one cyclodextrin. Specific functional groups may be selected for specific applications in formulating pharmaceuticals, cosmetics, nutraceuticals, and the like. Typical coupling reaction of the conjugates may involve one or more or combinations or in series of alkylation including N-alkylation or O-alkylation, etherification, esterification and amidation chemical processes. A variety of linkers between the center backbone and functional groups may also be selected to modify the carriers or center backbones for the coupling reactions and optimize performance of the conjugates.

15 Claims, 2 Drawing Sheets

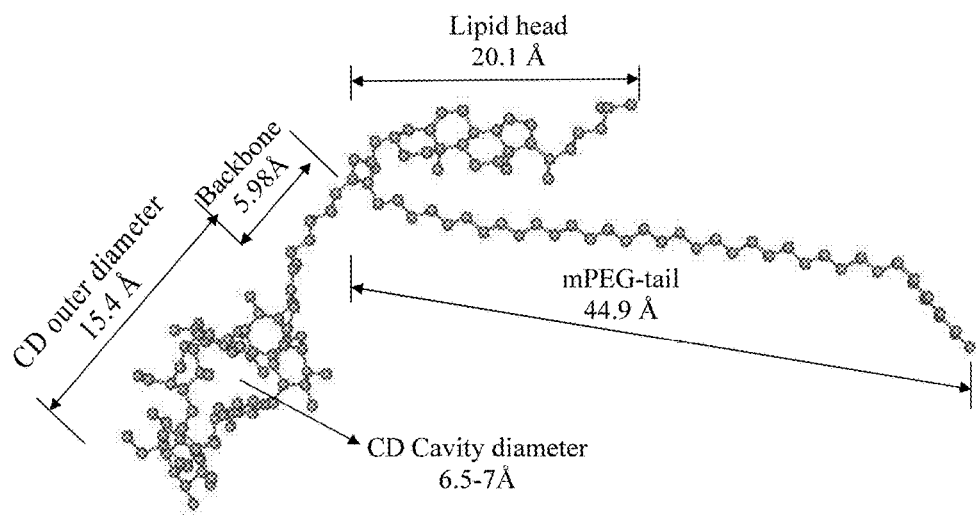
Figure 1
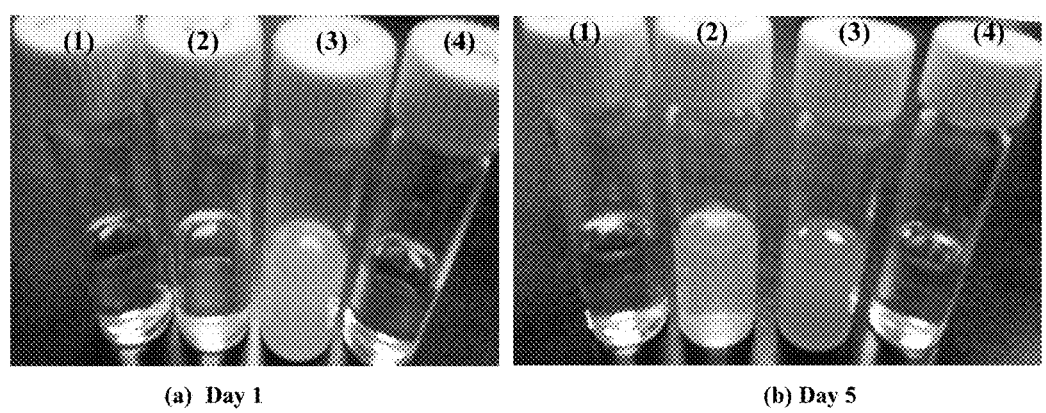
(a) Day 1
(b) Day 5
Figure 2A
Figure 2B

POLYMER-CYCLODEXTRIN-LIPID CONJUGATES

This application claims priority to the provisional patent application Ser. No. 62/183,400, entitled "Polymer-Cyclodextrin-Lipid Conjugates" filed in the U.S. Patent and Trademark Office on Jun. 23, 2015, by Nian Wu.

FIELD OF THE INVENTION

The present invention relates to polymer-cyclodextrin-lipid Conjugates, detailed and specific disclosures are given for synthetic polyethylene glycol (PEG)-cyclodextrin-lipid conjugates with fatty or sterols or so called "fat soluble" vitamins ("lipo-vitamin") as the lipophilic carriers in the conjugates and preferably having substantially monodisperse PEG chains if used for intravenous drug administration. More particularly, the present invention relates to novel polymer-cyclodextrin-lipid conjugates having cyclic oligosaccharides to replace linear oligosaccharides as for the carbohydrate component in our previous inventions. Such combination of the core characters of lipophilic solubilization wherein polymer-lipids and inclusion comlexation wherein cyclodextrins may maximize the ability of the conjugates for delivering poor water soluble therapeutic agents and reduction of toxicity in pharmaceutical products as well use for cosmetics or foods and other purposes.

BACKGROUND OF INVENTION

Polyethylene glycol (PEG) is widely used as a water soluble carrier for polymer-drug conjugates. PEG is undoubtedly the most studied and applied synthetic polymer in the biomedical field [Duncan, R. *Nature Rev. Drug Discov.* 2003, 2, 347-360]. As an uncharged, water-soluble, nontoxic, nonimmunogenic polymer, PEG is an ideal material for biomedical applications. Covalent attachment of PEG to biologically active compounds is often useful as a technique for alteration and control of biodistribution and pharmacokinetics, minimizing toxicity of these compounds [Duncan, R. and Kopecek, J., *Adv. Polym. Sci.* 57 (1984), 53-101]. PEG possesses several beneficial properties: very low toxicity [Pang, S. N. J., *J. Am. Coil. Toxicol,* 12 (1993), 429-456], excellent solubility in aqueous solutions [Powell, G. M., Handbook of Water Soluble Gums and Resins, R. L. Davidson (Ed.), Ch. 18 (1980), MGraw-Hill, New York], and extremely low immunogenicity and antigenicity [Dreborg, S, *Crit. Rev. Ther. Drug Carrier Syst.,* 6 (1990), 315-365]. The polymer is known to be non-biodegradable, yet it is readily excretable after administration into living organisms. In vitro study showed that its presence in aqueous solutions has shown no deleterious effect on protein conformation or activities of enzymes. PEG also exhibits excellent pharmacokinetic and biodistribution behavior. [Yamaoka, T., Tabata, Y. and Ikada, Y., *J. Pharm. Sci.* 83 (1994), 601-606].

Over last three decades, some of promising drug carriers that have been investigated in systemic delivery systems includes liposomes, polymeric nanoparticles, polymeric micelles, ceramic nanoparticles and dendrimers (Cherian et al. *Drug Dev. Ind Pharm,* 26: (2000) 459-463; Lian and Ho. *J. Pharm. Sci,* 90 (2001) 667-680; Adams et al. *Pharm. Sci.* 92 (2003) 1343-1355 Na et al. *Eur. J. Med. Chem.* 41 (2006) 670-674; Kaur et al. *J. Control. Rel,* 127(2008) 97-109). Systemic drug delivery may be achieved by intravenous or intraperipheral injection and therefore is non-invasive. The drugs may be administered repeatedly as needed. However, in order to achieve therapeutic concentrations at the target site, systemic administration requires large dosages with relatively high vehicle contents which may cause side effects such as allergic reactions ["Cremophor-based paclitaxel 'chemo' drug triggers fatal allergic reactions," *The Medical News.* 9 Jun. 2009].

In the design of safe and biocompatible delivery systems, several important factors may be taken into account including high solubilization properties and retaining power of the carrier and appropriate surface characteristics to permit interactions with potential targeting tissue sites or cell membrane permeations.

Cyclodextrins (CDs) are cyclic oligosaccharides (Chemical Structure 1) that have been studied for several decades and as one of the leading pharmaceutical excipients approved by the US FDA (Food and Drug administration) for dozens of marketed pharmaceutical products, they are continued being utilized as an important vehicle for poor water soluble agents. Unlike polymer excipients, CDs are biological active and their solubilizing ability achieved through forming water-soluble complexes with many hydrophobic agents.

Chemical Structure 1: 6 (α), 7 (β) and 8 (γ) member rings of cyclodextrins used in the present invention

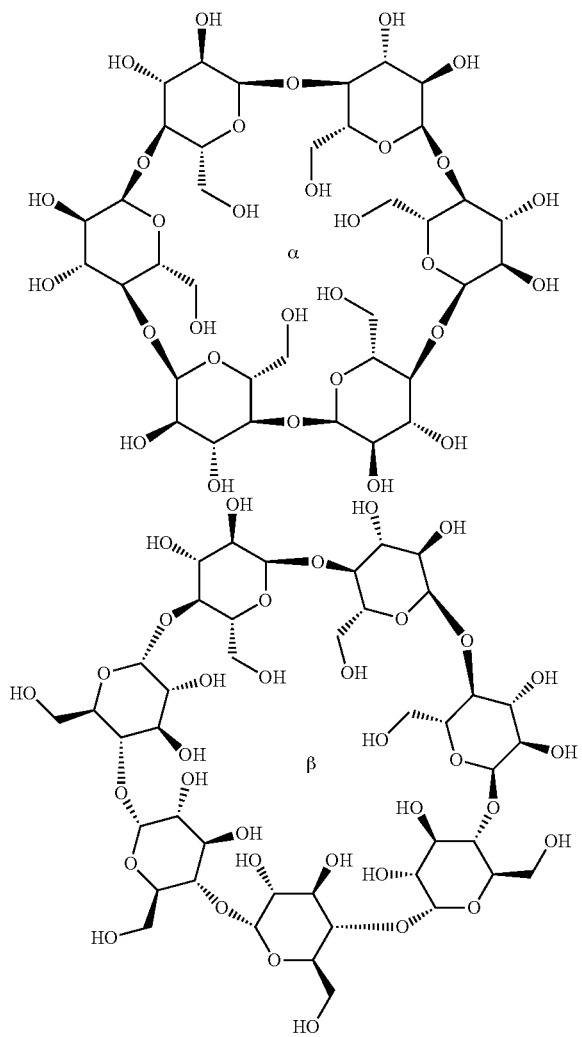

-continued

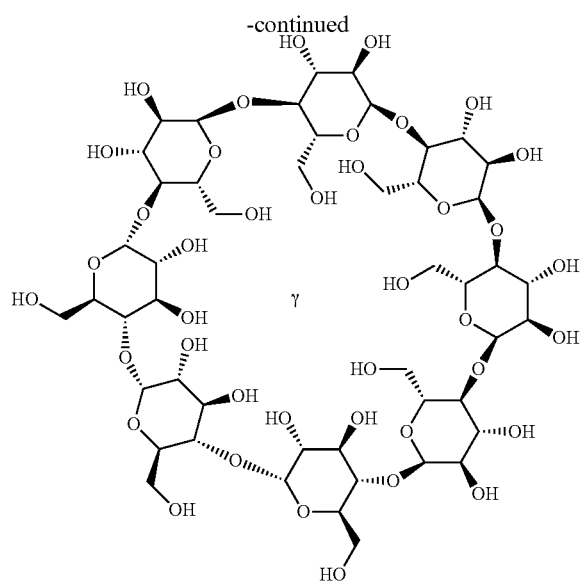

γ

Lipids are a group of naturally occurring molecules including fatty acids, sterols and fat-soluble vitamins (vitamin A, D and E), monoglycerides, diglycerides, triglycerides, phospholipids, and others. The main biological functions of lipids include storing energy, signaling, and acting as structural components of cell membranes [Fahy E, Subramaniam S, Brown H A, et al. (2005). "A comprehensive classification system for lipids". *J. Lipid Res.* 46 (5): 839-61]. The lipid classification scheme is chemically based and driven by the distinct hydrophobic and hydrophilic elements that compose the lipid. Lipids such as sterols and related compounds play essential roles in the physiology of eukaryotic organisms are a subgroup of the steroids. They occur naturally in plants, animals, and fungi, the most familiar type of animal sterol is cholesterol. Cholesterol is vital to animal cell membrane structure and function and forms part of the cellular membrane in animals, where it affects the cell membrane's fluidity and serves as secondary messenger in developmental signaling [Alberts B, Johnson A, Lewis J, Raff M, Roberts K, and Walter P (2002). *Molecular biology of the cell.* 4$^{th}$ Edition, New York: Garland Science. p. 1874].

The present invention compromises one of the three carrier groups consisting of a lipid including but not limited to fatty acids, sterols including but not limited to cholesterol, stigmasterol, ergosterol, hopanoids, phytosterol, sitosterol, campesterol, brassicasterol, avenasterol adosterol, and stanols (saturated steroid alcohols or hydrogenated sterols). Sterols are biological importance as a highly compatible vehicle for drug delivery, for instance cholesterol makes up about 10-50 percent of the total lipid in natural cell membranes, the conjugates containing sterols or fat soluble vitamins may increase the drug permeation for cell targeted delivering.

The human body has a natural tendency to maintain homeostasis, and may be elaborated from substances present in the diet, sometimes exclusively, for vitamins, minerals, essential amino-acids and essential fatty acids including polyunsaturated fatty acids which play a significant role in the prevention of cardiovascular disease in human. Vitamin E is the general term for all tocopherols and tocotrienols, of which alpha-tocopherol is the natural and biologically most active form. The antioxidant function of vitamin E is considered to be critical for the prevention of oxidation of tissue. While these molecules are essential for the human body, they may be utilized as safer ingredients to design for an ideal carbohydrate-lipid conjugate.

The present invention compromises one of the three carrier groups consisting of a sterol or fat soluble vitamin. Another carrier group is a cyclodextrins containing a number of glucose monomers ranging from six to eight units in a ring. The third carrier is a water soluble polymer such as polyethylene glycol. The three carrier groups are attached covalently to a center backbone where at least three bonding positions or sites available. The conjugation may be achieved via one or more types of reactions or combination of alkylation including N-alkylation or O-alkylation, etherification, esterification and amidation.

The solubility of organic molecules is often summarized by the phrase, "like dissolves like." This means that molecules with many polar groups are more soluble in polar solvents, and molecules with few or no polar groups (i.e., nonpolar molecules) are more soluble in nonpolar solvents (R. Casiday and R. Frey, "Maintaining the Body's Chemistry: Dialysis in the Kidneys," http://www.chemistry.wustl.edu/~edudev/LabTutorials/Dialysis/Kidneys.html, Department of Chemistry, Washington University, St. Louis, Mo., accessed on Dec. 3, 2013).

Vitamins are either water-soluble or fat-soluble (soluble in lipids and nonpolar compounds), depending on their molecular structures. Water-soluble vitamins have many polar groups and are hence soluble in polar solvents such as water. In contrast fat-soluble vitamins are predominantly nonpolar and hence are soluble in nonpolar solvents such as the fatty (nonpolar) tissue of the body.

Solubility is a complex phenomenon that depends on the change in free energy ($\Delta G$) of the process. For a process, i.e., a vitamin dissolving in a solvent, to be spontaneous, the change in free energy may be negative (i.e., $\Delta G<0$) [M. Traverso, "Vitamin Solubility," http://www.chemistry.wustl.edu/~edudev/LabTutorials/CourseTutorials/Tutorials/Vitamins/molecularbasis.htm, Washington University, St. Louis, Mo., accessed on Dec. 3, 2013].

Narrow molecular weight distribution of drug delivery polymers is crucially important for biomedical applications, especially if used for intravenous injections. For instance, PEG-8 Caprylic/Capric Glycerides are mixtures of monoesters, diesters, and triesters of glycerol and monoesters and diesters of polyethylene glycols with a mean relative molecular weight between 200 and 400. Partially due to allergic reactions observed in animals, the application of PEG-8 CCG for paranteral administration of many water-insoluble drugs is restricted and hence is limited usable for human drug formulations.

BRIEF SUMMARY OF THE INVENTION

The present invention comprises compounds having a polymer-lipid conjugate comprising a backbone and three or four appended functional groups as showed in FIG. 1: one or two lipophilic vitamins or sterols or alike, one or two hydrophilic polymers, the polymer-lipid conjugates are then further attached to a cyclodextrin, the number of polymer-lipid conjugates attached to the cyclodextrin may be dependent on the available primary hydroxyl groups. As showed in the Chemical Structure 2, the primary hydroxyl groups on the C-6 (denoted by an open arrow) have the highest reactivity, especially when bulky substitution reagents are used, and the secondary hydroxyl groups on C-2 and C-3 (denoted by a solid arrow) have least reactivity. This is attributed to the hydrogen bonding between the protons of the hydroxyl group on C-3 and the oxygen atom of the hydroxyl group on the C-2, a hydrogen bond with the C-3 hydroxyl group of the neighboring glucopyranose unit [F. M. Menger and M. A. Dulany (1985). *Tetrahedron Lett.* 26: 267]. The C-2 hydroxyl group of one glucopyranose unit can form a hydrogen bond with the C-3 hydroxyl group of the neighboring glucopyranose unit [B. Gillet, D. J. Nicole and J. J. Delpuech, *Tetrahedron Lett.*, 1982, 23, 65] and hydrogen-deuterium exchange in the secondary hydroxyl groups of α-cyclodextrin, β-cyclodextrin and γ-cyclodextrin showed that the strongest hydrogen bond system is formed in the β-cyclodextrin [B. Casu, G. G. Gallo, M. Reggiani and A. Vigevani, J. Chem. Soc. Spec. publ., 1968, 23, 217]. While a complete secondary belt is formed by these hydrogen bonds in β-cyclodextrin, thus making it a rigid structure and the hydrogen ring is incomplete in the α-cyclodextrin because one of the glucopyranose units is in a distorted position and only four can be formed instead of the six possible hydrogen bonds [D. A. Rees, J. Chem. Soc. (B), 1970, 877; B. P. Schonberger, A. C. A. Jansen and L. H. M. Janssen, in 'Proceedings of the 4th International Symposium on Cyclodextrins, Munich, 1988', eds. O. Huber and J. Szejtli, Kluwer, Dordrecht, 1988, p. 61]. In the Chemical Structure 2, (a) and (b) symbolize the same basic structure of cyclodextrins and "n" represents a number of glucopyranose units with the truncated circle line in (a). However only (b) will be used in the specification to simplify the drawings and to express the cyclodextrin molecular structures entirely.

Chemical Stucture 2: Potential reactive hydroxyl sites in cyclodextrins

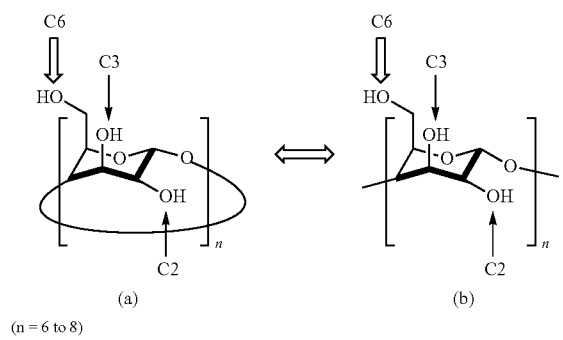

(n = 6 to 8)

In one aspect of the present invention, while multiple polymer-lipid substitutants to a cyclodextrin may be possible as showed in the General Structure 1, a few substitutants of cyclodextrin may be preferable. The most popular common method for a monomodification at 6-position of cyclodextrin is so called nucleophilic substitution of a reagent containing appropriate group on mono-6-tosyl cyclodextrin or mono-6-mesosyl cyclodextrin. The monotosylated cyclodextrin derivatives are synthesized by reacting molar equivalent of benzene or p-toluene-sulfonyl chloride with cyclodextrin in pyridine or DMF containing a base [R. C. Petter, J. S. Salek, C. T. Sikorsky, G. Kumaravel and F. T. Lin, *J. Am. Chem. Soc.*, 1990, 112, 3860; X. M. Gao, L. H. Tong, Y. Inoue, and A. Tai, *Synth. Commun.*, 1995, 25, 703; K. A. Martin and A. W. Czarnik, *Tetrahedron Lett.*, 1994, 35, 6781]. The monosubstituted 6-tosylcyclodextrins and mono-6-mesosylcyclodextrins are important precursors for a variety of modified cyclodextrins. A nucleophilic displacement of the tosyl or mesoyl group by suitable nuleophiles such as iodide, azide, thioacetate, alkyl, hydroxylamine or polyalkylamines yields monoiodo-, azido-, thio-, hydroxylamino-, or alkylamino-cyclodextrins [L. E. Fikes, D. T. Winn, R. W. Sweger, M. P. Johnson and A. W. Crarnik, *J. Am. Chem. Soc.*, 1992, 114, 1493; A. Ueno, F. Moriwaki, T. Osa, F. Hamada and K. Murai, *Tetrahedron*, 1987, 43, 1571; K. Tsujihara, H. Kurita and M. Kawazu (1977). *Bull. Chem. Soc. Jpn.*, 50, 1567; D. W. Griffiths and M. L. Bender, *Adv. Catal.*, 1973, 54, 625; B. Siegel (1979). *J. Inorg. Nucl. Chem.* 41, 609]. Further purification may be achieved by recycystallation in a mixture of methanol and water [M. Popr (2014). *Beilstein J. Org. Chem.*, 10, 1390-1396].

General Structure 1

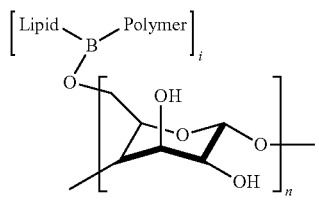

Where "n" is a number of the glucopyranose rings of cyclodextrins ranging from 6 to 8 and "i" is the averaged number of substituents (molar degree of substitution) of PEG-lipid per glucopyranose repeat unit ranging from 0.5 to 3. Specific polymer or liphophilic groups may be selected for specific applications in formulating pharmaceuticals, cosmetics, nutraceuticals, and the like. A variety of linkers between the backbone and functional groups may also be selected to optimize performance. The coupling reaction is one or combination or series of alkylation, esterification, etherification and amidation chemical process.

BRIEF DESCRIPTION OF THE FIGURES

FIG. 1 shows a representation of PEG-β-cyclodextrin-cholesteryl-diaminopropane in the present invention as the sample polymer-cyclodextrin-lipid conjugate. The lengths of each partions of the conjugate are estamated by ChemBioDraw® Ultra 10 (CambridgeSoft, Waltham, Miss., USA)

FIG. 2A shows the solubility comparison of 1% propofol in (1) 3.5% of Cholesteryl-lactobionate-mPEG12; (2) 35% of 2-Hydroxypropyl-β-CD; (3) a mixture of 2% Cholesteryl-lactobionate-mPEG12 and 15% 2-Hydroxypropyl-β-CD and (4) 2% of mPEG$_{12}$-β-cyclodextrin-cholesterol and FIG. 2B shows the same sample solutions at day 5.

DETAILED DESCRIPTION OF PREFERRED EMBODIMENTS

Figure 3:
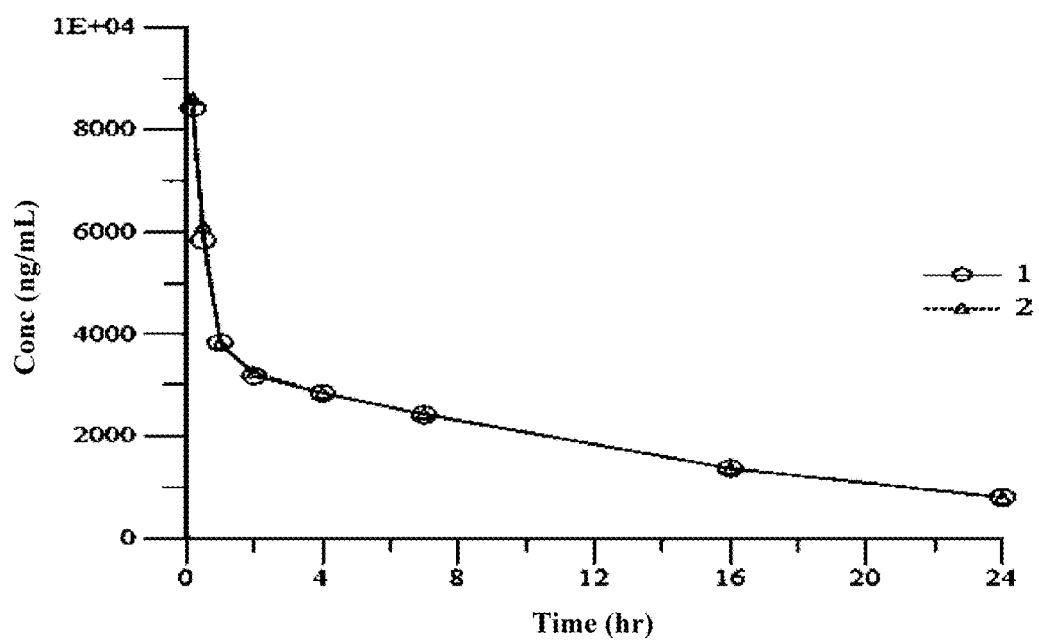
FIG. 3 shows pharmacokinetic profiles of voriconazole formulations with (1) a commercial product of voriconazole, 10 mg/mL and (2) a sample formula consisting of 10 mg voriconazone/mL in a solution of 3% PEG-β-cyclodextrin-cholesterol conjugate.

Embodiments of the present invention are described herein in the context of varying polymer-cyclodextrin-lipid conjugates for drug delivery. Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementation of the present invention.

In the interest of clarity, not all of the routine features of the implementations herein are described. It will be appreciated that in the development of such actual implementation, numerous implementation-specific details may need to be made in order to achieve the developer's specific goals, and that these specific goals may vary.

United States Patent Publication 20150157721 and 20120202890, which are hereby incorporated by reference, teach the aqueous formulations of poor water soluble agents by employing certain polymer-carbohydrate-lipid (PCL) conjugates. The patents described how to prepare the polymer-carbohydrate-lipid conjugates and its applications by simply adding the conjugate to an aqueous solution. It has been demonstrated that PCLs are useful for solubilizing hydrophobic drugs without the formation of liposomes or microemulsions.

Differentiating from the previous inventions published in US20150157721 and US20120202890, the present invention comprises the cyclic oligosaccharide portion of the polymer-cyclodextrin-lipid conjugates while those conjugates remains a basic structure having a backbone and three or four appended functional groups: one or two lipophilic vitamins or sterols or fatty acids, one or two hydrophilic polymers. The chemical and physical characters of cyclic oligosaccharides are significantly different from the linear oligosaccharides that were utilized in the previous invention. While poor water soluble agents may be solubilized by forming inclusion complexes with the cyclodextrin portion of the conjugates, the hydrophobic compounds may be also solubilzed by either encapsulation or microemulsion with the PEG-lipid portion of the conjugate. By combining these two functionalities of inclusion and encapsulation or microemulsion all into one compound, it is possible to achieve improved formulations of many active (pharmaceutical) agents. The general structure of the family of compounds is shown as General Structure 1, where "B" indicates the backbone, "PEG" indicates the polymer, "Lipid" indicates lipophilic vitamin or sterol or fatty acid. In aqueous solutions, the new conjugates act as a solubility enhancer of poor water soluble agents resulting in either a true solution or a very stable emulsified suspension with those of active agents. Where the cyclodextrin has 6 or 7 or 8 member rings, the degree of substitution of the cyclic oligosaccharides may be from 0.5 to 3.

Another differentiation from our previous inventions published in US20150157721 and US20120202890, the present invention comprises cyclodextrins [Brigandi, R A., et al (2014). Clinical Pharm in Drug Dev. 4(2), 130-136] may reduce the hemolytic effects of fatty acids alone similar to sterols or sterol-like compounds that may also significantly reduce potential hemolytic activity induced by fatty acids [Mimura, T. "Fatty acids and sterols of the tunicate, Salpa thompsoni, from the Antarctic Ocean: chemical composition and hemolytic activity". Chemical & pharmaceutical bulletin, 34 (1986) 4562]. Unlike sterols, water soluble steroid acids (bile acids) are more likely inducing hemolytic anemia [Ilani, A. "The pH dependence of the hemolytic potency of bile salts". Biochimica et biophysica acta, 1027 (1990) 199]. For this particular reason, nonwater soluble sterols are preferable to be selected as the primary lipophilic carrier in the conjugates. In case there are two lipophilic carriers, one may be cholesterol or a non-hemolytic sterol or "fat soluble" vitamin.

In one aspect of the present invention, the present invention comprises cyclodextrins to significantly reduce potential hemolytic activity of fatty acids as compared to commercial available PEG-lipids including polyethylene glycol sorbites, polyoxyethylated castor oil (Cremophor) and mono/diglycerides of caprylic/capric acid in glycerol (Capmul®) polyglycolized glycerides (Labrafac®), PEG-6 glyceryl monoleate or PEG-6 glyceryl linoleate (Labrafil®), PEG-8 glyceryl caprylate/caprate (Labrasol®). While these fatty acid based lipid-polymers may increase poor water soluble agents, hemolysis is induced at higher lipid-drug ratios [G. D. Noudeh, P. Khazaeli and P. Rahmani. "Study of the Effects of Polyethylene Glycol Sorbitan Esters Surfactants Group on Biological Membranes." International Journal of Pharmacology, 4 (2008) 27-33; A. O. Nornooa, D. W. Osborneb, D. S. L. Chow (2008). "Cremophor-free intravenous microemulsions for paclitaxel: I: Formulation, cytotoxicity and hemolysis." International Journal of Pharmaceutics. 349, 108-116].

Further differentiation from our previous inventions published in US 20150157721 and US20120202890, the present invention comprises large a cyclic oligosaccharide ringe which are a rigid component in the conjugate construction, not having the same freedom of movement that the linear oligosaccharide based conjugates possess. This creates two different spaces in the conjugates, if adjacent polymer-lipid substitutant of cyclodextrin is i.e., PEG-cholesterol, both "spaces" are rigid. If the polymer-lipid is PEG-oleate, than the second phase is more flexible than cyclodextrin. As showed in FIG. 1, the size of a cyclodextrin is about one third (⅓) of the PEG-lipid substituent which provides an easy access for a solute "walking" between the two spaces. It is especially useful to have a two-phase/space structure in a single conjugate; there may be two concided solubilizing processes, inclusion comlexation of cyclodextrin based on a "host-quest" mechanism and microencapsulation of PEG-lipids based on a micellar solubilization. While the two processes are physically different, the unique combination would result in enhanced solubility than those of single phases since the complexation efficiency (CE) of "host" molecules is very limited due to the cage capacity of cyclodextrins; ideally the solubility of a drug in the presence of cyclodextrins can be achieved by a 1:1 inclusion complexation. It is important to recognize that aqueous solubility enhancement by cyclodextrins is limited, often required much higher concentrations or molar/molar ratio of a cyclodextrin to solubilize a hydrophobic agent (Table 1). Conjugating polymer-lipids into cyclodextrins compensate or provide additional solubilization power to the "host" molecules.

TABLE 1

Solubility of marketed Drug Products

| Drug | LogP[1] | Dose (mg) | Drug (Mw) | CD | CD (Mw) | CD/D (w/w) | CD/D (mol/mol) |
|---|---|---|---|---|---|---|---|
| Itraconazole | 7.31 | 10 | 705.6 | hydroxypropyl-β-cyclodextrin | 1396 | 40[2] | 20.2 |
| Voriconazole | 1.82 | 200 | 349.3 | sulfobutyl ether β-cyclodextrin | 2242 | 16[2] | 2.5 |
| Telavancin HCl | 6.91 | 250 | 1755.6 | hydroxypropyl-β-cyclodextrin | 1396 | 10[2] | 12.6 |
| Carfilzomib | 4.20 | 60 | 719.9 | sulfobutyl ether β-cyclodextrin | 2242 | 50[2] | 16.1 |
| Posaconazole | 5.41 | 200 | 700.8 | sulfobutyl ether β-cyclodextrin | 2242 | 22[3] | 6.9 |
| Alphaxalone | 3.06 | 10 | 332.5 | sulfobutyl ether β-cyclodextrin | 2242 | 14[4] | 2.1 |

TABLE 1-continued

Solubility of marketed Drug Products

| Drug | LogP[1] | Dose (mg) | Drug (Mw) | CD | CD (Mw) | CD/D (w/w) | CD/D (mol/mol) |
|---|---|---|---|---|---|---|---|
| Diazepam | 3.08 | 5 | 284.7 | hydroxypropyl-β-cyclodextrin | 1396 | 90[5] | 18.4 |
| Haloperidol | 3.66 | 0.4 | 375.9 | hydroxypropyl-β-cyclodextrin | 1396 | 1125[5] | 302.9 |
| Methotrexate | −0.24 | 8 | 454.4 | hydroxypropyl-β-cyclodextrin | 1396 | 56[5] | 18.3 |
| Propranolol | 2.58 | 8 | 259.3 | hydroxypropyl-β-cyclodextrin | 1396 | 56[5] | 10.4 |
| Ranitidine HCl | 0/99 | 7 | 314.4 | hydroxypropyl-β-cyclodextrin | 1396 | 64[5] | 14.5 |

[1] logarithm of partition coefficient = a measure of lipophilicity or hydrophobicity
[2] http://www.rxlist.com
[3] http://aac.asm.org/content/early/2014/04/08/AAC.02686-13.full.pdf
[4] http://www.jurox.com
[5] http://www.sigmaaldrich.com/life-science/cell-culture/learning-center/cyclodextrin.html Unlike other known linear cyclodextrin derivatives or copolymers [Y. Ping, et al (2011) Biomaterials. 32(32): 8328-8341; ME. Davis et al. U.S. Pat. No. 7,091,192], the polymer-CD-lipid conjugates in the present invention discloses a novel molecule(s) with two apolar centers or cores wherein hydrophophic interactions between the polymer-CD-lipid conjugate and a lipophilic solute may be largely increased, thus the water solubility of the solute may be significantly enhanced. For those of cyclodextrin derivatives such as CD sulfoalkyl ether or hydroxypropyl-CD and CD copolymers, increasing compositions or the polymer sizes may only increase the water solubility themselves, not a hydrophobic interaction to a solute. While a co-polymer may change cyclodextrin complexity efficiency, the "host-guest" solubilization process underneath may be remained the same in contrast to the polymer-CD-lipid conjugates in the present invention, wherein a different microencapsulation process is introduced into or combined with the "host-guest" solubilization process.

In one aspect, the present invention significantly improved the solubilizing power of cyclodextrins. In aqueous solutions, cyclodextrins form complexes with many drugs through a process in which water molecules located in the center cavity are replaced by either the whole drug molecule or more frequently, by some lipophilic portion of the drug. The hydrophobic effect which involves breakdown and removal of the structured water molecules inside CD cavity and around the non-polar substrate. The drug-cyclodextrin complex formation is a dynamic equilibrium with free drug and cyclodextrin [R. Arun, et al (2008). Scientia Pharmaceutica. 76(4), 567-598; M. E. Brewster and T. Loftsson (2007). Advanced Drug Delivery Review. 59(7): 645-666; M. Jug and M. B. Lacan (2008). Rad. Medical Sciences, 32(499), 9-26]. The CE of cyclodextrin is also largely influenced by the molecule shape of a solute in additional to its hydrophobicity as showed in the Tale 1. Hydrophobicity may be estimated by the oil/water phase partition coefficient (Log P). In the Table 1, where the Log Ps were calculated with a computer program of Marvin Sketch (ChemAxon Kft, Budapest, Hungary). A positive value indicates more oil soluble and a negative value indicates more water soluble. Thus the stability of CD complexation is built on a temporal physical entrapment which may explain why high concentrations (or molar ratio) of CD typically required in the solubilization process, a simple 1/1 or 2/1 (CD/drug) complexation may not be sufficient to retain the solute in an aqueous environment. Thus a PEG-lipid substituent is included (through the center backbone) to enhance the stability of CDs by providing a more lipophilic core and the conjugate encapsulated with a drug then will be fully soluble in water at room temperature.

In one aspect of the present invention, the binding positions to the CD with the PEG-lipid substituent may not be considered as critical and positional isomers may be produced during synthesis of the polymer-CD-lipid conjugates, while such isomers may be functionally equivalent. The choice of isomer may have implications in a variety of delivery process such as intracellular transport of lipophilic molecules as well as their use as vehicles in pharmaceutical applications. For example, isomers may differ in the ability to stabilize a compound during solubilizing and storage.

While cyclodextrins (CDs) can enhance the drug bioavailability. For the solute with a large Log P value, much high concentration of cyclodextrin is required as showed in the Table 1. As compared to polymer-CD-lipid conjugates, even though CDs have a very large negative Log P values (Table 2), their solubility enhancement in water is weak which may be mainly due to lack of lipophilicity. In forming the inclusion complex, the physicochemical and biological properties of the drug may be also altered to affect its therapeutic functions. When a high concentration of CDs is required to improve aqueous solubility of drugs and the metabolism and pharmacokinetics of those drugs may be altered. The renal toxicity of α-CD and β-CD for parenteral administration was found in animal model [Frank D W, et al (1976). Cyclodextrin nephrosis in the rat. Am J Pathol 83:367-82] as well as problems with a number of modified CDs have been well documented [Irie T, et al (1997). J Pharm Sci. 86:147-62; Thompson D O (1997). Crit Rev Ther Drug Carrier Syst. 14:1-104; Gould S, et al (2005). Food Chem Toxicol. 43:1451-9]. In addition, as severe renal impairment prolongs the elimination rate of cyclodextrin with high CD contents.

In one aspect of the present invention, the hydrophobic interaction may be increased significantly by incorporating a CD group into the polymer-lipid conjugates. The water solubility is enhanced for those hydrophobes where the encapsulation of the lipophilic molecules into the cage-hydrophobic core of the conjugates is improved. Differentiated from previous described lipid-(linear) carbohydrate-polymer conjugates, the current invention presents a double-functional enhancer having stronger hydrophobic interactions with lipophilic solutes. The same hydrophobic interaction may not be achieved with CD alone due to the poor lipophilic character (Table 2) or PEG-linear carbohydrate-lipid alone due to the two solubilizing processes may compensate each other. The polymer-lipid substitutants of CDs support noninclusion-based drug solubilization such as micelle-like effects and molecular aggregation.

In one aspect of the present invention comprise CD molecules with polymer-lipids available for equilibrium of a solute between the apolar cavity of a CD and the hydrophobic core of lipids instead of the equilibrium between the apolar cavities of a CD or the hydrophobic core of PEG-lipids and aqueous phase. The latter may result in a precipitation.

In watery-aqueous environment, the interior of polymer-lipid conjugates or the cavity of CDs is largely non-polar and the principle to use when determining hydrocarbon solubility is "like dissolves like." In additional caged complexation, noninclusion interaction between CDs or polymer-lipids and lipophilic solutes are clumped together "like dissolves like." On the outside of the polymer-lipids or CDs are largely polar groups which are able to interact with the polar water molecule, thus the entire polymer-cyclodextrin-lipid conjugate incorporating a lipophilic solute is then water soluble.

In the novel polymer-CD-lipid conjugates having two apolar inner sites and outer sites with abounding hydroxyls and expendable polymer chains are good solubility enhancers. They may aid in the formation of stable solution or emulsions or blends of water and lipophilic agents. These conjugates provide an extended center apolar core which stabilizes hydrophobic molecules in water by maximizing the retaining power and reducing the interface energy at the liquid-liquid interface.

The hydrophobic interaction is defined as an entropic effect generating from the disruption of highly dynamic hydrogen bonds between molecules of liquid water by the hydrophobic solute [T. P. Silverstein, "The Real Reason Why Oil and Water Don't Mix". *Journal of Chemical Education.* 75(1998) 116-346]. When a hydrophobic solute is mixed in an aqueous medium, hydrogen bonds between water molecules will be broken to make room for the hydrophobic solute; since water molecules do not react with the hydrophobic solute. Such hydrophobic effect may be quantified by measuring the partition coefficients of non-polar molecules between water and non-polar solvents. The partition coefficients may be transformed to free energy ($\Delta G$) of transfer which includes enthalpy ($\Delta H$) and entropic ($\Delta S$) components. The hydrophobic effect has been found to be entropy ($\Delta S$)-driven at room temperature because of the reduced mobility of water molecules in solvation shell of the non-polar solute. The change in enthalpy ($\Delta H$) of the system may be zero, negative or positive because the formation of the new hydrogen bonds may partially, completely, or over compensate for the hydrogen bonds broken by the entrance of the hydrophobic solute. The change in enthalpy, however, may be insignificant in determining the spontaneity of mixing hydrophobic molecules and water because the change in entropy ($\Delta S$) is very large. According to the Gibbs free energy Equation, $\Delta G = \Delta H - T \Delta S$, with a small unknown value of $\Delta H$ and a large negative value of $\Delta S$, the value of $\Delta G$ will turn out to be positive. A positive $\Delta G$ indicates that the mixing of the hydrophobe and water molecules is not spontaneous which results in a phase separation or precipitation.

In another aspect of the current invention, the hydrophilic-lipophilic interaction is well balanced with the polymer-CD-lipid conjugates [Griffin W C. "Calculation of HLB Values of Non-Ionic Surfactants," *Journal of the Society of Cosmetic Chemists.* 5 (1954) 259]. For example, hydrophilic-lipophilic balance number remains greater than 15 due to the large polar portion in the conjugates to form translucent microemulsions spontaneously (Table 2). Unlike microemulsions formed by a mixture of surfactants or lipid polymers, co-surfactants and/or co-solvents which a surfactant or lipid polymer concentration is several times higher that significantly exceeds the concentration of the dispersed phase or mechanically produced translucent microemulsions which specialized equipment is required, as showed in Table 2, the polymer-CD-lipid conjugates in the present invention have optimized log P values which are able to form transparent solution or nanoemulsions spontaneously by a single polymer-CD-lipid conjugate and typically without co-solvent and external high energy input [Mason T G, Wilking J N, Meleson K, Chang C B, Graves S M. "Nanoemulsions: formation, structure, and physical properties", *Journal of Physics: Condensed Matter,* 18 (2006) R635-R666].

TABLE 2

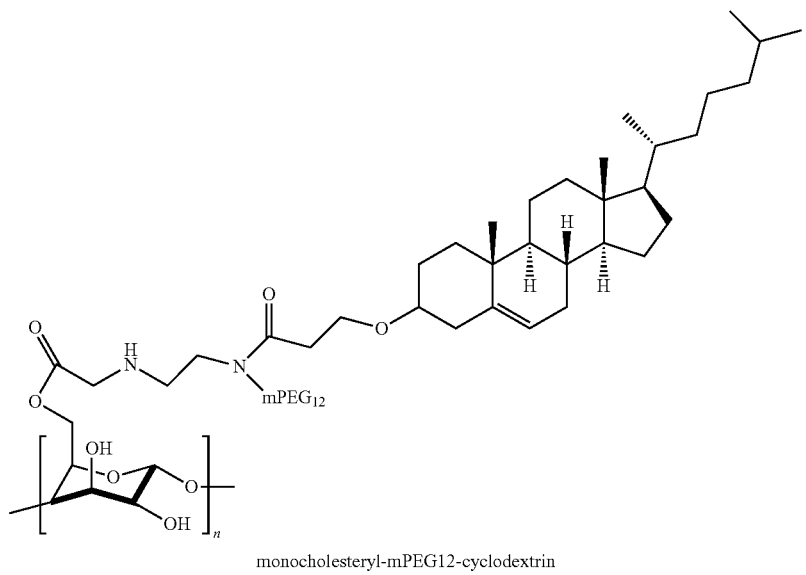

monocholesteryl-mPEG12-cyclodextrin

| CD | Molecular weight | HLB | LogP | |
| --- | --- | --- | --- | --- |
| | | | CD only | Conjugate |
| N = 6, α-CD | 2099.1 | 15.6 | −10.63 | −4.17 |
| N = 7, β-CD | 2275.2 | 16.0 | −12.40 | −4.35 |
| N = 8, γ-CD | 2423.2 | 16.3 | −14.17 | −6.06 |

In one aspect of the current invention, a stable aqueous solution may be formed with smaller polymer-CD-lipid conjugates. This is superior over conventional CDs or CD derivatives or surfactants or other lipid-polymers since many undesirable side effects caused by CDs or surfactants or lipid-polymers, higher concentrations of CDs or CD derivatives are disadvantageous or prohibitive in many applications. In addition, the stability of a microemulsion or mechanically formed nanoemulsion by surfactants or CDs is often easily compromised by dilution, by heating, or by changing pH levels. As showed in FIG. 2, simply mixing a PEG-carbohydrate-lipid conjugate (cholestoryllactobionate-mPEG-12) and HP-β-CD (2-hydroxypropyl-β-cyclodextrin) will only product an opaque emulsion. Thus a chemical conjugation is necessary in order to achieve the solubility enhancement instead of physical mixing of a CD with a PEG-lipid.

Though it is possible to use a variety of hydrophilic polymers in practicing the invention, polyethylene glycol (PEG) is preferred because of its long history of effectiveness and its status of being generally regarded as safe (GRAS). Incorporating PEG, the General Structure 2 of the new polymer-CD-lipid conjugate is:

General Structure 2

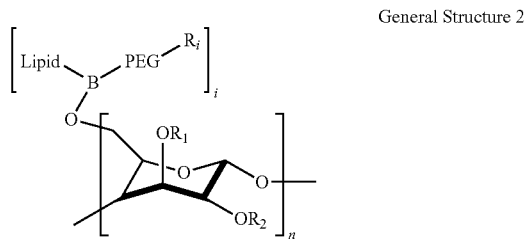

In General Structure 2, where "i" is a number of substituent comprising polymer and lipid that are conjugated to CDs through the center backbone, "i" may be equal to the available hydroxyl groups of a CD, it is preferable ranging from 1 to 7 and more preferable ranging from 1 to 5, most preferable ranging from 1 to 3. Where $R_1$ and $R_2$ may be the same or different, R1 and R2 may be hydrogen or carboxyl or alkyl ether including but not limited to —$CH_2CHOHCH_3$ or —$(CH_2)_4SO_3$—$Na^+$ or —$CH_3$. The backbone, "B" may be selected from a compound comprises at least three available binding positions or sites for the conjugation of a first carrier, a second carrier and a third carrier, each available binding position or site comprising an expendable amino, hydroxyl, or carboxylic group. The backbone may be selected from the group consisting of glycerol or glycerol-like analogues, polyamines, diamines, triamines, tetramines, aminodiol, aminotriols, aminoalcohols and amino acids having three available binding positions or sites, triols, tetraols, erythritol, triacids, tetracid, tetraacetic acid, glucoheptonic acid, and tartaric acid, including but not limited to ethanediamine, propanediamine, butanediamine, pentanediamine, hexanediamine, diethylenetriamine, 1,2-diaminoethane, 1,3-diaminopropane (propane-1,3-diamine), 4-amino-3-hydroxybutyric acid, N-(2-hydroxyethyl)ethylenediamine, 4-amino-2-hydroxybutyric acid, 2-hydroxy-4-aminobutylic acid, 1-β-homoserine, 1-threonine, N-β-aminoethylglycine, putrescine (butane-1,4-diamine), cadaverine (pentane-1,5-diamine), hexamethylenediamine (hexane-1,6-diamine), 1,2-diaminopropane, diphenylethylenediamine, diaminocyclohexane. Diethylene-triamine, bis(3-aminopropyl)amine, triethylenetetramine, tris(2-aminoethyl)amine, spermine, spermidine, norspermidine, bis(3-aminopropyl)-1,3-propanediamine, 1,2-bis(3-aminopropyl-amino)ethane, N,N'-bis(3-aminopropyl)-1,3-propanediamine, tris(hydroxylmethyl)amino-methane, diaminobenzidine, N-ethyl-N'-(3-dimethylaminopropyl)carbodiimide, meso-erythritol, triazacyclononane, tetraazacyclododecane, threitol, dithiothreitol, trimethylcyclo-hexane-1,3,5-tricarboxylic acid, trimethylbis(hexamethylene)triamine, bis(hexamethylene)-triamine, arginine, oxylyldiaminopropionic acid, 3-amino-1,2-propanediol, 3-bromo-1,2-propanediol, 3-chloro-1,2-propanediol, 3-fluoro-1,2-propanediol, DL-glyceric acid, diaminopropionic acid, glucoheptonic acid and, 1,2,4-butanetriol, 2,2-bis(hydroxymethyl)butyric acid, 1,3-diamino-2-propanol and 2-(3-aminopropylamino)ethanol, and 3-((3-aminopropyl)amino)propanol; aspartic acid, glutamic acid, asparagine, glutamine, lysine, ornithine, serine, and threonine or benzyl triols or aminohydroxybenzoic acids or benzenetriol, dihydroxybenzoic acid, diaminobenzoic acid, diaminophenol, diaminobenzoic acid, aminohydroxybenzoic acid, aminosalicylic acid, hydroxyanthranilic acid, hydroxyisophthalic acid, aminoisophthalic acid, 4-(hydroxyl-methyl)cyclopentane-1,3-diol, deoxyfuconojirimycin, deoxynojirimycin, prostaglandins, hydroxylmethylpiperidinol, dihydroxy(hydroxymethyl)aminocyclopentane, diaminophenol, benzenetetracarboxylic acid, benzenetricarboxylic acid, aminobenzenediol, dihydroxybenzoic acid, aminohydroxybenzoic acid, trihydroxyaniline, benzenetriol, dimethoxybenzenediamine, trihydroxyphenol, (diaminophenoxy)benzenediamine and aminobromophenol. The cyclodextrin consist of (n=) six, seven, and eight glucopyranose units or branched with glucosyl or maltosyl group. The "Lipid" is a lipophilic compound or their diesters including but not limited to fatty acids or steroids or sterols or sterol-like compound or lipo-vitamin. Although the CD is a large carrier, it is still considered as one of the three carriers attached to the center backbone though the same or different linkers of alkylation or esterification or etherification or amidation between carrier groups and center backbones. Each linker may be as simple as oxygen or nitrogen or sulfur or other single atom to form an ester or ether or amide or thiol bond or alike between the carrier and center backbone. Alternatively, each linker may be single or replicate linkers selected from amino, succinylamino, acetamido, aminopentanamido, aminoacetyl, acryloyl, thiopropanoayl, N-(mercaptomethyl)propionamido, mercaptopropylthiopropanoyl, (1,2-dihydroxy-3-mercaptopropylthio)propanoyl, succinyl, acetyl, oxopentanoyl, carbamoyl, aminoalkyl, glutaramido, aminoethanethiol, mercaptopropanol, (hydroxypropylthio)propanoayl, 3-((2-propionamidoethyl)-disulfanyl)propanoayl, (((acetamidoethyl)disulfanyl)propanoyloxy)glutaramido, aminoethanethioate, 2-hydroxyacetic proprionic anhydride, glycerol or glycerol-like analogues, polyamines, diamines, triamines, tetraamines, aminodiol, aminotriols, aminoalcohols and amino acids having three available binding positions or sites, triols, tetraols, erythritol, triacids, tetracid, tetraacetic acid, glucoheptonic acid, and tartaric acid, including but not limited to ethanediamine, propanediamine, butanediamine, pentanediamine, hexanediamine, diethylenetriamine, 1,2-diaminoethane, 1,3-diaminopropane (propane-1,3-diamine), 4-amino-3-hydroxybutyric acid, N-(2-hydroxyethyl)ethylenediamine, 4-amino-2-hydroxybutyric acid, 2-hydroxy-4-aminobutylic acid, 1-β-homoserine, 1-threonine, N-β-aminoethylglycine, putrescine (butane-1,4-diamine), cadaverine (pentane-1,5-diamine), hexamethylenediamine (hexane-1,6-diamine), 1,2-diaminopropane, diphenylethylenediamine, diaminocyclohexane. Diethylenetriamine, bis(3-aminopropyl)amine, triethylenetetramine, tris(2-aminoethyl)amine, spermine, spermidine, norspermidine, bis(3-aminopropyl)-1,3-propanediamine, 1,2-bis(3-amino-propylamino)ethane, N,N'-bis(3-aminopropyl)-1,3-propanediamine, tris(hydroxyl-methyl)aminomethane, diaminobenzidine, N-ethyl-N'-(3-dimethylaminopropyl)-carbodiimide, meso-erythritol, triazacyclononane, tetraazacyclododecane, threitol, dithiothreitol, trimethylcyclohexane-1,3,5-tricarboxylic acid, trimethylbis(hexamethylene)triamine, bis(hexamethylene)-triamine, arginine, oxylyldiaminopropionic acid, 3-amino-1,2-propanediol, 3-bromo-1,2-propanediol, 3-chloro-1,2-propanediol, 3-fluoro-1,2-propanediol, DL-glyceric acid, diaminopropionic acid, glucoheptonic acid and, 1,2,4-butanetriol, 2,2-bis(hydroxymethyl)butyric acid, 1,3-diamino-2-propanol and 2-(3-aminopropyl-amino)ethanol, and 34-(3-aminopropyl)-amino)propanol; aspartic acid, glutamic acid, asparagine, glutamine, lysine, ornithine, serine, and threonine or benzyl triols or aminohydroxybenzoic acids or benzenetriol, aminosalicylic acid. In some cases, the linker may be co-extensive with or a part of the backbone or functional group component used to synthesize the conjugates.

Typical coupling reaction of the conjugates involves with one or more or combination or in series of alkylation including N-alkylation or O-alkylation, etherification, esterification and amidation chemical processes. The general structure is meant to include all racemers or structural isomers of the structure, as they may be functionally equivalent. The PEG chain preferably consists of between about 5 and 115 subunits, and is preferably substantially monodisperse. $R_i$ is the terminal group on the PEG chain may be selected from a wide variety of chemical moieties. Hydroxyl or methoxy is commonly selected as the terminal groups. $R_i$ preferably has a molecular weight of less than about 650. Commercially available PEG-lipid monoesters may be used to formulate many compounds by directly linking new moieties to the available positions on the center backbone.

In one aspect of the present invention, no drug or peptide or biomolecule will be selected as the center backbone. Unlike prodrugs modified from bioactive agents, one of major applications of the present invention is for drug delivery, therefore the conjugates themselves as a delivery vehicle are chemically stable and preferably having less or no toxic to the body.

The terminal group on the PEG chain may be selected from a wide variety of chemical moieties. Such moieties preferably have a molecular weight of less than 650. Such moieties include —OH, —OCH$_3$, —NH$_2$, —COOH, —OCH$_2$CH$_3$, —OCH$_2$CH$_2$OH, —COCH═CH$_2$, —OCH$_2$CH$_2$NH$_2$, —OSO$_2$CH$_3$, —OCH$_2$C$_6$H$_6$, —OCH$_2$COCH$_2$CH$_2$COONC$_4$H$_4$O$_2$, —CH$_2$CH$_2$—CH$_2$, C$_{10}$H$_{16}$N$_2$O$_3$S and —OC$_6$H$_6$. The terminal group may be a functional group that facilitates linking therapeutic or targeting agents to the surface of lipid vesicle aggregates. Amino acids, amino alkyl esters, biotins, maleimide, diglycidyl ether, maleinimido propionate, methylcarbamate, tosylhydrazone salts, azide, propargylamine, propargyl alcohol, succinimidyl (NHS) esters (e.g., propargyl NHS ester, NHS-biotin, sulfo-NHS-LC-biotin, or NHS carbonate), hydrazide, succinimidyl ester, succinimidyl tartrate, succinimidyl succinate, and toluenesulfonate salt are useful for such linking. Linked therapeutic and targeting agents may include Fab fragments, cell surface binding agents, and the like. Additionally, the terminal group may include functional cell-targeting ligands such as folate, transferrin and molecules such as monoclonal antibodies, ligands for cellular receptors or specific peptide sequences may be attached to the liposomal surface to provide specific binding sites. The terminal group may be neutral or include either negatively or positively charged head-groups such as decanolamine, octadecylolamine, octanolamine, butanolamine, dodecanolamine, hexanolamine, tetradecanolamine, hexadecanolamine, oleylamine, decanoltrimethylaminium, octadecyloltrimethylaminium, octanoltrimethylaminium, butanoltrimethylaminium, dodecanoltrimethylaminium, hexanoltrimethylaminium, tetradecanoltrimethylaminium, hexadecanoltrimethylaminium, oleyltrimethylaminium, for example. Other useful R groups include fatty acids or alkyl groups such as alkoxy moieties, amino acids, and sugars including monosaccharides, disaccharides, trisaccharides and the oligosaccharides containing 1, 2, 3, and 4 or more monosaccharide units respectively. Additionally, targeting moieties such as antibody fragments and vitamins may also be used as R groups. The molecular weight of the R group is preferably less than about 650, and for most applications the R group is preferably easily polarized, in order to increase the binding and interaction with proteins at the targeted sites. However, well balanced ionic R groups are advantageously employed for certain modes of administrations such as topical gels and oral solutions targeting the mouth and throat.

The present invention includes linking chemical groups that may be selected to optimize and improve PEG-CD-lipid based formulations. Selecting an appropriate linker between lipo-portion or PEG or CD and backbone may be important for several reasons, as described below.

It is well understood that a drug or compound as a xenobiotic, the normal human body doesn't need it. Ideally, a drug should reach the site of action intact, cure the disease, and leave the body after it completes its mission. However, drug developers often face the dilemma that 70 to 90% of drugs under development have water solubility or permeability problem [Thayer, A M. *Chemical & Engineering News*. 88 (2010) 13-18], so that the drug may not reach its site of action and achieve its therapeutic effect, or too slow, so that it stays in the body for a long time causing side effects. An object of this invention is to develop the polymer-CD-lipids with unique linkers to help drugs to achieve therapeutic goals.

Xenobiotics follow metabolic processes to be removed from the body. This process most commonly involves cytochrome P450 enzymes. These enzymes are a super family of proteins found in all living organisms. In humans, as well as all other mammalian species, this enzyme system is found principally in the liver but exists in all other organs and tissues. These enzymes catalyze the following reactions: aromatic hydroxylation; aliphatic hydroxylation; N-, O-, and S-dealkylation; N-hydroxylation; N-oxidation; sulfoxidation and deamination. Of particular importance to the present invention are the breakdown processes that the vesicles formed from news lipids, and the new lipids themselves, are expected to undergo. Methoxyl and methylamine groups are expected to undergo demethylation. Amines are expected to undergo N-oxidation or deamination. Sulfur bonds are expected to undergo S-oxidation. Esters and amides are expected to undergo hydrolysis. Since different organs and tissues have differing abilities to perform these different reactions, it is a further objective of the present invention to provide linkers with optimal degradation properties.

Similarly different microenvironments within the body favor different breakdown processes. For example, acidic gastric fluids favors breakdown of thiol linkages. Therefore, it is still another object of this invention to provide new molecules for improving the biocompability of a therapeutic agent and for designing drug delivery formulations for diverse physiological microenvironments.

Of the three linked PEG, CD and lipophilic components or lipo-vitamins are digestible by humans while cyclodextrins are partially digestible and PEG is not. Breaking the linkage among the three components may result in increased clearance for all. It is therefore an object of the invention to use varying biodegradable linkers for optimizing clearance rates of lipid vesicles and lipids used for drug delivery.

When attached to a polymer, any inherit property of the molecules may be inactive. It is therefore an object of the invention to use less biodegradable linkers for stabilizing the bond between the center backbone and the carrier groups, especially when a portion of the conjugates alone may be relatively toxic.

In one aspect of the present invention involves coupling reactions of the conjugates with one or more or combination or in series of alkylation including N-alkylation or O-alkylation, etherification, esterification and amidation chemical processes. For practical and economic reasons, it is preferable making those conjugates from simple processes whenever possible at low costs.

Retaining power of a solubilizing enhancer may be important in drug formulations and preventing drug precipitation from dilution or circulation in the body fluids. The present invention provides the means of enhancing retaining power by inclusion more hydrophobic carrier groups into polymer-CD-lipid conjugates. In addition, with increased retaining power of the conjugates, the use of preservative may be eliminated for parenteral products since the sterile filtration is possible with a relative low concentration of the polymer conjugates in the dosage forms which typically form a true solution product.

The CD groups in the conjugates of the present invention have larger surface polarity than polymer chains or lipophilic carriers. For instance, those PEG-CD-lipid conjugates provide a better drug dispersion for their applications in nano-suspension or nanoparticles, especially for some amphiphatic drugs or other compounds; this provides a better equilibrium for the drug or other compounds to partition into apolar cavity or the lipophilic core of the conjugates.

When using existing PEG-lipids such as Capmul®, Centrophase®, Cremophor®, Labrafac®, Labrafil®, Labrasol® and Myverol® for oral liquid formulations, a taste masking agent may be used which may have additional issues for manufacturing processes and costs. PEG-CD-lipid conjugates generally taste better than other types of PEG-lipids conjugates, and elimination of the need for taste making agents may be possible.

PEG-CD-lipid conjugates in the present invention may be formulated into injectable preparations free from sugars which are commonly used to stabilize lyophilized proteins and peptides for injectables. Injectables prepared with PEG-CD-lipid conjugates are very stable even under high temperature or high humidity conditions. Reducing or eliminating the use of sugars in pharmaceutical preparation is especially beneficial for patients with diabetes mellitus.

The polymer chains in the conjugates of the present invention are preferably monodisperse or narrow-disperse PEG. Materials and methods for synthesizing such monodisperse PEG chains are disclosed in U.S. patent application Ser. No. 12/802,197, which is hereby incorporated by reference in its entirety. Preferably more than 30% of the PEG chains in a particular conjugate have the same molecular weight. More preferably, more than 50% have the same molecular weight. Most preferably, more than 80% have the same molecular weight.

In one aspect of the current invention, the general structure is meant to include all racemers or structural isomers of the structure, as they may be functionally equivalent. When the polyethylene glycol is used as the polymer, the PEG chain preferably consists of between about 5 and 115 subunits, and is preferably substantially monodisperse. R is the terminal group on the PEG chain may be selected from a wide variety of chemical moieties. R preferably has a molecular weight of less than about 650.

Generally, the present invention includes compositions and methods for synthesizing PEG-CD-lipid conjugates comprising a center backbone with one PEG chain and one lipophilic group bonded to the backbone, the PEG-lipid may then attach to one of activated hydroxyl group of CDs, likewise the activated CDs may be attached to the center backbone by the similar processes as other carriers. The conjugation undergoes alkylation including N-alkylation or O-alkylation, etherification, esterification and amidation chemical processes. Selected linkers may be used to form ester or ether or amide bonds between the backbone and the PEG chain or the CD or the lipophilic group or prior to the conjugation to the center backbones. The backbone comprises glycerol or glycerol-liking having three available binding positions or diamines, triamines, tetramine and polyamines or diaminoalcohol or amino acids having three available binding positions and the lipophilic carrier group comprises fatty acids or sterols or cholesterol or cholesterol-like having a single hydroxyl group or tocopherol or tocotrienol or cholecalciferol or retinol, retinal, and retinoic acid.

Variations of the invention include a variety of compounds as for the center backbone with at least three available binding positions. Molecules having two available binding positions, such as diamines, aminoalcohols or amino acids may be chemically extended to three binding sites.

While positional isomers may be produced during synthesis of the polymer-carbohydrate-lipid conjugates, such isomers may be functionally equivalent. However, the choice of isomer may have implications in a variety of delivery process such as intracellular transport of lipophilic molecules as well as their use as vehicles in pharmaceutical applications. For example, isomers may differ in the ability to stabilize a compound during solubilizing and storage.

Though it is possible to use a variety of center backbone for the preparation of a polymer-CD-lipid conjugates, incorporating linear or cyclic molecule in practicing the invention is demonstrated to be very powerful. In one hand is because of a sterol or tocopherol or cholecalciferol may largely increase handling ability of "like dissolves like," In other hand, the apolar cavity of CDs provide the "host" site for "guest" molecules. General Structure 2, the backbone may be selected from glycerol or glycerol-like analogues, polyamines (di- or tri- or tetra- or penta-amines), amino acids having three available binding sites, and triols and triacids such as glucoheptonic acid and tartaric acid. The lipophilic component may be selected from a group of compounds including but not limited to cholesterol, stigmasterol, ergosterol, hopanoids, phytosterol, sitosterol, campesterol, brassicasterol, avenasterol adosterol, and stanols (saturated steroid alcohols or hydrogenated sterols), retinoids, retinals, retinoic acid, tretinoin, carotenoids, β-carotene, α-tocopherol, tocotrienols, cholecalciferol, ergocalciferol, astaxanthin, auroxanthin, capsanthin, capsorubin, chrysanthemaxanthin, cryptoxanthin, fucoxanthin, lutein, neoxanthin, rubixanthin, violaxanthin, zeaxanthin. The CD may be α-cyclodextrin or β-cyclodextrin or γ-cyclodextrin. The same or different linkers may be used through alkylation or etherification or esterification or amidation process between carrier groups and center backbones. Each linker may be as simple as oxygen or sulfur or other single atom. Alternatively, each linker may be single or replicate linkers selected from amino, succinylamino, acetamido, aminopentanamido, aminoacetyl, acryloyl, thiopropanoayl, N-(mercaptomethyl)-propionamido, mercaptopropylthiopropanoyl, (1,2-dihydroxy-3-mercaptopropylthio) propanoyl, succinyl, acetyl, oxopentanoyl, carbamoyl, aminoalkyl, glutaramido, aminoethanethiol, mercaptopropanol, (hydroxypropylthio)propanoayl, 3-((2-propionamido-ethyl)disulfanyl)propanoayl, (((acetamido-ethyl)disulfanyl) propanoyloxy)-glutaramido, aminoethanethioate, and 2-hydroxyacetic proprionic anhydride.

In some cases, the linker may be co-extensive with or a part of the backbone or functional group component used to synthesize the conjugate. Though not shown, the invention also includes compounds in which the carbohydrate is in the center position of the backbone. However, it is more practical to have carbohydrates at the terminus instead of the center of the backbones due to the routes of synthetic chemistry. The general structure is meant to include all racemers or structural isomers of the structure, as they may be functionally equivalent. The PEG chain preferably consists of between about 5 and 115 subunits, and is preferably substantially monodisperse. R is the terminal group on the PEG chain may be selected from a wide variety of chemical moieties. R preferably has a molecular weight of less than about 650.

In another aspect of the present invention, while various fatty acids may be utilized for the preparation of the polymer-CD-lipid conjugates, the myristoleic acid, palmitoleic acid, oleic acid, lauric acid, myristic acid, palmitic acid and stearic acid may be more commonly used. Myristoleic acid, palmitoleic acid, oleic acid palmitic acid and stearic acid may be more preferable.

In one aspect of the present invention, whenever applicable, preferable amino acid linkers are proline, glycine, alanine, lysine, cysteine, valine, isoleucine, leucine, methionine, phenylalanine, histidine, tryptophan, tyrosine, selenocysteine, and arginine, more preferable are proline, glycine, alanine, lysine, cysteine, valine, isoleucine, leucine, methionine, most preferable are proline, glycine, and alanine In this aspect of the invention, in the general structure 2, even though it may not show in the chemical drawing, a linker may comprise one or more carbon atoms in addition to the linker forming an N-alkylation or O-alkylation, ester or ether or amide bond between the carriers and center backbone. Whenever suitable, a simple and low cost coupling process should be chosen to void multiple linkers such as forming a peptide and the linker is preferably oriented so that the backbone is readily coupling to the carrier groups.

The present invention may be practiced using a variety of center backbones void drug moieties. Preferable backbones have at least three available or two expandable positions for carbohydrate or lipid or PEG attachments through alkylation, esterification, etherification or amidation. For those suitable molecules may be used as the backbone including but not limited to the group consisting of ethylenediamine (1,2-diaminoethane, 1,3-diaminopropane (propane-1,3-diamine), putrescine (butane-1,4-diamine), cadaverine (pentane-1,5-diamine), hexamethylenediamine (hexane-1,6-diamine), ethylenediamine, 1,3-diaminopropane, 1,2-diaminopropane, 1,4-diaminobutane, diphenylethylenediamine, diaminocyclohexane, 3-amino-1, 2-propanediol, 3-bromo-1,2-propanediol, 3-chloro-1,2-propanediol, 3-fluoro-1,2-propanediol, DL-glyceric acid, diaminopropionic acid, tartaric acid, glucoheptonic acid and, 1,2,4-butanetriol, 2,2-Bis(hydroxymethyl)butyric acid, 1,3-diamino-2-propanol and 2-(3-aminopropylamino)ethanol, 3-((3-aminopropyl)amino)propanol, diethylenetriamine, spermidine, triethylenetetramine, spermine, norspermidine, bis(3-aminopropyl)-1,3-propanediamine, and bis(hexamethylene)triamine, aspartic acid, glutamic acid, asparagine, glutamine, ornithine, serine and threonine, benzyl triols or aminohydroxybenzoic acids or phenol-like analogues, phenyl diols with a carboxyl group or amine, and diamines with a hydroxyl or carboxyl group, diaminobenzoic acid, aminohydroxybenzoic acid, aminosalicylic acid, hydroxyanthranilic acid, hydroxyisophthalic acid, aminoisophthalic acid. For example, a suitable center backbone may be selected from 4-(hydroxymethyl)cyclopentane-1,3-diol, deoxyfuconojirimycin, deoxynojirimycin, prostaglandins, hydroxymethylpiperidinol, dihydroxy(hydroxymethyl) aminocyclopentane, diaminophenol, benzene-tetracarboxylic acid, benzenetricarboxylic acid, aminobenzenediol, dihydroxybenzoic acid, aminohydroxybenzoic acid, trihydroxyaniline, benzenetriol, dimethoxybenzenediamine, trihydroxyphenol, (diaminophenoxy)-benzene-diamine or aminobromophenol.

The polymer-CD-lipid conjugates of the present invention may be used for many applications. Formulation and delivery of pharmaceutical and cosmetic agents have been described. Additionally, the polymer-CD-lipid conjugates of the present invention may be used in other contexts where water soluble vehicles are advantages, for example industrial and food processes The terminal group on the PEG chain may be selected from a wide variety of chemical moieties. Such moieties preferably have a molecular weight of less than 650. Such moieties include —$NH_2$, —COOH, —$OCH_2CH_3$, —$OCH_2CH_2OH$, —COCH=$CH_2$, —$OCH_2CH_2NH_2$, —$OSO_2CH_3$, —$OCH_2C_6H_6$, —$OCH_2COCH_2CH_2COONC_4H_4O_2$, —$CH_2CH_2$—$CH_2$, $C_{10}H_{16}N_2O_3S$ and —$OC_6H_6$. The terminal group may be a functional group that facilitates linking therapeutic or targeting agents to the surface of micro vesicle aggregates. Amino acids, amino alkyl esters, biotins, maleimide, diglycidyl ether, maleinimido propionate, methylcarbamate, tosylhydrazone salts, azide, propargylamine, propargyl alcohol, succinimidyl (NHS) esters (e.g., propargyl NHS ester, NHS-biotin, sulfo-NHS-LC-biotin, or NHS carbonate), hydrazide, succinimidyl ester, succinimidyl tartrate, succinimidyl succinate, and toluenesulfonate salt are useful for such linking. Linked therapeutic and targeting agents may include Fab fragments, cell surface binding agents, and the like. Additionally, the terminal group may include functional cell-targeting ligands such as folate, transferrin and molecules such as monoclonal antibodies, ligands for cellular receptors or specific peptide sequences may be attached to the liposomal surface to provide specific binding sites. The terminal group may be neutral or include either negatively or positively charged head-groups such as decanolamine, octadecylolamine, octanolamine, butanolamine, dodecanolamine, hexanolamine, tetra-decanolamine, hexadecanolamine, oleylamine, decanoltrimethylaminium, octadecyloltrimethylaminium, octanoltrimethylaminium, butanoltrimethylaminium, dodecanoltrimethylaminium, hexanoltrimethylaminium, tetradecanoltrimethylaminium, hexadecanoltrimethylaminium, oleyltrimethylaminium, for example. Other useful $R_t$ groups include alkyl groups such as alkoxy moieties, amino acids, and sugars including monosaccharides, ascorbic acid, gluconic acid, glucaric acid, glucuronic acid, galacturonic acid, disaccharides, trisaccharides and the oligosaccharides containing 1, 2, 3, and 4 or more monosaccharide units respectively. Additionally, targeting moieties such as antibody fragments and vitamins may also be used as $R_i$ groups. Generally, the $R_i$ group is highly soluble in water. The molecular weight of the $R_i$ group is preferably less than about 650, and for most applications the $R_i$ group is preferably easily polarized, in order to increase the binding and interaction with proteins at the targeted sites. However, well balanced ionic $R_i$ groups are advantageously employed for certain modes of administrations such as topical gels and oral solutions targeting the mouth and throat.

Depending on the choice of backbone, functional groups and linkers, the compounds of the invention may be categorized into several classes. These classes include and not limited to (a) sterol and "fat soluble" vitamin based: cholesterylglycerolcyclodextrin-polyethylene-(CGC-PEGs); tocopherylglycerolcyclodextrin-polyethyleneglycols (TGC-PEGs), cholesteryldiethylenetetramine-cyclodextrin-polyethyleneglycols (CDC-PEGs), tocopheryldiethylenetetramine-cyclodextrinpolyethyleneglycols (TDC-PEGs), cholesteryltriethylenetetraminecyclodextrin-polyethyleneglycols (CTC-PEGs), and tocopheryltriethylenetetramine-cyclodextrin-polyethyleneglycols (TTC-PEGs); (b) fatty acid based: Oleoylglycerol-cyclodextrin-polyethyleneglycols (OGC-PEGs); oleoyldiethylenetetramine-cyclodextrin-polyethyleneglycols (ODC-PEGs), oleoyltriethylenetetramine-cyclodextrin-polyethyleneglycols (OTC-PEGs) and myristoylglycerol-cyclodextrin-polyethyleneglycols (MGC-PEGs); myristoyl-diethylenetetramine-cyclodextrin-polyethyleneglycols (MDC-PEGs); myristoyltriethylene-tetraminecyclodextrin-polyethyleneglycols (MTC-PEGs).

In one aspect of the present invention, a Polymer-CD-lipid conjugate composing a center backbone, a cyclodextrin, a polymer and a lipid is generally classified in Table 3.

TABLE 3

Typical Composition of Polymer-CD-lipid Conjugate

| CD | Backbone | Lipid | Polymer |
|---|---|---|---|
| α, β, γ averaged number of substituent per glucopyranose repeat unit ranging from 0.6 to 3 | glycerol, polyamines, diamines, triamines, tetraamines, aminodiol, aminotriols, aminoalcohols, triols, tetraols, erythritol, triacids, tetracid, tetraacetic acid, glucoheptonic acid, tartaric acid and amino acids having three available binding positions or sites | lauric acid myristic acid palmitic acid stearic acid myristoleic acid palmitoleic acid sapienic acid elaidic acid vaccenic acid linoleic acid tocopherols/tocotrienols retinoids/carotenoids Cholecalciferol steroids/sterols | mPEG$_n$ n = number of ethylene glycol subunit ranging from 5 to 115 |

In further detail of the classification, a polymer-CD-lipid conjugate includes and not limited to oleoyl-mPEG-(aminopropoxy)acetocyclodextrin, stearoyl-mPEG-(aminopropoxy)-acetocyclodextrin, palmitoyl-mPEG-(aminopropoxy)acetocyclodextrin, myristoyl-mPEG-(aminopropoxy)acetocyclodextrin, cholestery-mPEG-(aminopropoxy)acetocyclodextrin, cholestery-mPEG-(aminopropoxy)acetocyclodextrin, tocopheryl-mPEG-(aminopropoxy)acetocyclodextrin, retinoyl-mPEG-(aminopropoxy)acetocyclodextrin, retinoyl-mPEG-(aminopropoxy)-acetocyclodextrin, cholecalciferol-mPEG(aminopropoxy)acetocyclodextrin, oleoylpropane-diaminecyclodextrin-mPEG, $^\varepsilon$N-cyclodextrin-$^\alpha$N-oleoyl-mPEG-lysinate, $^\varepsilon$N-cyclodextrin-$^\alpha$N-myristoyl-mPEG-lysinate, $^\varepsilon$N-cyclodextrin-$^\alpha$N-stearoyl-mPEG-lysinate, stearoylpropanediamine-cyclodextrin-mPEG, oleoyldiethylenetriamine-bis-mPEG-cyclodextrin, palmitoyldiethyletriamine-bismonomethoxyl-PEG-ether-cyclodextrin, oleoyltriethylenetetramine-β-cyclodextrin-bismPEG, palmitoyl-propanediamine-cyclodextrin-bismPEG, myristoylpropanediamine-cyclodextrin-mPEG, palmitoylpropane-diamine-cyclodextrin-mPEG, cholesterypropanediamine-cyclodextrin-mPEG, N$^\varepsilon$-cyclodextrin-N$^\alpha$-cholesterol-mPEG-lysinate, cholesterydiethylenetriamine-cyclodextrin-mPEG, α-tocopheroltriethylene-tetramine-bismonomethoxyl-PEG-ether-cyclodextrin, cholestertriethyl-enetetramine-bismPEG-cyclodextrin, cholesterytriethylenetetramine-cyclodextrin-bismPEG, cholesterytriethylenetetramine-β-cyclodextrin-mPEG, tocopherylpropanediamine-cyclodextrin-mPEG, retinoylpropanediamine-cyclodextrin-mPEG, retinoyldiethylenetriamine-cyclodextrin-mPEG, cholecalciferoldiethylenetriamine-cyclodextrin-mPEG, cholecalciferoldiethylenetriamine-bismPEG-cyclodextrin, cyclodextrin-tocopherylethylene-bismPEG-aminosalicylate, cholecalciferoldiethylenetriaminemono-bismPEG-cyclodextrin, cholesterylascorbyldiethylenetriamine-tryptophanyl-mPEG-cyclodextrin, cholesterolascorbyl-mPEG-propanediaminocyclodextrin, cholesterolaspartate-mPEG-cyclodextrin, cholesteryloleoylascorbyl-diethylenetriamine-mPEG-cyclodextrin, cholesteryl-retinoyldiethylenetriamine-mPEG-cyclodextrin, cholesterolascorbyl-triethylenetetramine-bismonomethoxy-PEG-ether-cyclodextrin, cyclodextrin-tocopherol-mPEG-lysinate, cholesteroltriethylenetetramine-bismPEG-cyclodextrin, cholesterololeoyl-cyclodextrin-diethylenetriamine-mPEG, bismPEG-propanediamine-serinol-N-cholesterol-N'-cyclodextrin, cyclodextrindiamino-2-propanolcholesterolmPEG-ascorbate, cholecalciferolascorbyldiethylene-triamine-cyclodextrin-mPEG, $^\varepsilon$N-cyclodextrin-$^\varepsilon$N-cholesteryl-$^\alpha$N-acetyl-mPEG-lysinate, cholecalciferoldipropylenetriamine-mPEG-cyclodextrin, cholesteryldiethylenetriaminetryptophanyl-mPEG-cyclodextrin, N-cyclodextrin-cholesterolaspartate-mPEG, cholesterylretinoyltriethylene-tetramine-mPEG-cyclodextrin, cholesteryltriethylenetetramine-bis-mPEG cyclodextrin, $^\varepsilon$N-cyclodextrin-$^\varepsilon$N-α-tocopherol-$^\alpha$N-acetylmonomethoxyl-PEG-ether-lysinate, α-tocopherol-triethylenetetramine-bismPEG-cyclodextrin, cholesterolascorboyldiethylenetriamine-mPEG-cyclodextrin, cholecalciferololeoylascorboyldiethylenetriamine-mPEG-cyclodextrin and cholesteryloleoylascorboyldiethylenetriamine-mPEG-cyclodextrin.

In another aspect of the present invention, the lipid may be selected from polyunsaturated fatty acids or polyunsaturated fatty alcohols including but not limited to Stearidonic acid, Eicosatrienoic acid, Eicosatetraenoic acid, Eicosapentaenoic acid, Heneicosapentaenoic acid, Docosapentaenoic acid, Docosahexaenoic acid, Tetracosapentaenoic acid, Tetracosahexaenoic acid, Docosadienoic acid, Adrenic acid, Docosapentaenoic acid, Rumenic acid, Rumenic acid, α-Calendic acid, β-Calendic acid, Jacaric acid, α-Eleostearic acid, β-Eleostearic acid, Catalpic acid, Punicic acid, Rumelenic acid, α-Parinaric acid, β-Parinaric acid, Bosseopentaenoic acid and native polyunsaturated alcohols such as farneol, solanesol and dodecaprenol. Hexadecatrienoic acid.

In another aspect the invention includes a molecule comprising a compound represented by the following General Structure 3:

General Structure 3

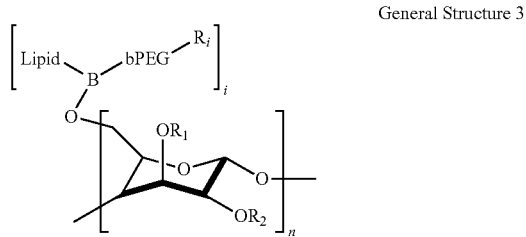

where the bPEG is a branched PEG with 2 or more PEG chains and each PEG chain may consist of between about 5 and 115 subunits. Where $R_i$ is the terminal group and may be selected from a wide variety of chemical moieties. $R_i$ preferably has a molecular weight of less than about 650. The PEG-carbohydrate conjugates are useful for applications other than liposomes, e.g., as a solubility enhancer in water solutions. All other components of the conjugates may remain the same as described under the General Structure 1 and 2.

In one aspect of the current invention, coupling reactions of alkylation, etherification, esterification or amidation between the carriers and center backbone may be achieved with or without added-on linker groups depending on particular center backbones and carrier groups of the conjugates as summarized in the General Structure 4:

General Structure 4

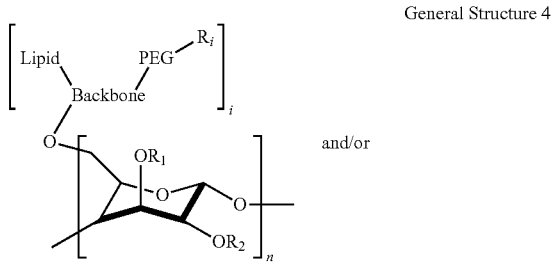

and/or

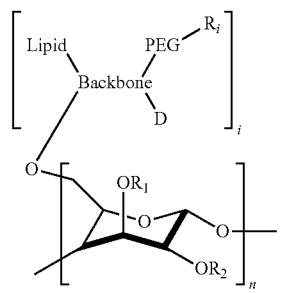

where D is the fourth carrier which may a duplicate lipophilic carrier or PEG. Backbone is a molecule void of a drug moiety comprises glycerol or glycerol-liking having three available binding positions or diamines, triamines, tetramine or diaminoalcohol or aminoalcohols or aminodiol or aminotriols or amino acids having three available binding positions and polyamines having at least three available binding sites or positions. All other components may be the same as described under the General Structures 1 and 2.

A further aspect of the invention, the third and fourth carriers of the PEG-CD-lipid conjugates may be formed through a linked conjugation as presented in the General Structure 5.

General Structure 5

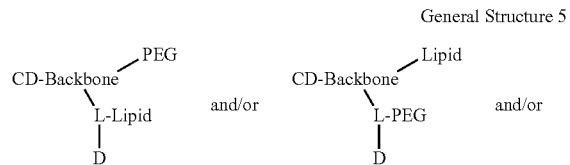

and/or

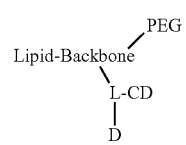

where D is a secondary lipophilic carrier or PEG; L is a coupler selected from a group of molecules included but not limited to glycerol or glycerol-liking having three available binding positions or diamines, triamines, tetramine or diaminoalcohol or aminoalcohols or aminodiol or aminotriols or amino acids having three available binding positions. As showed in Chemical Structure 3, N-bis-monomethoxy-PEG-ether-serinol-N-cholesterol-N'-α-cyclodextrin-propanediamine, the coupler is 3-amino-1,2-propanediol (serinol) and the "D" is a secondary mPEG.

acetyl, oxopentanoyl, carbamoyl, aminoalkyl, glutaramido, aminoethanethiol, mercaptopropanol, (hydroxypropylthio)propanoayl, 3-((2-propionamidoethyl)disulfanyl)propanoayl, (((acetamido-ethyl)disulfanyl)propanoyloxy)glutaramido, aminoethanethioate, and 2-hydroxyacetic proprionic anhydride; and providing a release agent, where the release agent causes the linker to degrade. The release agent may be an acid, light, hypoxia, or a catalyst.

In one aspect, the invention is a method of linking the center backbone to any of the three carrier groups via an amino acid linkage (alkylation or amidation process). The hydroxyl in the carrier groups may be activated by reaction with disucccimidylcarbonate (DCS) or mesylate or tosylate or acrylic acid or strong base (etherification or esterification).

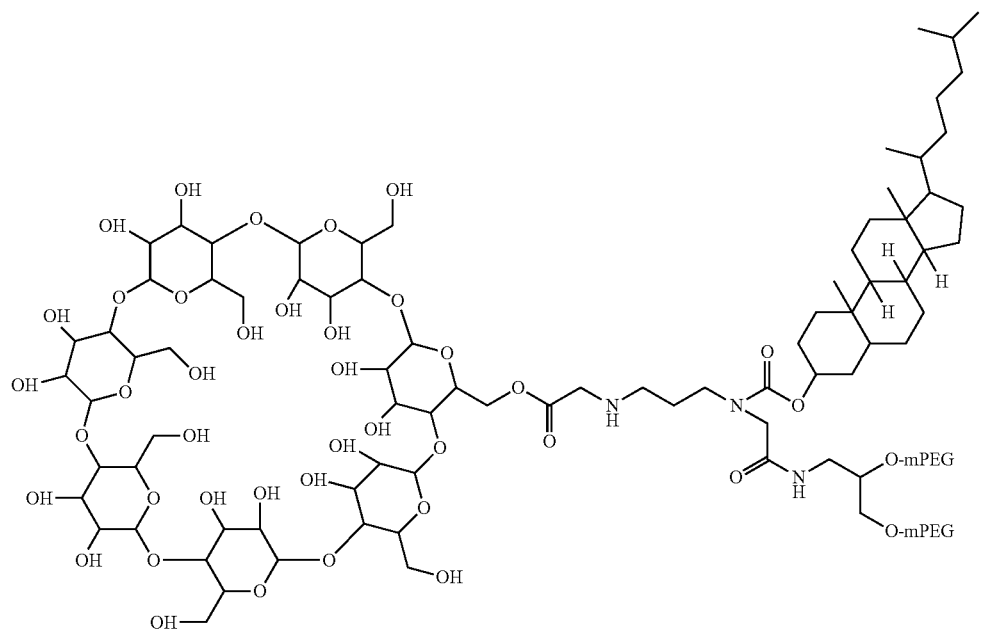

Chemical Structure 3

Another aspect of the invention includes a method of delivering a compound, where the method comprises preparing a PEG-CD-lipid conjugate based formulation of the compound, where the formulation comprises a PEG-CD-lipid conjugates having an amino acid linker and possible secondary linker(s) selected from the group consisting of amino, succinylamino, acetamido, aminopentanamido, aminoacetyl, acryloyl, thiopropanoayl, N-(mercaptomethyl)-propionamido, mercaptopropylthiopropanoyl, (1,2-dihydroxy-3-mercaptopropylthio)propanoyl, succinyl, Example of the synthesis of the PEG-CD-lipid conjugates from mono-aminoacrylate-6-deoxy-β-cyclodextrin with a PEGylatedcholesteryldiethylediamine is shown below in Reaction Scheme 1.

Reaction Scheme 1

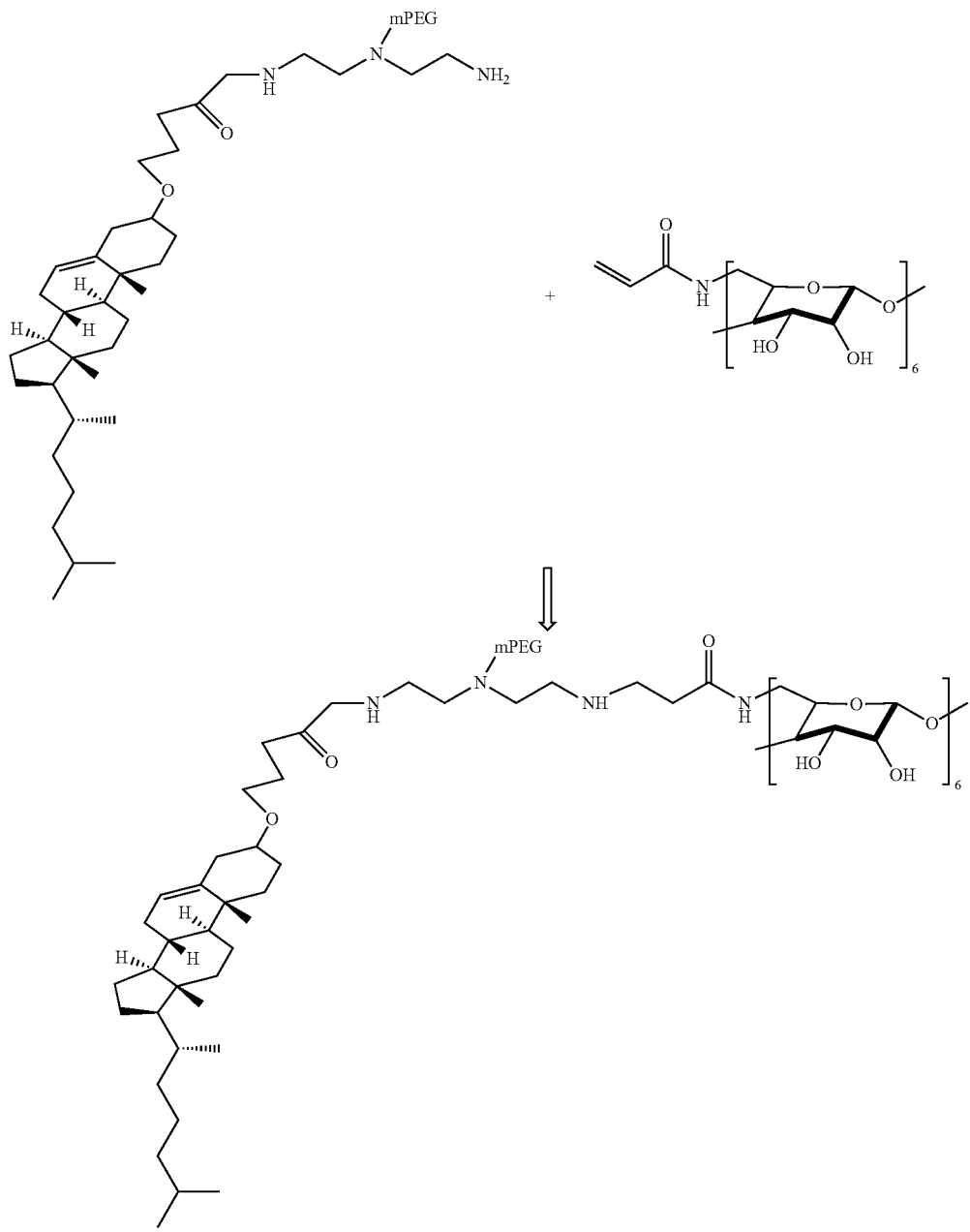

The preparations of allyl-cyclodextrin may be prepared according to modified method from published reports [Jindrich J., et al (19950. *Carbohydr Res.* 266(1):75-80; L I YingJie, et al (2010). *Scientia Sinica Chimica,* 40 (11): 1682-1687] and the PEG-Lipid portion may be synthesized according to out earlier publications [US20120202979 or US20120202890]. This reaction scheme is suitable for carrier groups with all kinds of lipophilic compounds or PEG chains for the CD conjugation. The general structures shown in the application are meant to include all racemers and structural isomers of the structures, as they may be functionally equivalent.

The present invention also demonstrated the using of a branched-PEG as the polymer carrier. Branched-PEGs are commercially available with relative large molecular weights. Thus branched PEGs with smaller PEG chains may be prepared as the same as for a single PEG chain, consequentially. the activated branched PEG was used to make a branched PEG-carbohydrate conjugate as showed in the General Structure 3. As demonstrated in the Reaction Scheme 1, there are multiple chemical processes of alkylation, etherification, esterification or amidation may be involved for making each final product, the steps of each conjugation were designed accordingly.

In another aspect, the invention includes PEG-carbohydrate conjugates comprised of three carrier groups and a center backbone having at three positions available for the conjugation, and one or more linker(s) between one of the carrier groups and the center backbone. Such PEG-carbohydrate conjugates are represented by the General Structures 1 to 5, where the linker may be selected but not limited from a group consisting of amino, succinylamino, acetamido, aminopentanamido, aminoacetyl, acryloyl, thiopropanoayl, N-(mercaptomethyl)propionamido, mercaptopropylthio)-propanoyl, (1,2-dihydroxy-3-mercaptopropylthio)propanoyl, succinyl, acetyl, oxopentanoyl, carbamoyl, aminoalkyl, glutaramido, aminoethanethiol, mercaptopropanol, (hydroxypropylthio)propanoayl, 3-((2-propionamidoethyl)disulfanyl)-propanoayl, (((acetamido-ethyl)disulfanyl)propanoyloxy)glutaramido, amino-ethanethioate, and 2-hydroxyacetic proprionic anhydride. The Table 4 shows certain samples of the PEG-CD-lipid conjugates and in the event of variations of chemical names, the structures shown are meant to be controlling.

TABLE 4

Sample of PEG-CD-lipid conjugates

| Name | Chemical Structure |
|---|---|
| CDC-mPEG: Cholesteryldiethylene-triaminemonohexyl-PEG-cyclodextrin:<br>n = 6 to 8 of glucopyranose units;<br>i = 0.6 to 3 of averaged number of substituent per glucopyranose repeat unit | 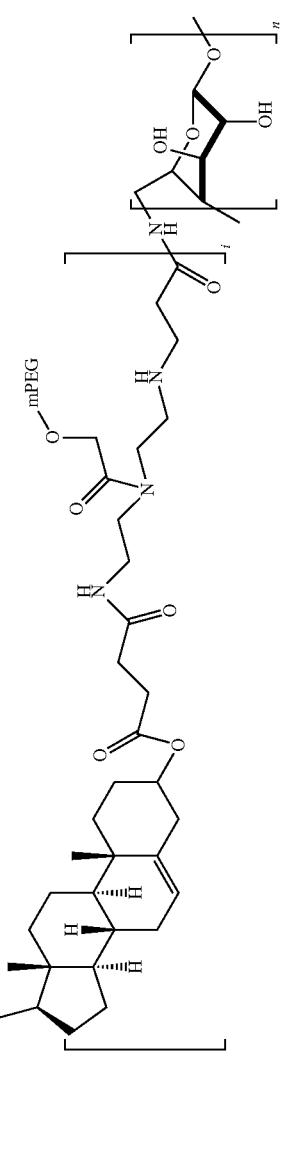 |
| LDC-mPEG: Oleoyldiethylene-triaminemonohexyl-PEG-cyclodextrin:<br>n = 6 to 8 of glucopyranose units;<br>i = 0.6 to 3 of averaged number of substituent per glucopyranose repeat unit | 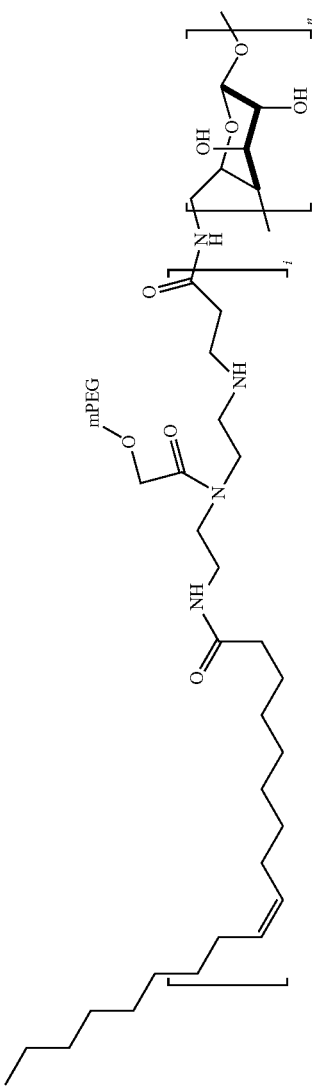 |

TABLE 4-continued

Sample of PEG-CD-lipid conjugates

| Name | Chemical Structure |
|---|---|
| OPC-mPEG: Oleoylpropanediamine-monomexyl-PEG-cyclodextrin: n = 6 to 8 of glucopyranose units; i = 0.6 to 3 of averaged number of substituent per glucopyranose repeat unit | |
| CPC-mPEG: Cholesterylpropanediamine-monomexyl-PEG-cyclodextrin: n = 6 to 8 of glucopyranose units; i = 0.6 to 3 of averaged number of substituent per glucopyranose repeat unit | |

TABLE 4-continued

Sample of PEG-CD-lipid conjugates

| Name | Chemical Structure |
|---|---|
| COEL-mPEG: ᵋN-cyclodextrin-ᵋN-oleoyl-ᵅN-acetyl-monomethoxyl PEG ether lysinate:<br>n = 6 to 8 of glucopyranose units;<br>i = 0.6 to 3 of averaged number of substituent per glucopyranose repeat unit | |
| CCEL-mPEG: ᵋN-cyclodextrin-ᵋN-cholesteryl -ᵅN-acetyl-monomethoxyl PEG ether lysinate:<br>n = 6 to 8 of glucopyranose units;<br>i = 0.6 to 3 of averaged number of substituent per glucopyranose repeat unit | |

TABLE 4-continued

Sample of PEG-CD-lipid conjugates

| Name | Chemical Structure |
|---|---|
| TDC-mPEG: α-Tocopheryl diethylenetriamine-monomethoxyl polyethylene glycol ether cyclodextrin n = 6 to 8 of glucopyranose units; i = 0.6 to 3 of averaged number of substituent per glucopyranose repeat unit | 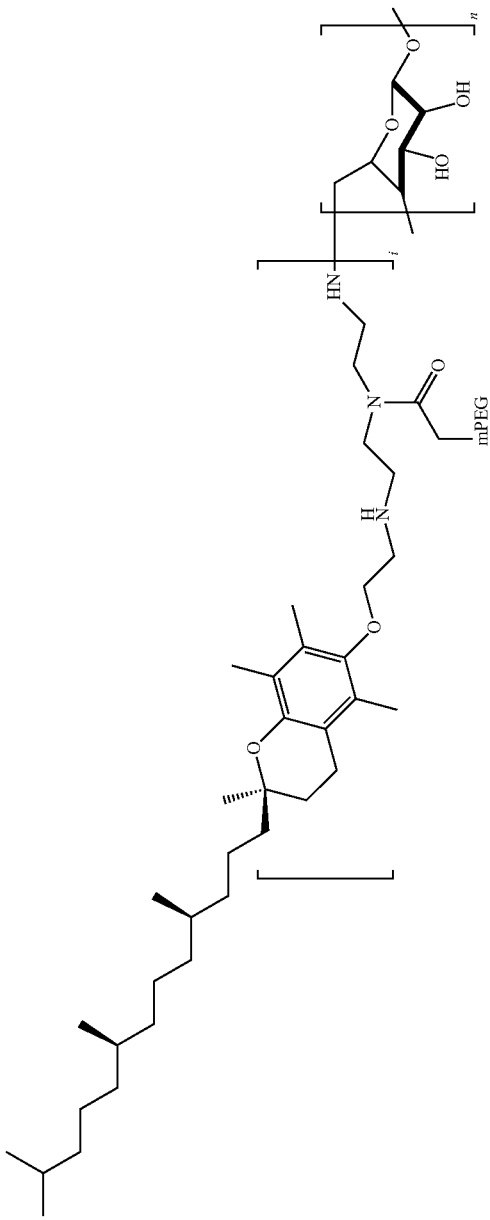 |
| CFADC-mPEG: Cholecalciferoldiethylenetriamine-monomethoxyPEG ether-cyclodextrin: n = 6 to 8 of glucopyranose units; i = 0.6 to 3 of averaged number of substituent per glucopyranose repeat unit | 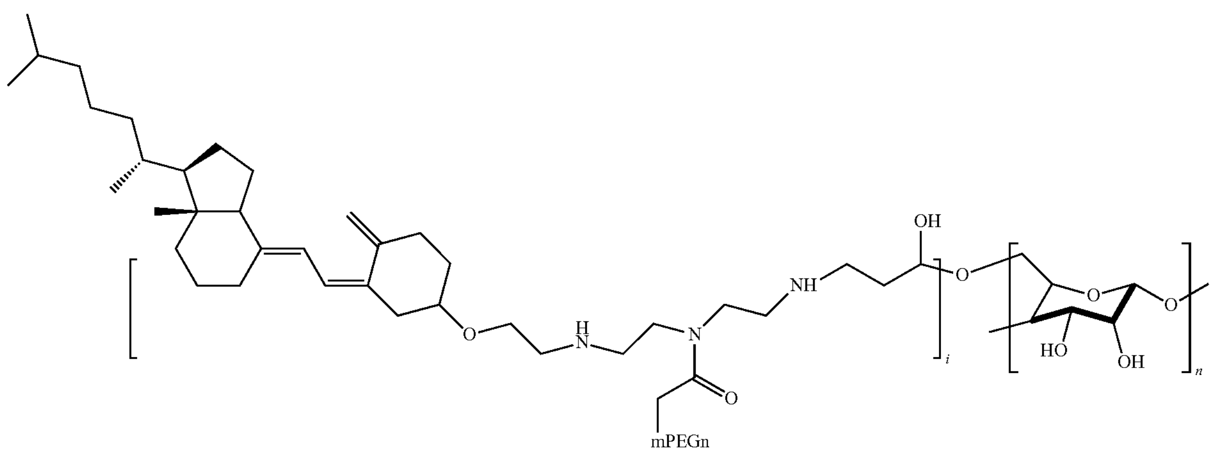 |

TABLE 4-continued

Sample of PEG-CD-lipid conjugates

| Name | Chemical Structure |
|---|---|
| CFDC-mPEG: Cholecalciferol-dipropylenetriamine-monomethoxyPEG ether cyclodextrin:<br>n = 6 to 8 of glucopyranose units;<br>i = 0.6 to 3 of averaged number of substituent per glucopyranose repeat unit | 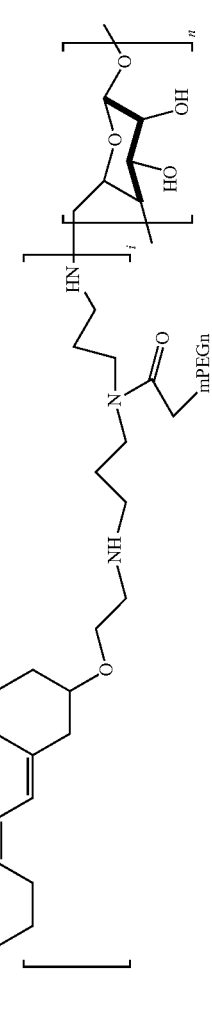 |
| CDC-TrpPEG: Cholesteryldiethylene-triamine-tryptophanyl polyethylene glycol ether cyclodextrin<br>n = 6 to 8 of glucopyranose units;<br>i = 0.6 to 3 of averaged number of substituent per glucopyranose repeat unit | 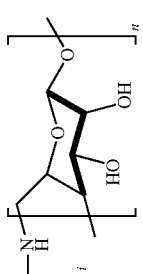 |

TABLE 4-continued

Sample of PEG-CD-lipid conjugates

| Name | Chemical Structure |
|---|---|
| CAC-mPEG: N,N'-Cholesterol-mPEG-aminopropanol-cyclodextrin, n = 6 to 8 of glucopyranose units; i = 0.6 to 3 of averaged number of substituent per glucopyranose repeat unit | 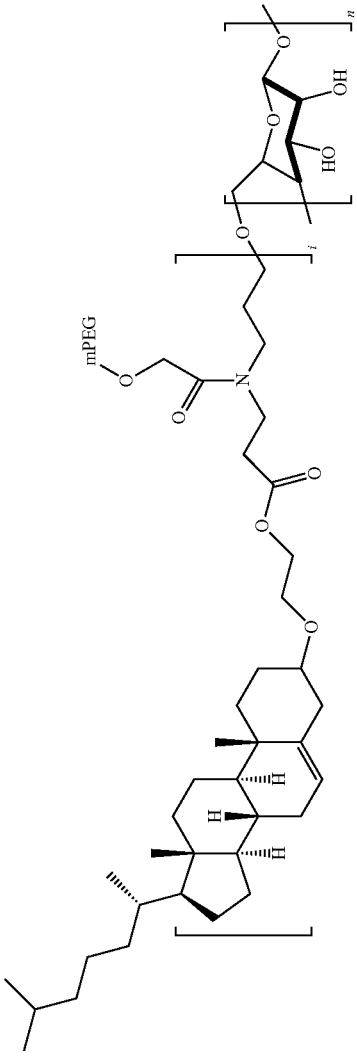 |
| OAC-mPEG: N,N'-oleoyl-mPEG-aminopropanol-cyclodextrin, n = 6 to 8 of glucopyranose units; i = 0.6 to 3 of averaged number of substituent per glucopyranose repeat unit | 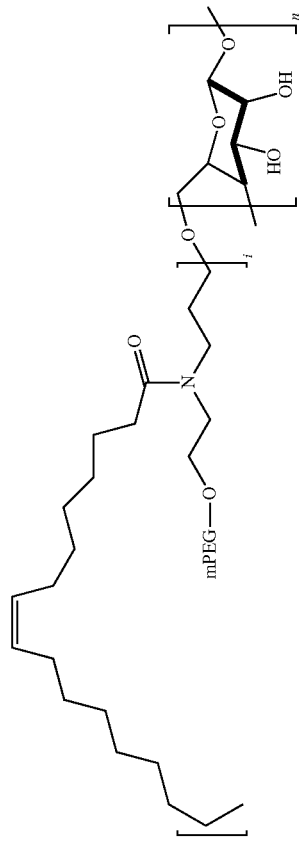 |

TABLE 4-continued

Sample of PEG-CD-lipid conjugates

| Name | Chemical Structure |
|---|---|
| CASPL-mPEG: N-cyclodextrin-cholesterolaspartate-mPEG:<br>n = 6 to 8 of glucopyranose units;<br>i = 0.6 to 3 of averaged number of substituent per glucopyranose repeat unit | |

TABLE 4-continued
Sample of PEG-CD-lipid conjugates
| Name | Chemical Structure |
|---|---|
| CODC-mPEG: Cholesteryloleoyl-diethylenetriamine-mPEG cyclodextrin: n = 6 to 8 of glucopyranose units; i = 0.6 to 3 of averaged number of substituent per glucopyranose repeat unit | 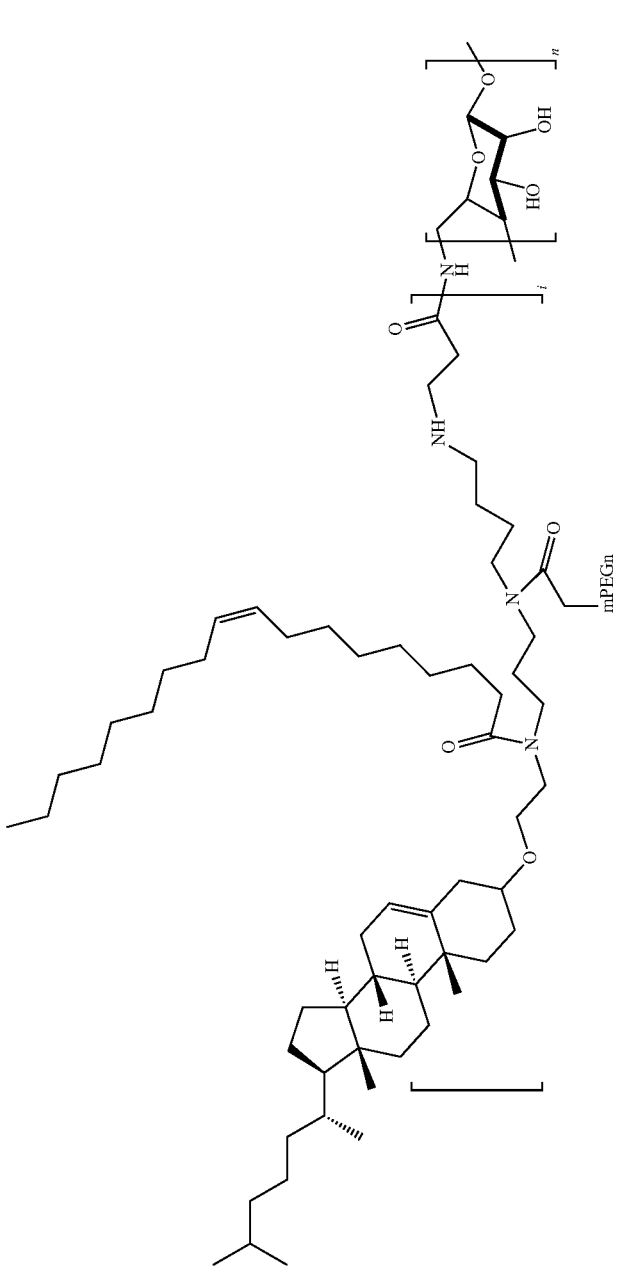 |

TABLE 4-continued

Sample of PEG-CD-lipid conjugates

| Name | Chemical Structure |
| --- | --- |
| CaODC-mPEG: Cholecalciferoloelyl-diethylenetriamine-mPEG cyclodextrin: n = 6 to 8 of glucopyranose units; i = 0.6 to 3 of averaged number of substituent per glucopyranose repeat unit | |
| CRTC-mPEG: Cholesterylretinoyl-triethylenetetramine-mPEG cyclodextrin: n = 6 to 8 of glucopyranose units; i = 0.6 to 3 of averaged number of substituent per glucopyranose repeat unit | 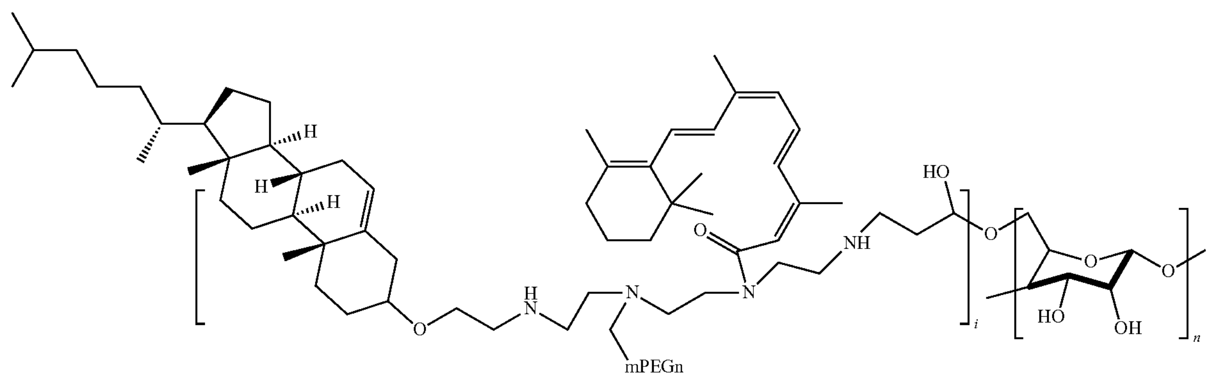 |

TABLE 4-continued

Sample of PEG-CD-lipid conjugates

| Name | Chemical Structure |
|---|---|
| CTC-bismPEG: Cholesteryltriethylene-tetramine-bis-mPEG cyclodextrin: n = 6 to 8 of glucopyranose units; i = 0.6 to 3 of averaged number of substituent per glucopyranose repeat unit | 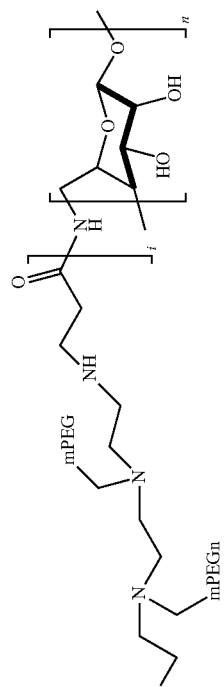 |
| LTL-mPEG: $^6$N-Cyclodextrin-$^\varepsilon$N-acetyl-$^\alpha$N-α-tocopherol-$^\alpha$N-acetyl-monomethoxyl PEG ether lysinate: n = 6 to 8 of glucopyranose units; i = 0.6 to 3 of averaged number of substituent per glucopyranose repeat unit | 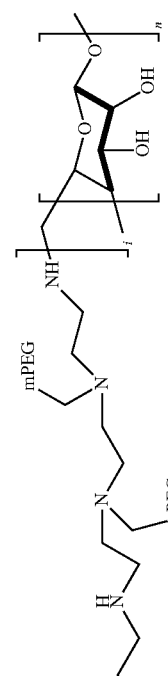 |

TABLE 4-continued

Sample of PEG-CD-lipid conjugates

| Name | Chemical Structure |
|---|---|
| TTC-bismPEG: α-tocopheroltriethylene-tetramine-bismonomethoxyl-PEG ether cyclodextrin: n = 6 to 8 of glucopyranose units; i = 0.6 to 3 of averaged number of substituent per glucopyranose repeat unit | |
| CADTC-mPEG: Cholesterolascorboyldiethylenetriamine-monomethoxyPEG ether cyclodextrin: n = 6 to 8 of glucopyranose units; i = 0.6 to 3 of averaged number of substituent per glucopyranose repeat unit | 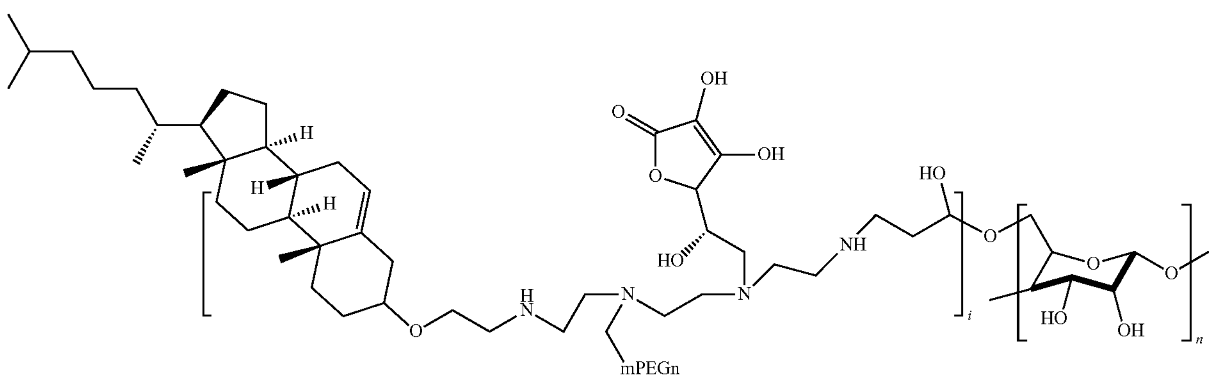 |

TABLE 4-continued
Sample of PEG-CD-lipid conjugates
| Name | Chemical Structure |
|---|---|
| CaOADC-mPEG: Cholecalciferololeoyl-ascorboyldiethylenetriamine-mPEG cyclodextrin:<br>n = 6 to 8 of glucopyranose units;<br>i = 0.6 to 3 of averaged number of substituent per glucopyranose repeat unit | 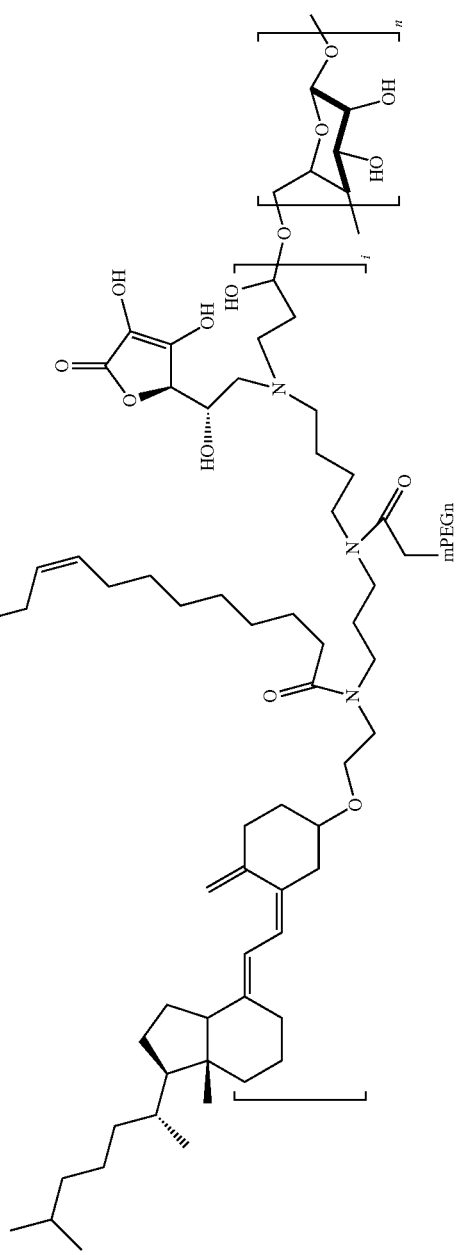 |

TABLE 4-continued

Sample of PEG-CD-lipid conjugates

| Name | Chemical Structure |
|---|---|
| COADC-mPEG: Cholesteryloleoyl-ascorboyldiethylenetriamine-mPEG cyclodextrin:<br>n = 6 to 8 of glucopyranose units;<br>i = 0.6 to 3 of averaged number of substituent per glucopyranose repeat unit | 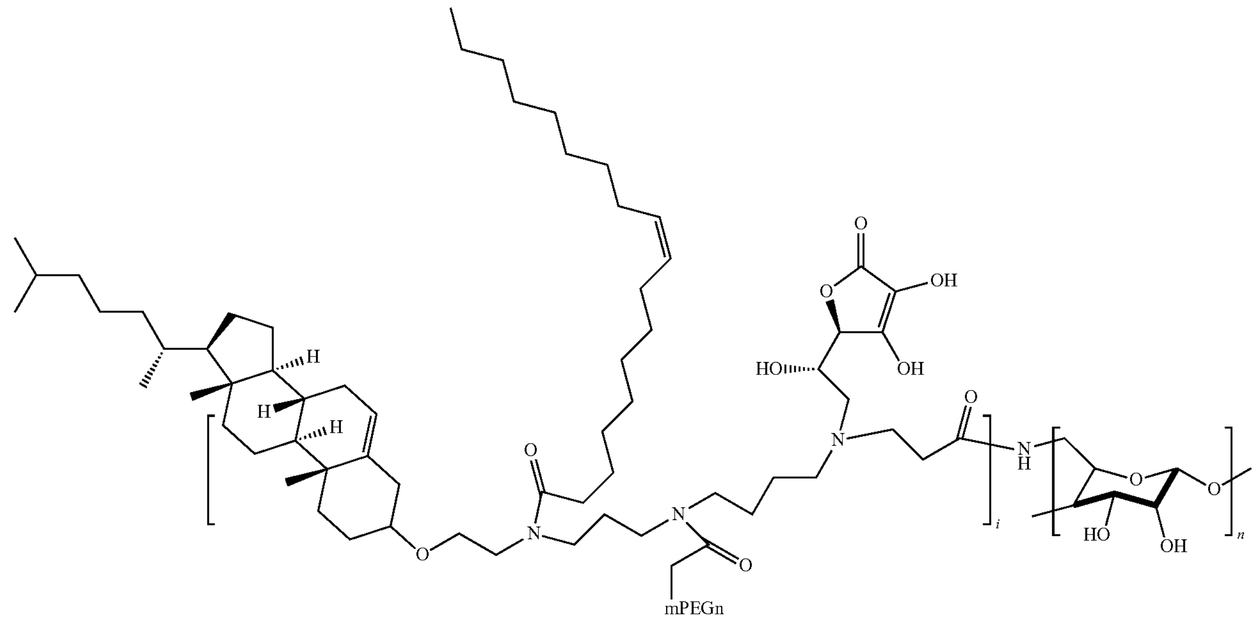 |

In Table 4 the types of coupling reaction between the carriers and the center backbone as well as any chemical modification of cyclodextrin or a carrier or center backbone prior to the conjugation are alkylation including N-alkylation or O-alkylation, esterification, etherification and amidation. For example, a cyclodextrin may be modified with acryloyl chloride then reacted with center backbone, thus two types of reaction may be involved; esterification and N-alkylation (Michael addition). As one of the key intermediates for the preparation of the conjugate, monotosylation of cyclodextrins may be prepared with 1-(p-tosyl)-imidazole as described in the Reaction Scheme 2 [T. Tan, et al (2011). *Protocol Exchange*. doi:10.1038/protex.2011.214].

Reaction Scheme 2. Preparation of mono-6-tosyl-cyclodextrin

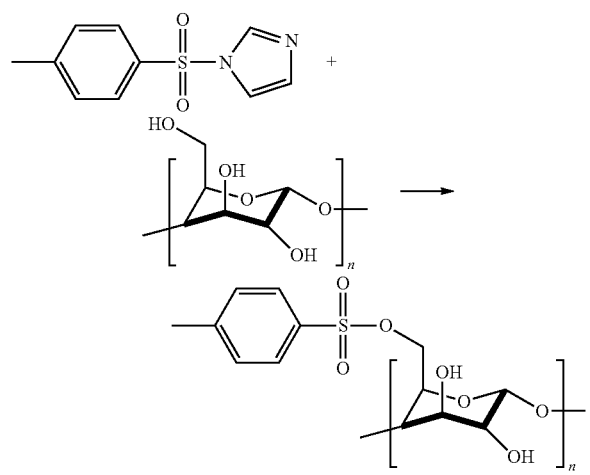

A sample of the CD conjugation with mono-6-tosyl-cyclodextrin is demonstrated in the Reaction scheme 3. The yield product may be further purified with a mixture of methanol and acetonitrile.

Reaction Scheme 3

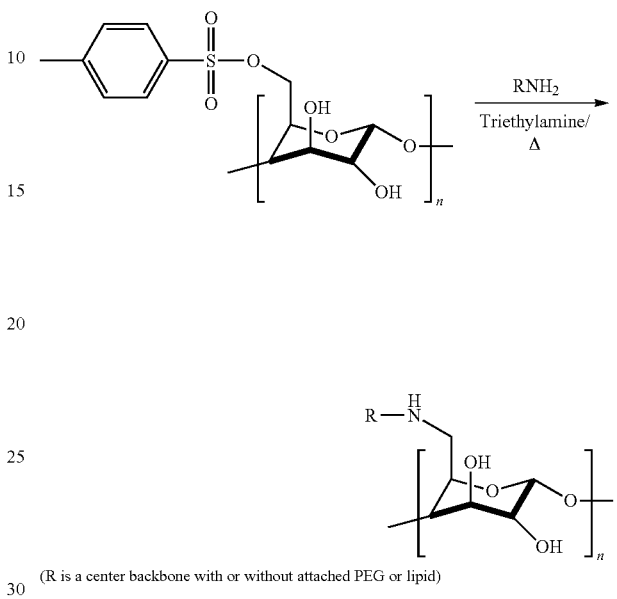

(R is a center backbone with or without attached PEG or lipid)

Converting mono-6-tosyl-CD into mono-6-aminoacryloyl-6-deoxyl-CD may be achieved by the following steps in the Reaction Scheme 4 [W. Zhang, et al (2010). *Applied Surface Science*. 256: 3000-3005].

Reaction Scheme 4. Mono-N-aminoacryloyl-6-deoxylcyclodextrin

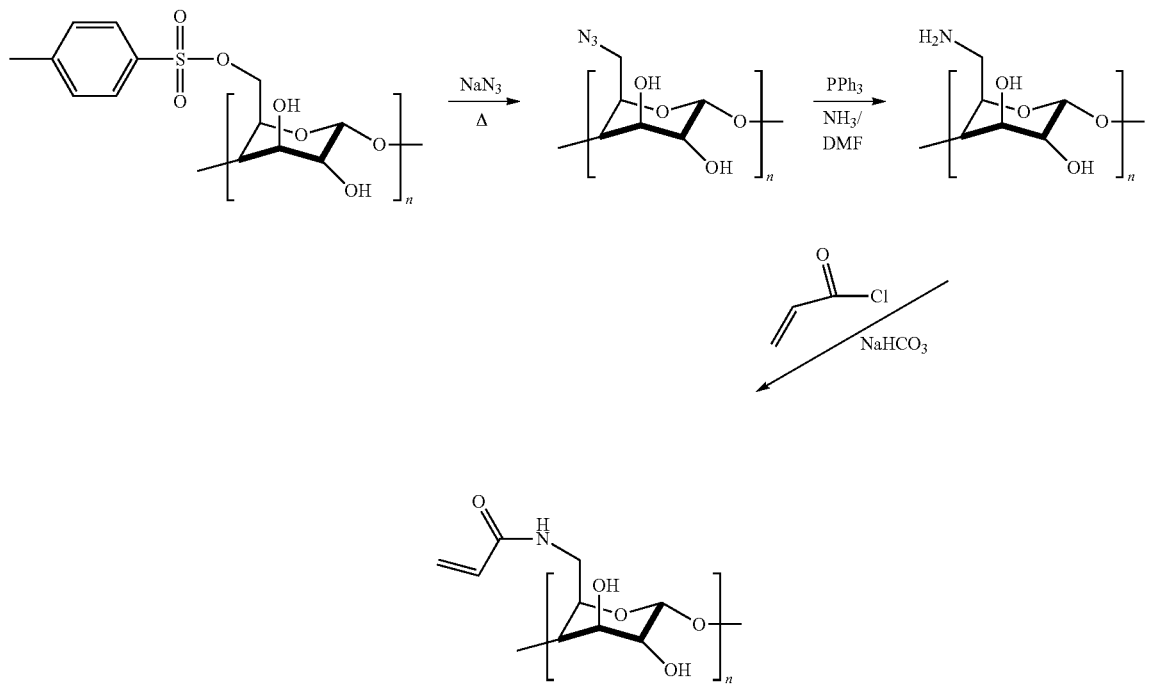

Similar acrylation may be applicable to the PEG or lipid carriers with fewer steps as demonstrated in the Reaction Scheme 5.

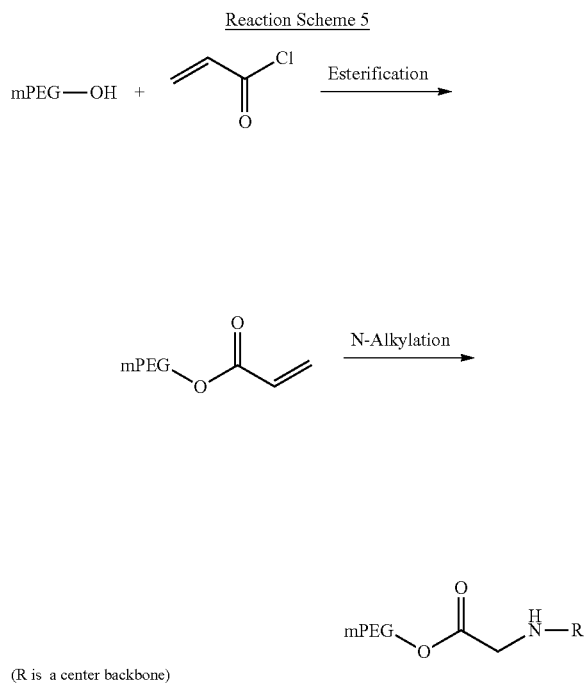

(R is a center backbone)

In one aspect of the present invention, monosubstitution cyclodextrins may be preferable, while a number of modified cyclodextrins are commercially available, for simplicity and cost saving, nature or nonmodified cyclodextrins may be used as for the synthetic starting material since the final products of the polymer-CD-lipid conjugates are enhanced solubilizers, using expensive premodifed or substituted cyclodextrin may not be necessary.

Embodiments of the present invention are described herein in the context of preparation of pharmaceutical compositions including polymer-cyclodextrin-lipid conjugates or polymer-cyclodextrin-lipid conjugates for increasing the solubility and enhancing the delivery of active agents. The approximate preferable compositions for formulated drug products are generally described herein, though different drugs typically have differing optimal formulations.

For IV solutions, the preferable concentration of drug is 0.1% to 30%. More preferable is 0.5 to 10%. Most preferable is 0.5 to 5%. The preferable weight ratio of PEG-cyclodextrin-lipid conjugate (PCL) to the drug (PCL/drug) in the final drug solution for the injection is 1 to 30, w/v (weight/volume). More preferable is 1 (drug) to 25 (PCL). Most preferable is 1 to 10.

It is preferable PEG-cyclodextrin-lipid conjugates having marrow-disperse PEG chains for intravenous administration of pharmaceutical agents. The monodisperse PEG chains may consist of one or more PEG oligomers where the total oligomer purity from individual oligomers may be as high as 80%. For instance, a monodisperse PEG chain may contain 40% of PEG-12 and 40% of PEG-15. It is preferable to have a monodisperse PEG chain containing a few numbers of oligomers. The preferable number of oligomers is 1 to 20, more preferable is 1 to 10. Most preferable is 1 to 5.

For oral solutions, the preferable concentration of drug is 1% to 40%. More preferable is 2.5 to 30%. Most preferable is 5 to 30%. The preferable ratio of PEG-cyclodextrin-lipid conjugates to the drug (PC/drug) is 0.5 to 25, w/v. More preferable is 1 (drug) to 20 (PCL). Most preferable is 1 to 10.

For ophthalmic preparations, the preferable concentration of drug is 0.01 to 5%. More preferable is 0.05 to 2%. Most preferable is 0.1 to 2%. The preferable ratio of PEG-cyclodextrin-lipid to the drug (PCL/drug) is 1 to 30, w/w (weight/weight). More preferable is 3 (drug) to 20 (PCL). Most preferable is 1 to 3.

For topical solutions, the preferable concentration of drug is 0.05 to 5%. More preferable is 0.1 to 5%. Most preferable is 0.1 to 2%. The preferable ratio of PEG-cyclodextrin-lipid conjugates to the drug (PCL/drug) is 1 to 30, w/v. More preferable is 3 (drug) to 20 (PCL). Most preferable is 3 to 10.

For oral capsules, the preferable capsule content of drug is 2 mg to 500 mg. More preferable is 2 mg to 200 mg. Most preferable is 2 mg to 100 mg. The preferable ratio PEG-cyclodextrin-lipid conjugates to the drug (PCL/drug) is 1 to 50, w/w. More preferable is 1 (drug) to 15 (PCL). Most preferable is 1 to 5.

For topical preparations, the preferable concentration of active is 0.5 to 5%, more preferable is 0.5 to 2%, and most preferable is 1 to 2%. The preferable ratio of PEG-cyclodextrin-lipid conjugates to the drug (PCL/drug) is 1 to 30, w/w, more preferable is 1 (drug) to 20 (PCL), most preferable is 3 to 10.

EXAMPLES

Chemicals and Reagents: N, N'-dicyclohexylurea, N, N'-dicyclohexylcarbo-diimide (DCC), oleic acid, ascorbic acid, α-, β-, γ-cyclodextrins, cholecalciferol, cholesteryl choloformate, cholesterol, glucuronic acid, polyethylene glycol (PEG), retinoic acid, α-tocopherol and other chemicals were obtained from Sigma-Aldrich (St. Louis, Mo., USA) or Alfa Aesar (Ward Hill, Mass., USA) or TCI America (Portland, Oreg., USA). Activated PEGs were obtained from Quanta BioDesign (Powell, Ohio, USA) or Thermo Fisher Scientific (Rockford, Ill.) or were provided by LipoSeutics LLC (North Brunswick, N.J., USA).

Example 1. Preparation of tert-Butyl Carbamates (Boc)-Protected Amino Groups

A high yield and effective synthetic method under a catalyst-free and room temperature was reported previously [Chankeshwara, S V and Chakraborti, A K. Org. Lett., (2006); 8, 3259] and used with slightly modification. To a solution of starting compound containing amino benzoate in MeOH, di-t-butyl Bicarbonate was added as one to one molar ratio. The resulting mixture was stirred overnight at room temperature. When the reaction was done, solvent was removed under vacuum; the residue was dissolved into ethyl acetate and washed with saturated $NH_4Cl$ aqueous solution once, then dried over $Na_2SO_4$ and condensed to yield the expected product (>90%). Example of this reaction is demonstrated in Reaction Scheme 4, where R is a main structure of the center backbone. This method gives N-t-Boc derivatives chemoselectively without any side products (such as isocyanate, urea, N,N-di-t-Boc).

Reaction Scheme 4

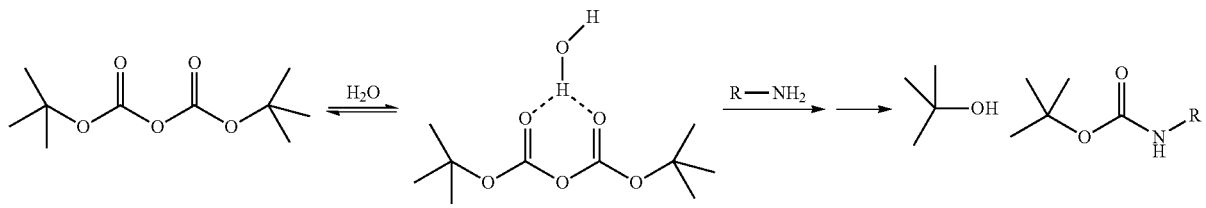

Example 2. Deprotection of Boc-Protected Amino Groups

Effective reagents for the deprotection of tert-butyl carbamates or tert-butyl esters include phosphoric acid and trifluoroacetic acid. The reactions give high yields and very convenient [Li, B. Berliner, M. etc, *J. Org. Chem.*, 2006; 71, 9045]. Equal volumes of trifluoroacetic acid were added to a solution of Boc-carbamate (10% of crude product) in $CH_2Cl_2$. The resulting solution was stirred at room temperature for overnight and the solvent was evaporated and the residue was re-dissolved into $CH_2Cl_2$, then washed with saturated $NaHCO_3$ and dried over $MgSO_4$. Solvent was evaporated and was used in next step without further purification.

Example 3. Preparation of N-Boc-cholesterylserinate 0.03 moles of N-Boc-serine was constantly stirred under nitrogen in 100 mL of chloroform. 0.03 mole of cholesteryl choloformate was dissolved with 100 mL of chloroform and added to this heterogeneous mixture of N-tert-butyloxycarbonylserine and followed by adding 10 mL of anhydrous pyridine. The reaction for 30 minutes under constantly stirring at room temperature, the mixture turned to homogeneous and the reaction was completed when no detectable cholesteryl chloroformate was in the mixture. The bulk solvent was removed under vacuum and the crude product was used to next step without further purification. The resulting product (% of yields 70-80) is showed in Chemical Structure 5.

Chemical Structure 5

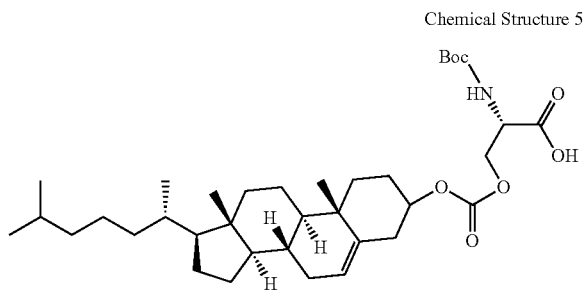

Example 4. Preparation of N-Boc-cholesterylmonomethoxyldodecaethylene glycol ether serinate 0.01 moles of monomethoxyldodecaethylene glycol ether (0.01 mmol) was dissolved with 50 mL of anhydrous $CH_2Cl_2$, 0.01 mole of dicyclohexylcarbodiimide and cholesterylserinate were added. The resulting mixture was stirred at 0° C. for 2 hours, then allowed to warm up to room temperature and stirred for additional 48 hours. When the reaction was complete, the white precipitate was filtered off over celite. The residue was rinsed with small amount of $CH_2Cl_2$ twice and washed with sutured $NH_4Cl$, then dried over $MgSO_4$. Solvent was evaporated to afford pale yellowish oil as showed in Chemical Structure 6. The crude product's purity was determined by $^1H$ NMR and UPLC-MS, ESI-MS (>70%).

Chemical Structure 6

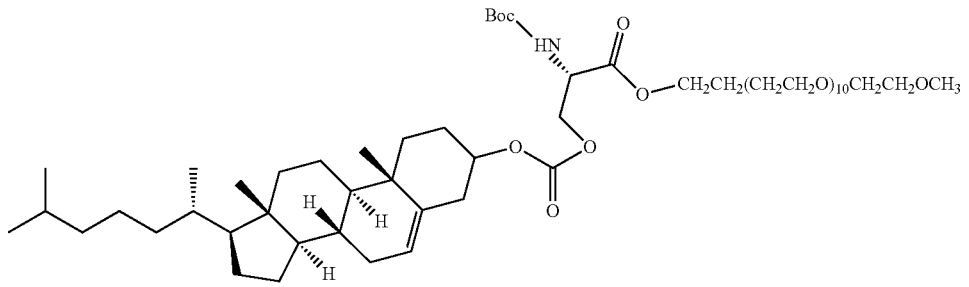

Example 5. Preparation of cholesterylserinylmonomethoxyldodecaethylene-glycol ether-β-cyclodextrin The protection group of tert-butylcarbonyl on the amino group was removed according to the method described in Example 2. 0.01 moles of N-Boc-cholesterylserinylmonomethoxyldodecaethylene glycol ether (0.01 mol) from Example 4 was dissolved with 50 mL of anhydrous tetrahydrofuran (THF), 0.01 mole of Mono-N-aminoacryloyl-6-β-deoxylcyclodextrin and 3% of triethylamine were added. The resulting mixture was stirred at 50-60° C. for overnight, and allowed to cool to the room temperature. The reaction solution was precipitated into isopropyl alcohol (IPA)-Acetonitrile (ACN, 1/4, v/v) and methyl t-butyl ether (MTBE) was added to maximize the isolated yield of precipitate. The crude product was washed with 20/80 (v/v) IPA/ACN and dried under vacuum at 30-40° C. The purity (>95%) of the final product (Chemical Structure 4) was determined by $^1$H NMR and UPLC-MS.

Chemical Structure 7

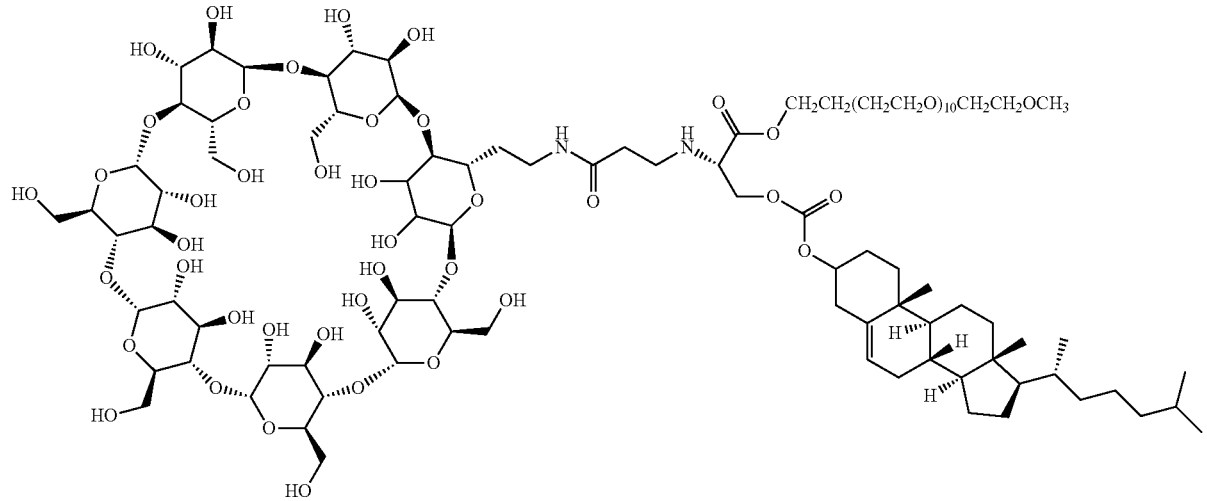

Example 6. Preparation of Cyclodextrindiethylenetriamine

Diethylenetriamine (0.01 mol) was dissolved in 50 mL of dry (molecular sieve) THF and mono-6-tosyl-α-cyclodextrin (0.005 mol) was added. The resulting mixture was stirred for 6 hours at 50-60° C. and allowed to cool to the room temperature when the reaction was completed. The reaction solution was precipitated into IPA and ACN was added to maximize the isolated yield of precipitate. The cake was washed well with 20/80 (v/v) IPA/ACN and dried under vacuum at 30-40° C. The crude product (Chemical Structure 8) and was used in next step without further purification.

Chemical Structure 8

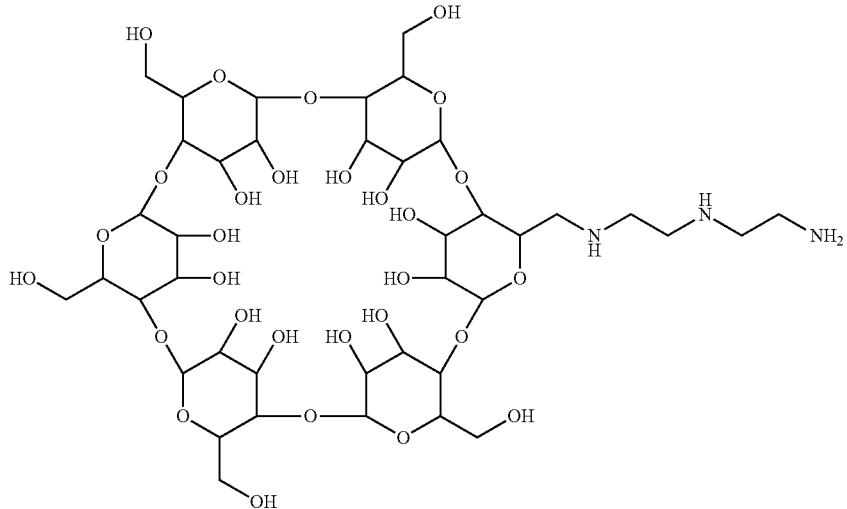

Example 7. Preparation of α-cyclodextrinoleoyldiethylenetriamine-mPEG 0.01 mole of the starting material from Example 6, α-cyclodextrindiethylenetriamine, was dissolved in 20 mL of THF at 20 to 30° C. The slightly excess active oleic acid N-hydroxysuccinimide ester (0.011 mol) was dissolved in 20 mL of tetrahydrofuran (THF), then mixed with α-cyclodextrindiethylenetriamine and adding triethylamine (TEA, 3%, v/v) as a base, stirred for 2 hrs at room temperature. An assay was performed to verify the yield and moves to next step without purification. The active mPEG$_{24}$-NHS (0.01 mol) was dissolved in THF, and then mixed with the above reactants, stirred for overnight at room temperature. After the completion of the reaction, solvents were removed by vacuo and 50 mL of acetone was added to the crude product and filtered and washed with 30 mL of acetone three times. The reaction solution was precipitated into IPA and ACN was added to maximize the isolated yield of precipitate. The crude product was washed well with 20/80 (v/v) IPA/ACN and dried under vacuum at 30-40° C. The purity (>95%) of the final product (Chemical Structure 9) was determined by $^1$H NMR and UPLC-MS.

Example 8. Preparation of α-cyclodextrintriethylenetetramine

Triethylenetetramine (0.02 mol) was dissolved in 50 mL of dry (molecular sieve) THF and mono-6-tosyl-α-cyclodextrin (0.01 mol) was added. The resulting mixture was stirred for 6 hours at 50-60° C. and allowed to cool to the room temperature when the reaction was completed. The reaction solution was precipitated into IPA and ACN was added to maximize the isolated yield of precipitate. The cake was washed well with acetone, then 20/80 (v/v) IPA/ACN and dried under vacuum at 30-40° C. The crude product (Chemical Structure 10) was used in next step without further purification.

Chemical structure 9

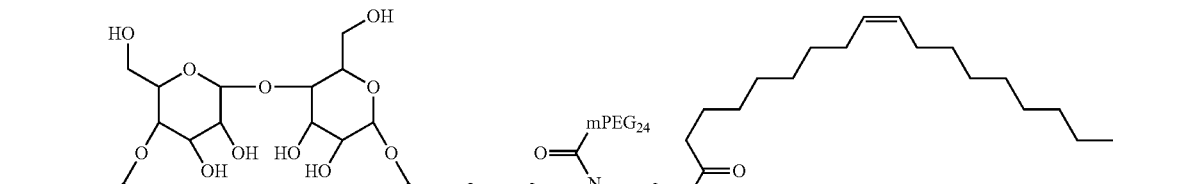

and/or

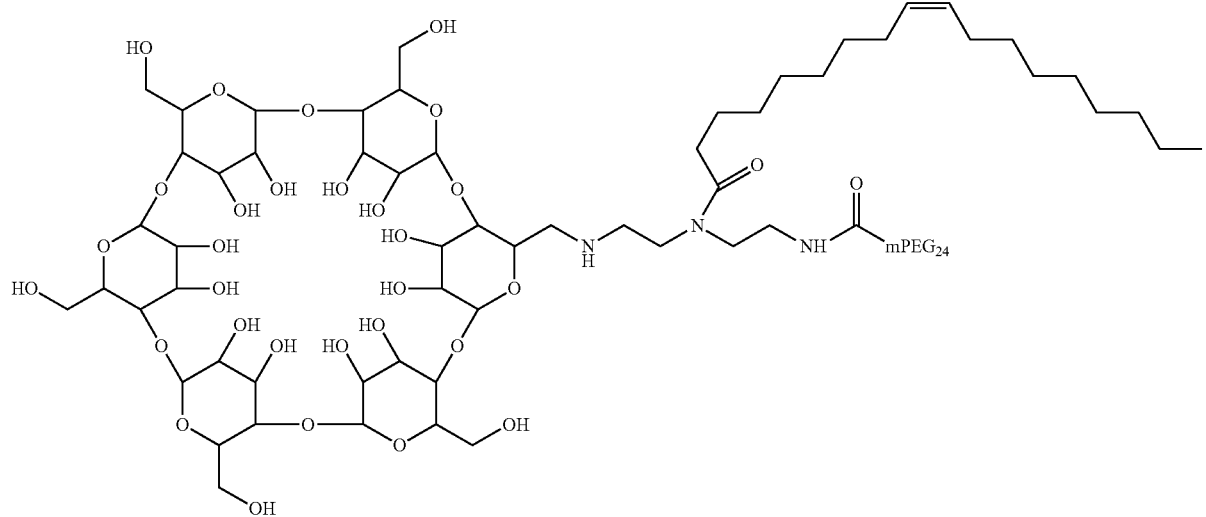

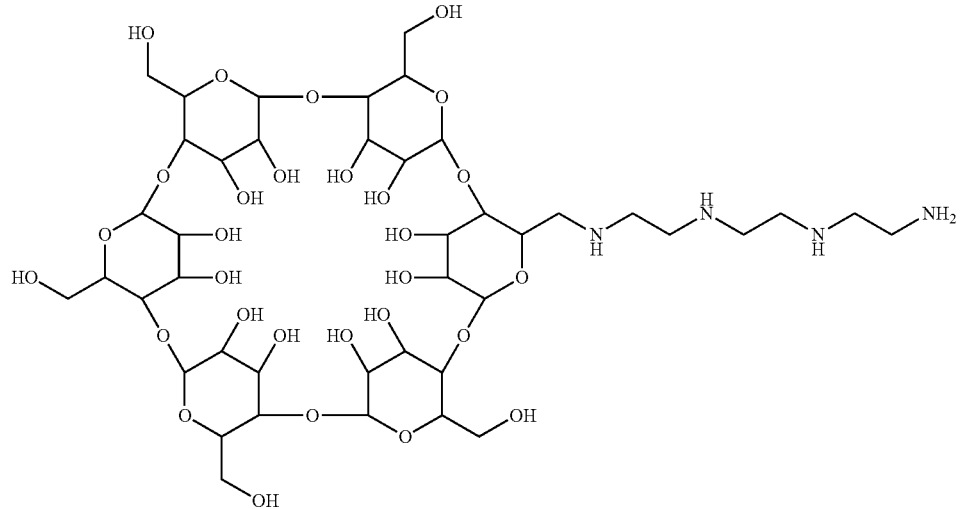

Chemical Structure 10

Example 9. Preparation of α-cyclodextrincholesteryltriethylenetetramine 0.01 mole of α-cyclodextrintriethylenetetramine from Example 8 was dissolved with 50 mL of anhydrous THF, 0.01 mole of cholesteryl chloroformate was added. The resulting mixture was stirred at 45-50° C. for overnight, and allowed to cool to the room temperature. The reaction solution was precipitated into IPA and ACN was added to maximize the isolated yield of precipitate. The crude product was washed well with 20/80 (v/v) IPA/ACN and dried under vacuum at 30-40° C. The purity (>80%) of the final product (Chemical Structure 11) was determined by $^1$H NMR and UPLC-MS.

Chemical Structure 11

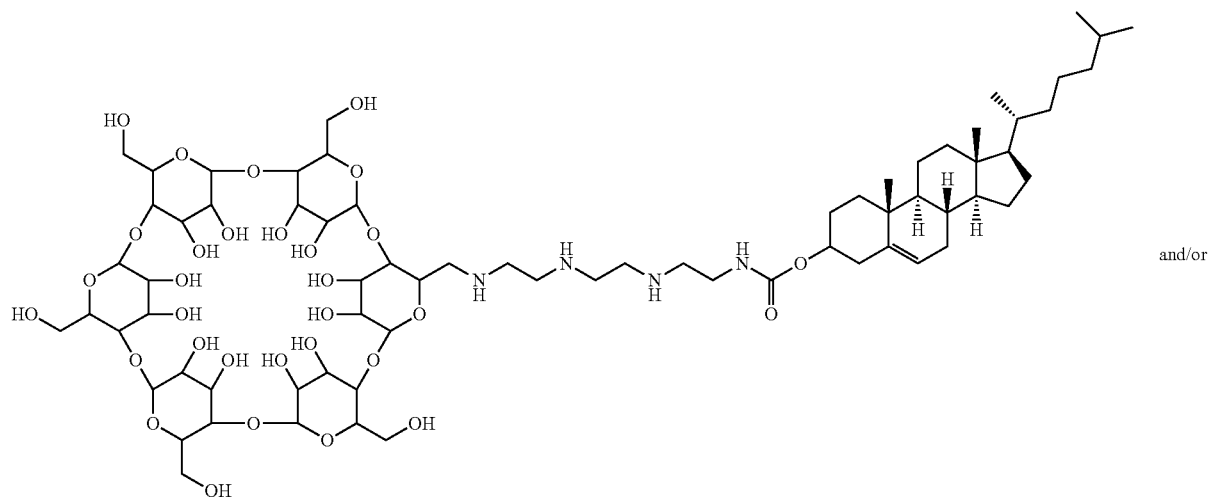

and/or

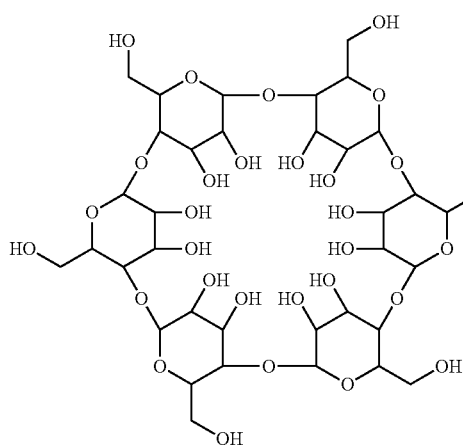

Example 10. Preparation of α-cyclodextrin triethylenetetraminecholesteryl-mPEG 0.01 mole of the starting material from Example 9, α-cyclodextrincholesteryltriethylenetetramine, was dissolved in 20 mL of THF at 20 to 30° C., a slightly excess of the active mPEG$_{24}$-NHS (0.021 mol in 10 mL THF) was added, stirred for overnight at room temperature. 300 mL of acetone was added at the end of the reaction and solvents were removed by vacuo. The crude product washed with acetone and filtered. The wet product (60-65%) was further lyophilized to a wax as showed in Chemical Structure 12.

Chemical Structure 12

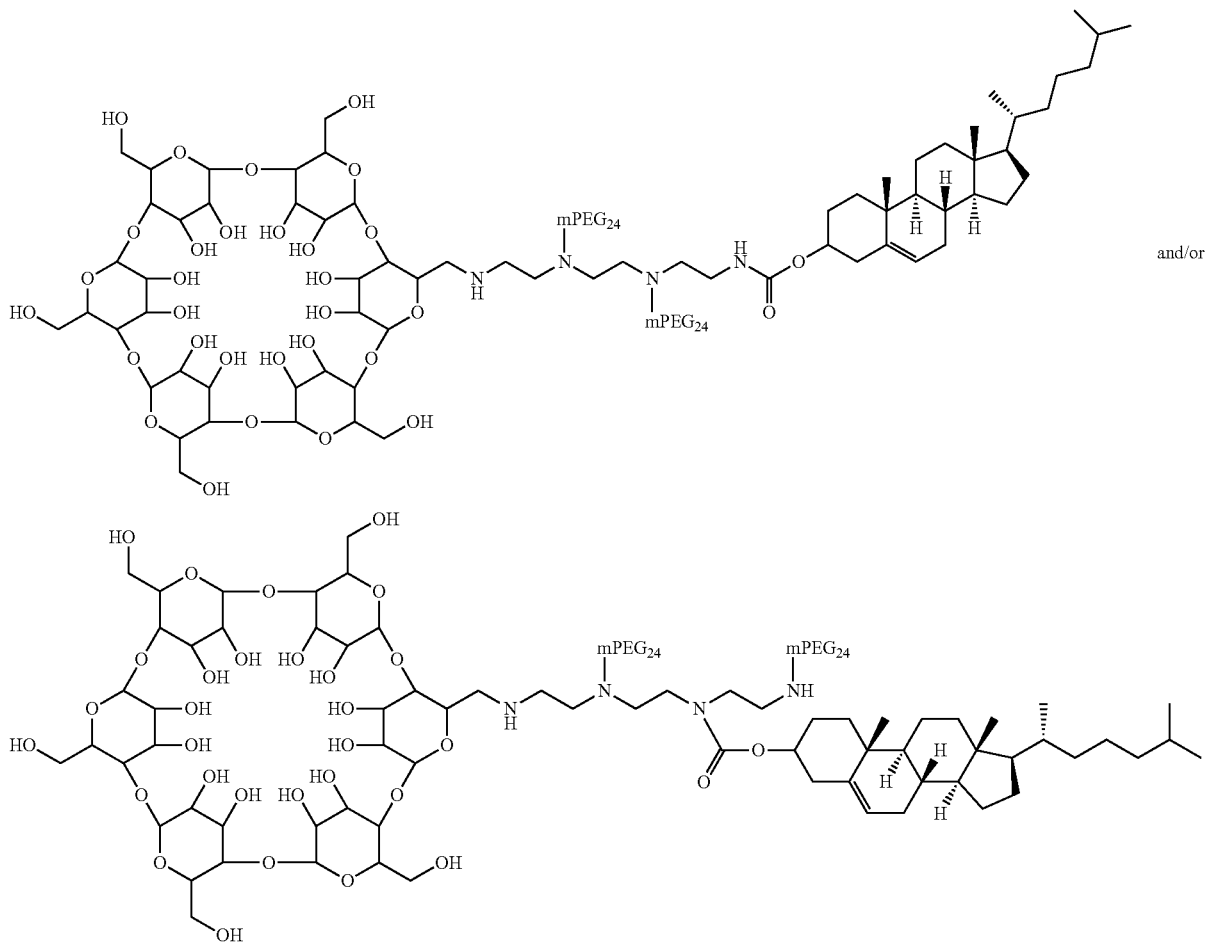

and/or

Example 11. Preparation of cholesterylethylylene glycol ether

Cholesteryl tosylate (0.1 mol) in tetrahydrofuran (100 mL) was mixed with ethylene glycol (1 mol) a round-bottomed flask equipped with a mechanic stirrer and heating mantle. The reaction mixture was stirred under reflux for 12 hours under protection of nitrogen and solvent was removed in vacuo, the residual was redissolved in 200 mL of methylene chloride and washed with 200 mL of water three times. The crude product in methylene chloride was dried in vacuo to yield a solid (90-105%) as showed Chemical Structure 13.

ide solution (100 mL of 5%, w/v) and concentrated by remove tetrahydrofuran under vacuo, then extracted with methylene chloride (50 mL). The aqueous layer was acidified with HCl (36%) to pH 3-4. The aqueous phase was extracted with methylene chloride (25 mL) twice. The combined organic layers were dried over sodium sulfate for 1 hour. The salt was removed by paper filtration and the solvent was removed in vacuo to yield an oil products (45-73%) as showed in Chemical Structure 14.

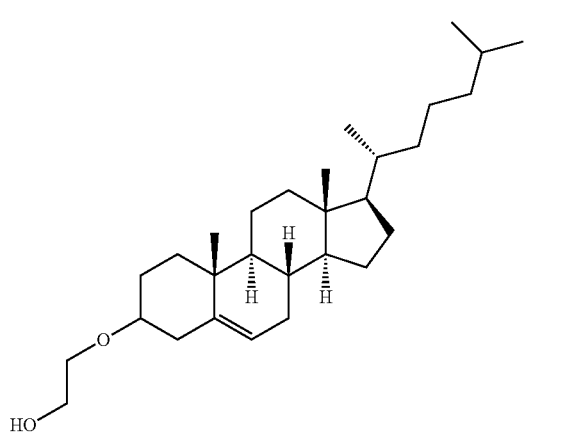

Chemical Structure 13

Chemical Structure 14

Example 12. Preparation of cholesteryl ethylene glycol acetic Acid

Product of cholesteryl ethylene glycol ether from Example 11 (0.02 mol) in tetrahydrofuran (100 mL) was placed into a round-bottomed flask equipped with a mechanic stirrer and a heating mantle. The solution was sparged with nitrogen (50-100 psi). Sodium strip (0.05 g) is added slowly at ambient room temperature. After the addition was completed, the reaction mixture was heated up gradually to 60° C. under constant stirring for 6 hours and sodium chloroacetate (0.03 mol) and NaI (0.005 mol) was added into the reaction flask and the reaction mixture was allowed to continue at 55-60° C. under constant stirring overnight. The reaction was quenched with sodium hydrox-

Example 13. Preparation of γ-Cyclodextrindiaminepropane 1, 3-diaminepropane (0.01 mol) was dissolved in 50 mL of dry (molecular sieve) THF and mono-6-tosyl-γ-cyclodextrin (0.005 mol) was added. The resulting mixture was stirred for 6 hours at 50-60° C. and allowed to cool to the room temperature when the reaction was completed. The reaction solution was precipitated into IPA and ACN was added to maximize the isolated yield of precipitate. The cake was washed well with 20/80 (v/v) IPA/ACN and dried under vacuum at 30-40° C. The crude product (Chemical Structure 15) was used in next step without further purification.

Chemical Structure 15

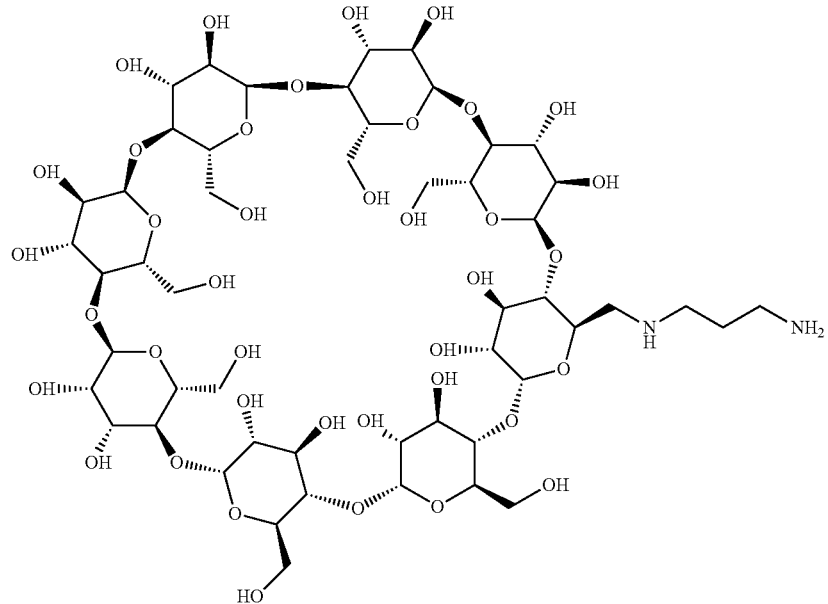

Example 14. Preparation of
γ-Cyclodextrindiaminepropanyl-mPEG 0.01 mole of the starting material from Example 14, γ-Cyclodextrindiaminepropane, was dissolved in 20 mL of THF at 20 to 30° C. The active mPEG$_{24}$-tosylate (0.01 mol) was dissolved in THF, and then mixed with the above reactants, stirred for overnight at room temperature. After the completion of the reaction, solvents were removed by vacuo and 50 mL of acetone was added to the crude product and filtered and washed with 30 mL of acetone three times. The wet product (40-55%) was further lyophilized to a wax as showed in Chemical Structure 16.

Chemical structure 16

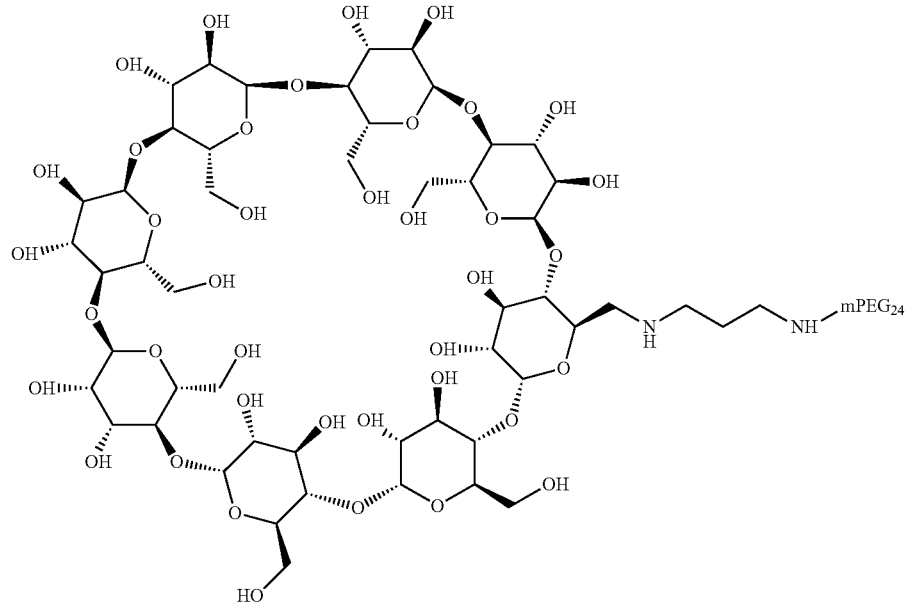

Example 15. Preparation of γ-Cyclodextrincholesteryldiaminepropyl-mPEG 0.01 moles of γ-Cyclodextrindiaminepropanyl-mPEG (0.01 mol) from Example 14 was dissolved with 50 mL of anhydrous N-methyl-2-pyrrolidinone, cholesteryl ethylene glycol acetic acid (0.01 mol) from Example 12 in tetrahydrofuran (50 mL) and slightly excess active N-hydroxysuccinimide ester (0.011 mol) dissolved in 20 mL of tetrahydrofuran (THF) were mixed with of lactobionyldiethylenetriamine-mPEG and adding triethylamine (TEA, 3%, v/v) as a base, stirred for 2 hrs at room temperature. Assays were performed to verify the yield periodically. The resulting mixture was stirred at 45-50° C. for overnight, and allowed to cool to the room temperature. The reaction solution was precipitated into isopropyl alcohol (IPA) and methyl t-butyl ether (MTBE) was added to maximize the isolated yield of precipitate. The crude product was washed well with 50/50 (v/v) IPA/MTBE and dried under vacuum at 30-40° C. The purity (>93%) of the final product (Chemical Structure 17) was determined by $^1$H NMR and UPLC-MS.

Example 16. Preparation of Boc-Glycinylserinate (Boc-Gly-Ser)

Boc-Glycine (0.1 mol) and N,N'-Dicyclohexylcarbodiimide (0.1 mol) in methylene chloride (50 mL) was stirred for 30 minutes, and the mixture was added into a methylene chloride solution (50 mL) of (0.1 mol) slowly. The mixture was stirred for 2 hours. The solution was filtrated and solvent was removed under vacuo to yield a crude product of Boc-Gly-Ser which was transferred to the next step without further purification.

Example 17. Preparation of Cholesterylmesylate (oMsChol)

Mesyl chloride (0.1 mol) was added to a mixture of cholesterol (0.1 mol) and triethylamine (0.1 mol) in methylene chloride (100 mL) placed in an ice-bath. The mixture was stirred for 1 hour and the resulting product was washed with saline and dried over sodium sulfate. The solution was filtered and solvent was removed under vacuo to yield the crude product (oMsChol) which was directly used with Boc-Gly-Ser from Example 16.

Example 18. Preparation of Cholesterylglycinylserinate (Boc-gly-ser-chol)

Potassium tert-butoxide (0.1 mol) was added into a tetrahydrofuran solution (100 mL) of Boc-Gly-Ser and Cholesterol mesylate (0.1 mol) from Example 17. The mixture was stirred for 6 hours at about 65° C. The resulting solution was washed with saline and methylene chloride layer was isolated, dried over sodium sulfate and solvent removed under vacuo to yield an intermediate product of Boc-gly-ser-chol and was used directly without further purification.

Example 19. Preparation of PEG-cholesterylglycinylserinate (Boc-glyserchol-PEG)

Heptaethylene glycol monomethoxyl ether (0.1 mol) and Boc-gly-ser-chol (0.1 mol) from the Example 18 was mixed Chemical structure 17

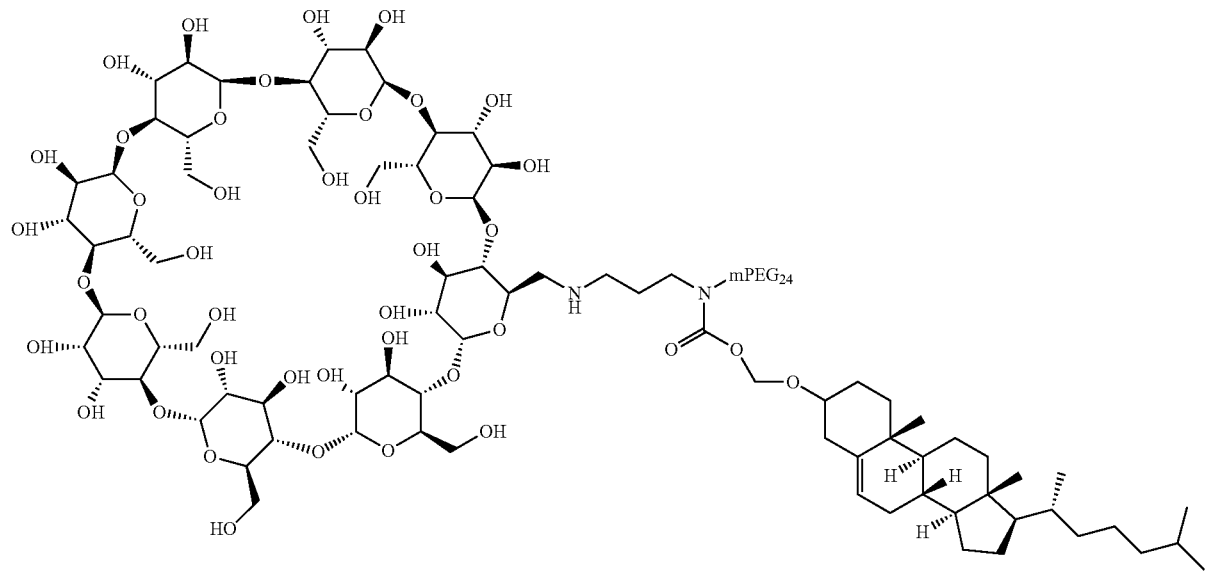

with N,N'-Dicyclohexylcarbodiimide (0.1 mol) in tetrahydrofuran (100 mL). The mixture was kept at ambient room temperature under content stirring for overnight (about 16 hours) and the reaction was checked for completion by TLC or HPLC. The solution was filtered and solvent was removed under reduced vacuo. The crude product was purified using a silica gel column with the eluent of hexanes/ethyl acetate (1:1, v/v). This intermediate product of Boc-glyserchol-PEG$_{17}$ was used for the final synthetic step.

Example 20. Preparation of PEG$_{17}$-cholesterylglycinylserinyl-6-β-cyclodextrin The intermediate product of Boc-Gly-Ser-Chol-PEG$_{17}$ (0.1 mol) from Example 19 was dissolved in methylene chloride (50 mL) and trifluoroacetic acid (1 mol) was added. The mixture was stirred for 2 hours to remove the amino-protecting group. The reaction was quenched by adding saturated sodium bicarbonate solution (~10%) and the organic layer was dried over sodium sulfate and solvent was removed under vacuo. The resulting intermediate of $NH_2$-Gly-Ser-Chol-$PEG_{17}$ was directly transferred to the next step without further purification. $NH_2$-Gly-Ser-Chol-$PEG_{17}$ (0.1 mol) and dried mono-6-aminoacryloyl-6-deoxyl-β-cyclodextrin (0.1 mol) was mixed in TGF (100 mL) and the reaction was initiated by adding triethylamine (3%, v/v). The reaction was reflux in a water bath of 60-65° C. for 16 hours under constant stirring and solvent was removed under vacuo. The resulting waxy crude product was washed with hexanes and dried under vacuo to yield a pale to yellowish solid (80 to 95%) as showed in Chemical Structure 18.

The solid was filtered out and the solution was concentrated under reduced pressure. The crude product was purified by column chromatography with silica gel (eluent: hexanes/ethyl acetate) with a yield of 50% or higher which was used directly for the next step.

Example 23. Preparation of $N^\epsilon$-lysine-$N^\alpha$-cholesterol-mPEG

Trifluoroacetic acid (10 equivalents) was added to the DCM solution of $N^\epsilon$-Boc-lysine-cholesterol-mPEG intermediate (from Example 22) and the mixture was stirred for 2 hours. The mixture was carefully quenched by adding Chemical structure 18

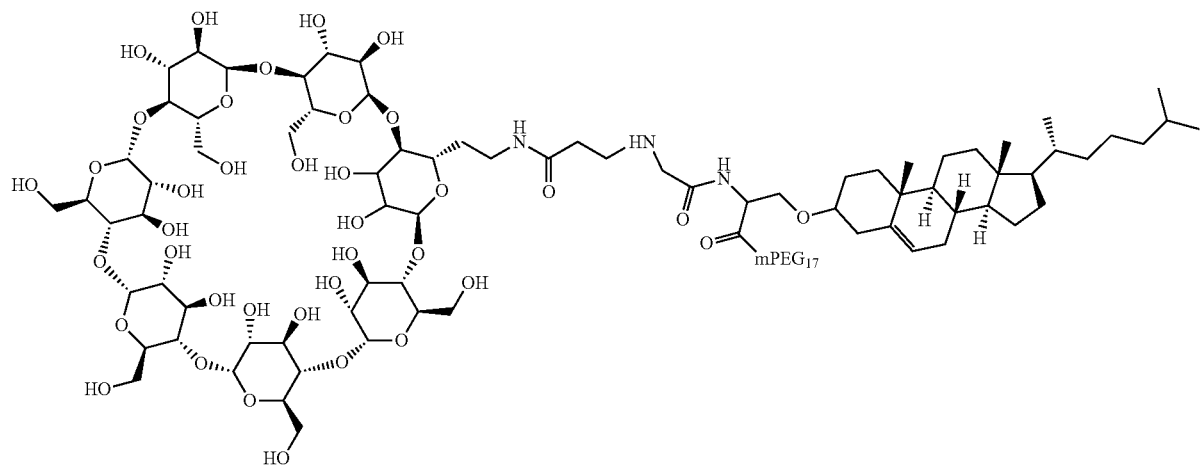

Example 21. Preparation of $N^\epsilon$-tert-butyloxycarbonyl(Boc)-lysine-cholesterol $N^\epsilon$-tert-butyloxycarbonyl(Boc)-lysine (0.2 mol) in 150 mL of methylene chloride was transferred to a round-bottomed flask equipped with a mechanical stirrer. Triethylamine (0.4 mol) is added to the flask and the reaction mixture is cooled down to 0 and 10° C. in an ice-water bath under constant stirring. Cholesteryl chloride (0.18 mol) in 100 mL of methylene chloride was added dropwise. The reaction mixture was allowed to continue under constant stirring for 2 hours after the addition of Cholesteryl chloride was completed. The solution was concentrated to give the crude product of $N^\epsilon$-tert-butyloxycarbonyl(Boc)-$N^\alpha$-cholesterol lysine (yield ~60%), which was used directly for the next step

Example 22. Preparation of $N^\epsilon$-Boc-lysine-cholesterol-mPEG

Equivalent amount of monomethoxyPEG was mixed with $N^\epsilon$-Boc-$N^\alpha$-cholesterol-lysine (from Example 21) in 200 mL THF/DCM (1/1. v/v) and the reaction was started with adding equal amounts of DCC as the catalyst at room temperature under constantly stirring for overnight. The completion of the reaction was monitored by TLC or HPLC.

sodium bicarbonate solution and the organic layer was dried over sodium sulfate and concentrated after removed the salt to quantitatively yield the intermediate $N^\epsilon$-lysine-cholesterol-mPEG, which was used directly at the next step.

Example 24. Preparation $N^\epsilon$-β-cyclodextrin-$N^\alpha$-cholesterol-mPEG-lysinate mono-6-aminoacryloyl-6-deoxyl-β-cyclodextrin was mixed with equal molar quantity of $N^\epsilon$-lysine-$N^\alpha$-cholesterol-mPEG reacted 60-65° C. in THF in the presence of 3% of TEA overnight to obtain $N^\epsilon$-β-cyclodextrin-$N^\alpha$-cholesterol-mPEG-lysinate (Chemical structure 19), The reaction mixture was loaded on a layer of silica gel and air dried. A silica gel column was prepared in a frit filter funnel to give a column volume of about 1 L. The predried reaction mixture was placed on the top of the column and the column was eluted with acetone/hexanes 200 mL of acetone/Isopropyl alcohol (1/5) and 500 mL of 100% acetone. The eluents containing compound was concentrated in vacuo to $N^\epsilon$-β-cyclodextrin-$N^\alpha$-cholesterol-mPEG-lysinate (yield ~80%).

Chemical structure 19

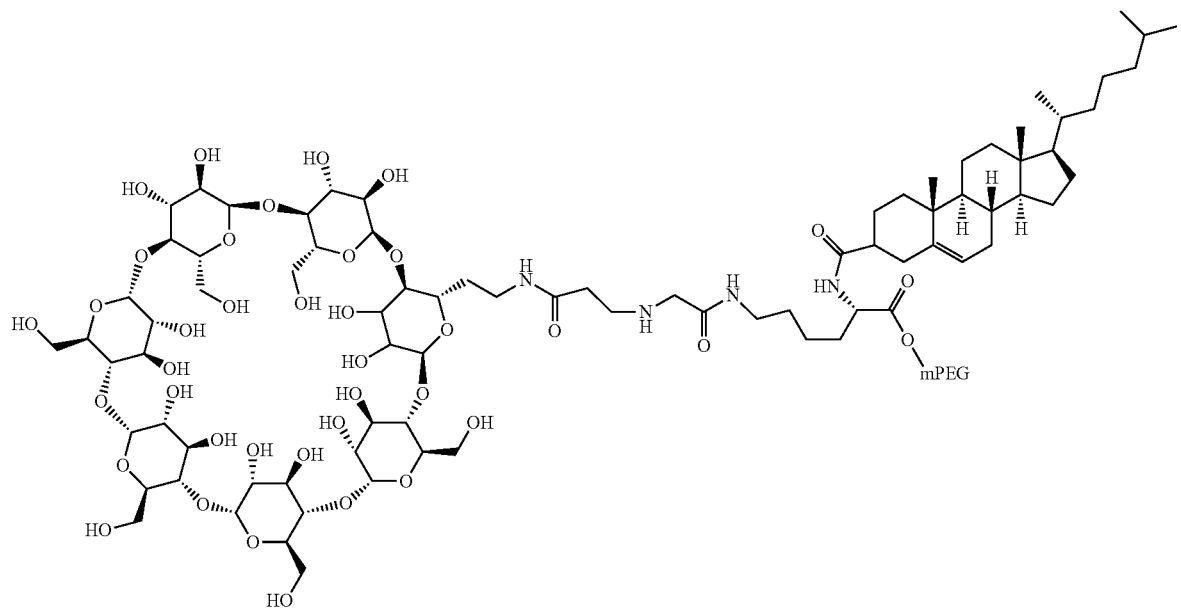

Similar synthetic methods from the Examples 1 to 24 may be utilized for the preparations of other PEG-CD-lipid conjugates; It also further demonstrated that selected molecules may be chemically extended and modified to provide said third or fourth available binding position or site, appropriate molecules include and not limited to aminoalcohols and diamines consisting of ethylenediamine, diaminopropane, ethanolamine, and aminopropanol, aminobutanol, aminopentanol, aminohexanol.

In one aspect of the present invention, while some of these PEG-CD-lipid conjugates showed in Table 4 only monosubstituted PEG-CD-lipid conjugates, due to complexicity of CDs, a mixture of varied substitutions may exist. For quality control and pharmaceutical application, fewer substituent per glucopyranose repeat unit may be preferable. However multiple substituent per glucopyranose may not affect the solubility enhancement or implicate any safety issue since the major advantage with these modified CDs is significant reduction in the quantity of the excipient (solubilizer) used per dose unit as compare to those of non-PEG-lipid modified CDs.

In another aspect, the polymer chain may be replaced by other polymer(s) such as polymethylene glycol or polypropylene glycol or a mixture of the repeating units of methylene glycol, ethylene glycol and propylene glycol. Hydrophilic polymers useful in forming the polymer-carbohydrate conjugates of the invention include polyethylene glycol (PEG) and other polyalkene oxide polymers, polyoxyethylene alkyl ethers, polyvinylpyrrolidone, Poly(allylamine), Poly(l-glycerol methacrylate), Poly(2-ethyl-2-oxazoline), Poly(2-hydroxyethyl methacrylate/-methacrylic acid)/poly (2-hydroxyethyl methacrylate), Poly(2-vinylpyridine), Poly (acrylamide/-acrylic acid), Poly(acrylic acid), Poly(butadiene/maleic acid), Poly(ethyl acrylate/acrylic acid), Poly (ethylene oxide-b-propylene oxide), Poly(ethylene/acrylic acid), Poly(methacrylic acid), Poly(maleic acid), Poly(N-iso-propylacrylamide), Poly(N-vinylpyrrolidone/vinyl acetate), Poly(styrenesulfonic acid), Poly(styrenesulfonic acid/maleic acid), Poly(vinyl acetate), Poly(vinyl phosphoric acid), Poly(vinylamine), Polyacrylamide, Polyacrylic Acid, Polyaniline, Polyethylenimine, Pullulan, Polymethacrylamide. Cop-olymers and block copolymers based on the list above may also be used. The free polymers are water-soluble at room temperature, as well as non-toxic. They do not elicit an appreciable immunogenic response in mammals. Hydrophilic polymers with narrow molecular weight distributions are preferable. Because of already existing acceptance in the pharmaceutical business, PEG is the preferred hydrophilic polymer.

Example 25. Preparation of Pharmaceutical Solutions

A PEG-CD-lipid conjugate solution suitable for drug delivery is prepared as follows. 4% (w/v) of PEG-CD-lipid in Saline was added to a vessel equipped with a mixer propeller and 2% (w/v) of an active pharmaceutical ingredient (API) is pre-dissolved in ethanol (1% of total volume, v/v) and charged into the vessel with constant mixing at ambient room temperature. Mixing is continued until the solution is visually homogeneous. Equal volume of Saline is added to the vessel with adequate mixing. Mixing continued for another 30 minutes or until a homogenous solution is achieved. The finish product is place under vacuum overnight to remove ethanol. A sample formulation is described in Table 5.

TABLE 5

| Ingredient | mg/mL |
|---|---|
| Active pharmaceutical ingredient | 10 |
| PEG-CD-lipid conjugate | 20.0 |
| Sodium Chloride | 9.0 |
| Sodium Hydroxide | See below |
| Hydrochloric Acid | See below |
| Purified Water | qs 1 mL |

The PEG-carbohydrate conjugate may be any of PEG-CD-lipid conjugates described in the invention with a PEG chain consisting of between about 10 and 45 subunits. The API may be etomidate, propofol, alfaxalone, docetaxel, voriconazole, posaconaole, gemcitabine, platins, tacrolimus, cytarabine, ifosfamide, streptozocin, plicamycin, paclitaxel, omeprazole, alprostadil, mitomycin, ziprasidone. nimesulide, sulfomethiazole, lorazepam, griseofulvin, praziquantel, chlorthalidon, exodolac, piroxicam, itraconazole, ibuprofen, praziquantel, praziquantel, omeprazole, digoxin, albendazole, levemopamil HCl, sulfomethiazole, ketoprofen, griseofulvin, itraconazole, carbamazepine zolpidem, phenytoin, rutin, camptothesin, danazol, fluasterone, spiranolactone, rapamycin. Sodium hydroxide is used to prepare a 10% w/w solution in purified water. The targeted pH is in a range of 4.0 to 7.5. Diluted NaOH or HCl may be used to adjust pH if necessary.

Example 26. Solubility Study of Propofol

1% (w/v) of propofol was prepared in a saline based solution with different PEG-carbohydrate conjugates. Table 6 listed the minimum concentration of the conjugates required to solublize propofol as a solubility test reference. While PEG-carbohydrate-lipid conjugates demonstrated a lower molar concentration for solubilizing propofol, much high conjugate concentration was required for hydroxypropyl-β-cyclodextrin and only about 2% of a PEG-CD-lipid was needed. Mixing 2% of cholesterypropanediaminelactobionate-mPEG$_{12}$ and 2-hydroxypropyl-β-cyclodextrin resulted in a milky emulsion (FIG. 2).

TABLE 6

| Conjugate | Concentration (% w/v) |
|---|---|
| 2-hydroxypropyl-β-cyclodextrin | 30 |
| cholesterypropanediaminelactobionate-mPEG$_{12}$ | 3.5 |
| oleoylpropanediaminelactobionate-mPEG$_{12}$ | 3.0 |
| cholesterolpropanediamine-β-cyclodextrin mPEG$_{12}$ | 2.2 |

Example 27. Pharmacokinetic Profile of Voriconazole Formulations

Groups of three male mice (B6D2F1), 4 weeks old and weights of 25 to 32 grams were used for the studies. Pharmacokinetics (PK) were performed on heparinized mouse plasma samples obtained typically at after the bolus IV injection at 5, 15, 45 min and 1, 2, 3, 6, 12 and 24 hours for voriconazole. Samples were analyzed using a HPLC-MS method. To determine the level of the drug, the drug was first isolated from plasma with a sample pre-treatment. Acetonitrile were used to remove proteins in samples. An isocratic HPLC-MS/MS method was then used to separate the drugs from any potential interference. Drug levels were measured by MS detection with a multiple reaction monitoring (MRM) mode. PK data was analyzed using the WinNonlin program (ver. 6.3, Pharsight) noncompartmental models of analysis.

FIG. 3 shows mouse PK profiles of voriconazole formulations with (1) 10 mg/mL voriconazole in a commercial product consisting of 160 mg of sulfobutyl-ether-β-cyclodextrin sodium in saline solution and (2) 10 mg/mL voriconazole in a formulation consisting of 3% of Cholesteryl-propanediamine-monomexyl-PEG$_{15}$-cyclodextrin (CPC-mPEG$_{15}$, see Tables 8 and 9) in saline solution. The drug was administered intravenously and the dosing strength was 10 mg/kg. From the non-compartmental calculations, the AUC of 0 to 24 hours were 49646.6 ng·min/mL with a half-life of 10.7 hours for the commercial voriconazole solution (a) and 50034.2 ng·min/mL with a half-life of 10.6 hours for the voriconazole in CPC-mPEG$_{15}$ solution (b), respectively.

In another aspect, the invention comprises a method of solubilizing a water-insoluble agent, i.e., a drug compound that, because of low solubility in water, typically requires formulation with a pharmaceutically acceptable carrier for effective delivery to an intended site of action. Such delivery may be intravenous, oral, topical, subdermal, sublingual, or any other mode of drug delivery. The invention also includes compositions for such delivery. Both the methods and the compositions related to delivery of water-insoluble agents employ the PEG-CD-lipid conjugates of the present invention and the methods and materials described above.

Example 28. Solubility Study of Voriconazole

1% (w/v) of voriconazole was prepared in a saline based solution with different PEG-lipid conjugates and a modified cyclodextrin. Table 7 listed the minimum concentrations of the conjugates required to solublize voriconazole as a solubility test reference. While it demonstrated that the lowest polymer to drug concentration ratio was N,N,N-oleoylpropanediamine-β-cyclodextrin-mPEG (12) for solubilizating voriconazole, much high concentration of sulfobutyl ether-β-cyclodextrin sodium was required for the same concentration of voriconazole. This is largely due to a relative stronger hydrophobic interactions of when combined an apolar cavity and a hydrophobic core to the solute than those of modified cyclodextrin or PEG-carbohydrate-lipid. The example further demonstrated a significant enhancement in solubilizating hydrophobic compounds with the PEG-lipid modified cyclodextrin, even though sulfobutyl ether-β-cyclodextrin sodium has more negative values of Log P or water soluble, however the solubilizing efficiency of lipophilic agents also depends on the retaining power of the solubilizer.

TABLE 7

| Polymer | LogP | HLB[1] | Solubilizing Voriconazole (w/w) |
|---|---|---|---|
| sulfobutyl ether-β-cyclodextrin sodium | −11.94 | — | 16 |
| N,N,N-oleoyllactobionoyl-mPEG(12)-propanediamine | −1.94 | 16.0 | 12 |
| N,N,N-oleoyl β-cyclodextrin-mPEG(12)-propanediamine | −6.68 | 17.8 | 5 |

[1]Hydrophilic-lipophilic balance

Unlike nature occurring lipids such as phospholipids, the conjugates of the present invention do not have a critical micellar concentration (CMC). Micelles only form when the concentration of surfactants is greater than the CMC, and the temperature of the system is greater than the critical micelle temperature. The present polymer-CD-lipid conjugates may form aggregates spontaneously at any given concentration.

The present invention discloses a novel polymer-CD-lipid conjugate system having at least one of polymer-lipid substituent (through a center backbone structurally) that may be used as a safe and biocompatible vehicle for drug or molecule delivery. A therapeutic, diagnostic or cosmetic agent may be solubilized or encapsulated in those polymer-CD-lipid conjugates to form a solution or micro-suspension.

Another feature or aspect of an embodiment is demonstrated at the time of the filing of this patent application to possibly reside broadly a chemical compound or a method of making a compound wherein the PEG-CD-lipid conjugate is a compound represented by the formulas of the General Structure 1 trough 5.

Generally, the invention includes compositions and methods for synthesizing polymer-CD-lipid conjugates comprising a glycerol backbone or a multiamine or amino acid with a polymer (PEG) chain, a cyclodextrin and a fatty acid or a sterol or a "fat soluble" vitamin or alike group bonded to the backbone. Spacer or linker groups including amino acids may be included between the backbone and the PEG chains, CDs or lipophilic groups. Furthermore, the terminal end of PEG chain may be a charged or polar moiety. For example, in at least one aspect of the present disclosure, a chemical compound carrier for improving the biocompatibility of a therapeutic agent and for increasing the solubility of a hydrophobic or lipophilic agent in water is disclosed. The carrier may comprise a molecular structure represented by the formula:

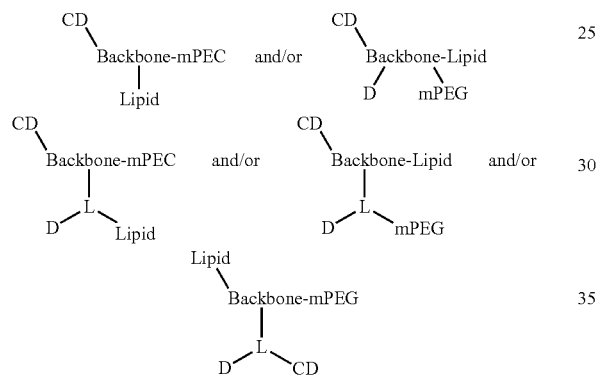

Wherein: Lipid is a lipophilic carrier including steroid acids and fatty acids, sterols and fat soluble vitamins. CD is a cyclodextrin comprises α-, β-. γ-cyclodextrins; PEG is a polymer of polyethylene glycols; D is a secondary fatty acid, sterol or lipophilic vitamin or PEG; Backbone is a molecule having three or four available binding positions and being void of a drug moiety, said Backbone comprising at least one of glycerol, glycerol-like analogues, diamines, triamines, tetramine, diaminoalcohol, aminoalcohols, aminodiol, aminotriols, amino acids, and polyamines; and L is a coupler comprising at least one of glycerol or glycerol-like analogues having three available binding positions, diamines, triamines, diaminoalcohol, aminoalcohols, aminodiols, aminotriols, and amino acids having three available binding positions.

The compounds of the present invention are effective to formulate compositions of active agents, such gemcitabin or platinum drugs, whereby side effects and toxicities associated with therapeutic treatments are reduced.

In the present invention, the permeation enhancement properties of PEG-CD-lipid conjugates may increase the in vivo targeted delivery of drugs, reduce toxicity and improve oral bioavailability of various drugs.

Solutions comprising conjugates of the present invention with solubilized active agents that may incorporate many active agents, including but not limited to propofol, alfaxalone, docetaxel, voriconazole, posaconaole, gemcitabine, platins, tacrolimus, cytarabine, ifosfamide, streptozocin, plicamycin, paclitaxel, omeprazole, alprostadil, mitomycin, ziprasidone. nimesulide, sulfomethiazole, lorazepam, griseofulvin, praziquantel, chlorthalidon, exodolac, piroxicam, itraconazole, ibuprofen, praziquantel, praziquantel, omeprazole, digoxin, albendazole, levemopamil HCl, sulfomethiazole, ketoprofen, griseofulvin, itraconazole, carbamazepine zolpidem, phenytoin, rutin, camptothesin, danazol, fluasterone, spiranolactone, rapamycin.

One feature or aspect of an embodiment is believed at the time of the filing of this patent application to possibly reside broadly in a chemical compound or a method of making a compound represented by the formula:

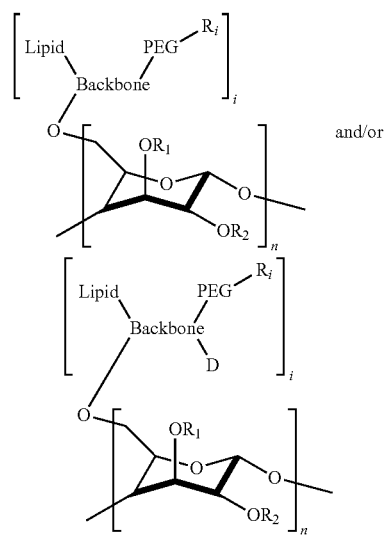

Where the truncated circle is representing repeat units of glucopyranose in cyclodextrin (CD). Lipid is a fatty acid or a sterol or a lipo-vitamin selected from the group including and not limited to saturated and unsaturated fatty acids or cholesterol or sterols, carotenoids, cholecalciferol, retinoids and tocopherols, or alike; mPEG is a polymer and D is a duplication of H, S or P. In presence of cholesterol as the primary lipophilic carrier, the fourth carrier (D) may be a fatty acid or polyunsaturated alcohol or lipid molecule in additional to sterols or lipo-vitamins, preferably the fatty acid is consisting of 5 to 22 carbons. The order of conjugating position for each carrier is not restricted on the center backbone. The linking process between a carrier and the center backbone through alkylation or etherification or esterification or amidation. Wherein "Backbone" comprises glycerol or glycerol-liking having three available binding positions or diamines, triamines, tetramine and polyamines or diaminoalcohol or amino acids having three available binding positions and "Lipid" comprises lauric acid, myristic acid, palmitic acid, oleic acid, stearic acid or cholesterol or sterols having a single hydroxyl group or tocopherols or tocotrienols or cholecalciferol or retinols, retinals, and retinoic acid.

Another feature or aspect of an embodiment is demonstrated at the time of the filing of this patent application to possibly reside broadly in a chemical compound or a method of making a compound wherein a polymer-CD-lipid conjugate with defined carriers is made by a method comprising the steps of:

a. selecting a center backbone void drug moieties with at least three available sites for the conjugations between the three carriers and the center backbone;

b. selecting a polymer as the first career;
c. selecting a terminal group on the polymer carrier
d. selecting a lipid as the second carrier;
e. selecting a cyclodextrin as the third carrier
f. selecting a polymer or lipid as the fourth carrier
g. alternatively selecting a hydrophobic compound other than sterol or lipophilic vitamin as the fourth carrier;
h. selecting a linker or linkers for coupling reactions of alkylation including N-alkylation or O-alkylation or esterification or etherification or amidation between carriers and center backbones.

Yet another feature or aspect of an embodiment is demonstrated at the time of the filing of this patent application to possibly reside broadly in a chemical compound or a method of making a compound where the order of each conjugation step is not restricted and may further comprise the steps of alkylation, etherification, esterification or amidation:
a. protecting the hydroxyl or amino group;
b. bonding the first carrier to the center backbone;
c. bonding the second carrier to the center backbone;
d. removing the hydroxyl or amino protecting group; and
e. bonding the third carrier to the center protecting group.

Still another feature or aspect of an embodiment is demonstrated at the time of the filing of this patent application to possibly reside broadly in a chemical compound or a method of making a compound wherein suitable molecules may be used as the backbone including glycerol or glycerol-like analogues or diamines, triamines or multiamines or aminoalcohols or amino acids or triols or diols with a carboxyl group or amine or diamines with a hydroxyl or carboxyl group and extensible amines or alcohols, wherein the hydrophobic carrier is a sterol or lipophilic vitamin.

Another feature or aspect of an embodiment is demonstrated at the time of the filing of this patent application to possibly reside broadly in a chemical compound or a method of making a compound wherein the polymer is a PEG having subunits between 5 and 115. The PEG chain may consist of between about 5 and 115 subunits. More preferably the PEG chain consists of between about 8 and 115 subunits. Still more preferably the PEG chain consists of between about 8 and 45 subunits.

Yet another feature or aspect of an embodiment is demonstrated at the time of the filing of this patent application to possibly reside broadly in a chemical compound or a method of making a compound where the polymer is a branched PEG having 2 or more subchains each chain having PEG subunits between 5 and 115.

A further feature or aspect of an embodiment is demonstrated at the time of the filing of this patent application to possibly reside broadly in a chemical compound or a method of making a compound having a acyclic carrier group wherein the hydrophobic group is selected from fatty acids including lauric acid, myristic acid, palmitic acid, oleic acid and stearic acids or sterols including cholesterol, stigmasterol, ergosterol, hopanoids, phytosterol, sitosterol, campesterol, brassicasterol, avenasterol adosterol) excluding steroid acids, stanols (saturated steroid alcohols or hydrogenated sterols) or lipophilic vitamins: Vitamin E including and not limited to tocopherols and tocotrienols, Vitamin D including and not limited to cholecalciferol and ergocalciferol, and Vitamin A including and not limited to retinoids, retinol, retinal, retinoic acid, and carotenoids, Another feature or aspect of an embodiment is demonstrated at the time of the filing of this patent application to possibly reside broadly in a chemical compound or a method of making a compound having nonsterol or non "fat-soluble" vitamins as the fourth carrier group wherein the hydrophobic groups may be selected from saturated fatty acids and unsaturated fatty acids or xanthophylls, astaxanthin, auroxanthin, capsanthin, capsorubin, chrysanthemaxanthin, crocetin, crocin, cryptoxanthin, fucoxanthin, kryptoxanthin, lutein, neoxanthin, rubixanthin, violaxanthin, zeaxanthin and polyunsaturated fatty acids or polyunsaturated fatty alcohols including native polyunsaturated alcohols such as farnesol, solanesol and dodecaprenol. It is preferable to have the cholesterol as the primary lipophilic carrier which may reduce or suppress the hemolytic activity of a fatty acid.

Further feature or aspect of an embodiment is demonstrated at the time of the filing of this patent application to possibly reside broadly in a chemical compound or a method of making a compound wherein the CD is a cyclodextrin including α-cyclodextrin, β-cyclodextrin and γ-cyclodextrin.

Yet another feature or aspect of an embodiment is demonstrated at the time of the filing of this patent application to possibly reside broadly in a chemical compound or a method of making a compound wherein the linker is selected from the group consisting of —S—, —O—, —N—, —OCOO—, and to form covalent bonds of ester or ether or amide between carriers and center backbones. While a conjugation reaction of alkylation or etherification or esterification or amidation is preferable with or without adding linker group, the carriers or center backbones may be chemically modified prior to the final coupling reactions. Those of chemical modifications may be carried out with one or more of the linker groups.

Another feature or aspect of an embodiment is demonstrated at the time of the filing of this patent application to possibly reside broadly in a chemical compound or a method of making a compound wherein preferable amino acid linkers are proline, glycine, alanine, lysine, cysteine, valine, isoleucine, leucine, methionine, phenylalanine, histidine, tryptophan, tyrosine, selenocysteine, and arginine.

Another feature or aspect of an embodiment is demonstrated at the time of the filing of this patent application to possibly reside broadly in a chemical compound or a method of making a compound wherein the PEG chain is perfectible monodisperse for intravenous administration of pharmaceutical agents and the monodisperse PEG chain may contain a few numbers of oligomers. The preferable number of oligomers is 1 to 15, more preferable is 3 to 10.

Yet another feature or aspect of an embodiment is demonstrated at the time of the filing of this patent application to possibly reside broadly in a chemical compound or a method of making a compound wherein the PEG chain is perfectible monodisperse for intravenous administration of pharmaceutical agents and the monodisperse PEG chain ranging from 65% to 150% of averaged (or targeted) molecular weights.

Yet another feature or aspect of an embodiment is demonstrated at the time of the filing of this patent application to possibly reside broadly in a chemical compound or a method of making a compound wherein the PEG chains are replaced by polymers selected from the group consisting of polymethylene glycol, polypropylene glycol, and copolymers comprised of a at least two of the monomers selected from the group consisting of methylene glycol, ethylene glycol and propylene glycol.

Still another feature or aspect of an embodiment is demonstrated at the time of the filing of this patent application to possibly reside broadly in a chemical compound or a method of making a compound wherein the terminal (R)

group is preferably easily polarized or negatively or positively charged head-groups such as alkoxy moieties, amines, amino acids, and oligosaccharides.

A further feature or aspect of an embodiment is demonstrated at the time of the filing of this patent application to possibly reside broadly in a chemical compound or a method of making a polymer-CD-lipid conjugate wherein it is used for the composition in delivery of an active agent especially for a poorly water soluble compound of Biopharmaceutics classification II or IV including but not limited to alfaxalone, propofol, docetaxel, paclitaxel, voriconazole and posaconazole.

Another feature or aspect of an embodiment is demonstrated at the time of the filing of this patent application to possibly reside broadly in a method of delivering a compound, the method comprising preparing a polymer-CD-lipid conjugate(s) based formulation of the compound, where the PEG-CD-lipid comprises a PEG, a lipid, a CD and a center backbone selecting from ethylenediamine, diaminopropane, ethanolamine, aminopropanol, aminobutanol, aminopentanol, amino-1-hexanol, the center backbone may be chemically extended and modified to provide said third or a fourth available binding position or site.

Yet another feature or aspect of an embodiment is demonstrated at the time of the filing of this patent application to possibly reside broadly in a method of preparing a pharmaceutical formulation of a therapeutic agent, the method comprising:
a. determining a therapeutic target;
b. determining a mode of administration;
c. determining the physiological conditions the PEG-CD-lipid conjugates based formulation will encounter in reaching the therapeutic target using the mode of administration; and selecting a PEG-CD-lipid conjugate having one or more linkers between the three carriers including one or two PEG chains and one or two hydrophobic carriers (at least one sterol or lipophilic vitamin), a cyclodextrin and a center backbone, where such selecting is informed by the physiological conditions; and combining the PEG-CD-lipid conjugates and the therapeutic agent in a pharmaceutical formulation.

Further feature or aspect of an embodiment is demonstrated at the time of the filing of this patent application to possibly reside broadly on the use of the PEG-CD-lipid conjugates based formulations for the treatment of a disease or a health condition including but not limited to cancer, infection, cardiovascular, central nervous system and inflammation or a treatment of the disease requires organ transplantation or general anesthesia or procedural sedation Another feature or aspect of an embodiment is demonstrated at the time of the filing of this patent application to possibly reside broadly in a chemical compound or a method of making a compound wherein the therapeutic agent is agent is an anesthetic or CNS (central nervous system) agent; and where the weight ratio of the PEG-CD-lipid conjugate to the drug compound is between about 1 and about 20.

Yet another feature or aspect of an embodiment is demonstrated at the time of the filing of this patent application to possibly reside broadly in a chemical compound or a method of making a compound wherein the therapeutic agent is a fungicide or immunosuppressant or antitumor agent or anesthetic agent; and where the weight ratio of the PEG-CD-lipid conjugate to the drug compound is between about 1 and about 30.

One feature or aspect of an illustrative example is believed at the time of the filing of this patent application to possibly reside broadly in a chemical compound carrier for improving the biocompatibility of a therapeutic agent and for increasing the solubility of a hydrophobic or lipophilic agent in water, the carrier comprising a molecular structure represented by the formula:

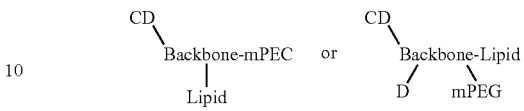

Wherein: Lipid is a lipophilic carrier of fatty acids, sterols, stanols, cholecalciferols, ergocalciferol, retinoids, carotenoids, tocopherols, and tocotrienols; CD is a cyclodextrin comprising α-cyclodextrin. β-cyclodextrin, or γ-cyclodextrin; mPEG is a polymer of polyethylene glycols; D is a duplicate of the Lipid or the mPEG; Backbone is a center Backbone having a molecule with three or four available binding positions or sites and being void of a drug moiety, the backbone comprising at least one of glycerol, glycerol-like analogues having three binding positions, diamines, triamines, tetraamines, polyamines, diaminoalcohols, aminoalcohols, aminodiols, aminotriols, amino acids having three or four available binding positions, triols, tetraols, triacids, tetracids, halogen-containing diols, halogen-containing amines, and carboxyl-containing diols.

Another feature or aspect of an illustrative example is believed at the time of the filing of this patent application to possibly reside broadly in a chemical compound carrier wherein, the Backbone comprises at least three available binding positions or sites for the conjugation of a first carrier, a second carrier, and a third carrier, each the available binding position or site comprising an expendable amino, hydroxyl, acryloyl or carboxylic group; the first carrier having an expendable amino, hydroxyl, acryloyl, or carboxylic group and the Lipid bound thereto; the second carrier comprising having an expendable amino, hydroxyl, acryloyl or carboxylic group and the mPEG bound thereto; the third carrier comprising having an expendable amino, hydroxyl, acryloyl or carboxylic group and the CD bound thereto.

Yet another feature or aspect of an illustrative example is believed at the time of the filing of this patent application to possibly reside broadly in a chemical compound carrier wherein the backbone comprises at least four available binding positions or sites for the conjugation of a first carrier, a second carrier, a third carrier, and a fourth carrier, each the available binding position or site comprising an expendable amino, hydroxyl, acryloyl or carboxylic group.

Still another feature or aspect of an illustrative example is believed at the time of the filing of this patent application to possibly reside broadly in a chemical compound carrier wherein the backbone comprises three available binding positions or sites for the conjugation of a first carrier, a second carrier, and a third carrier, each the available binding position or site comprising an expendable amino, hydroxyl, acryloyl or carboxylic group, wherein: the first carrier has the Lipid bound thereto; the second carrier has the mPEG bound thereto; the mPEG comprising a terminal (R) group; and the third carrier has the CD bound thereto.

A further feature or aspect of an illustrative example is believed at the time of the filing of this patent application to possibly reside broadly in a chemical compound carrier wherein the Backbone is one of a) through d): a) selected from the group consisting of glycerol or glycerol-like analogues, polyamines, diamines, triamines, tetraamines, aminodiols, aminotriols, aminoalcohols, amino acids having three available binding positions or sites, triols, tetraols, erythritol, triacids, tetracid, tetraacetic acid, and tartaric acid; b) selected from the group consisting of ethanediamine, propanediamine, butanediamine, pentanediamine, hexanediamine, diethylenetriamine, diethylenetriamine, bis(3-aminopropyl)-amine, bis(3-aminopropyl)-1,3-propanediamine or N,N'-bis(3-aminopropyl)-1,3-propanediamine, triethylenetetramine, 1,2-bis(3-aminopropylamino)ethane, spermine, tris(2-aminoethyl)amine, spermidine, norspermidine, bis(hexamethylene)triamine, tris(hydroxymethyl)-aminomethane, diaminobenzidine, triazacyclononane, tetraazacyclododecane, threitol, meso-erythritol, dithiothreitol, trimethylcyclohexane-1,3,5-tricarboxylic acid, 1,3,5-cyclohexane-tricarboxylic acid, trimethylbis(hexamethylene)-triamine, arginine, oxylyldiaminopropionic acid having three or four available binding positions or sites, triols, triacids, glucoheptonic acid, and tartaric acid; c) selected from the group consisting of 3-amino-1,2-propanediol, 3-bromo-1,2-propanediol, 3-chloro-1,2-propanediol, 3-fluoro-1,2-propanediol, DL-glyceric acid, diamino-propionic acid, tartaric acid, glucoheptonic acid, 2,4-butanetriol, 2,2-bis(hydroxymethyl)butyric acid, 1,3-diamino-2-propanol and 2-(3-aminopropylamino)ethanol, and 3-((3-aminopropyl)-amino)propanol; and d) selected from the group consisting of aspartic acid, glutamic acid, asparagine, glutamine, lysine, ornithine, serine, and threonine.

Another feature or aspect of an illustrative example is believed at the time of the filing of this patent application to possibly reside broadly in a chemical compound carrier wherein two of the accessible binding positions or sites are selected from the group consisting of aminoalcohols, diamines, ethylenediamine, diaminopropane, ethanolamine, aminopropanol, aminobutanol, aminopentanol, and amino-1-hexanol; and the chemical compound being chemically extended and modified to provide the third or a fourth available binding position or site.

Yet another feature or aspect of an illustrative example is believed at the time of the filing of this patent application to possibly reside broadly in a chemical compound carrier wherein three of the available binding positions or sites of the centercenter Backbone are selected from the group consisting of glycerol or glycerol-like analogues, diamines, triamines, tetramines, polyamines, triols, animoalcohols, triacids, amino acids; and the center Backbone being chemically extended and modified to provide a fourth available binding position or site.

Still another feature or aspect of an illustrative example is believed at the time of the filing of this patent application to possibly reside broadly in a chemical compound carrier wherein the mPEG comprises a single PEG chain having between 5 and 115 subunits or a branched PEG having 2 or more subchains, wherein each the subchain has between 5 and 115 subunits, and a terminal group (R) comprising methoxy, hydroxyl or biotin.

A further feature or aspect of an illustrative example is believed at the time of the filing of this patent application to possibly reside broadly in a chemical compound carrier wherein the Lipid is selected from the group consisting of sterols or stanols; cholesterol, stigmasterol, ergosterol, hopanoids, phytosterol, sitosterol, campesterol, brassicasterol, avenasterol adosterol, fatty soluble vitamins; retinols, retinoids, retinal, retinoic acid, tretinoin, carotenoids, β-carotene, tocopherols, tocotrienols, cholecalciferol, and ergocalciferol.

Another feature or aspect of an illustrative example is believed at the time of the filing of this patent application to possibly reside broadly in a chemical compound carrier wherein the Lipid is selected from the group of a fatty acid having between 5 to 22 carbons.

Yet another feature or aspect of an illustrative example is believed at the time of the filing of this patent application to possibly reside broadly in a chemical compound carrier wherein the center Backbone is selected from the group consisting of glycerol, polyamines, diamines, triamines, tetraamines, aminodiol, aminotriols, aminoalcohols, triols, tetraols, erythritol, triacids, tetracid, tetraacetic acid, glucoheptonic acid, tartaric acid, and amino acids having three available binding positions or sites, the CD is selected from the group consisting of α, β, and γ cyclodextrin having an averaged number of substituent per glucopyranose repeat unit ranging from 0.6 to 3, the Lipid is selected from the group consisting of myristic acid, palmitic acid, stearic acid myristoleic acid, palmitoleic acid, sapienic acid, elaidic acid, vaccenic acid, linoleic acid, tocopherols/tocotrienols, retinoids/carotenoids, cholecalciferol, steroids, and sterols, and the mPEG is mPEG$_n$ with n being the number of ethylene glycol subunit ranging from 5 to 115.

One feature or aspect of an illustrative example is believed at the time of the filing of this patent application to possibly reside broadly in a chemical compound carrier selected from the group consisting of oleoyl-mPEG-(aminopropoxy)acetocyclodextrin, stearoyl-mPEG-(aminopropoxy)acetocyclodextrin, palmitoyl-mPEG-(aminopropoxy)acetocyclodextrin, myristoyl-mPEG-(aminopropoxy)acetocyclodextrin, cholestery-mPEG-(aminopropoxy)-acetocyclodextrin, cholestery-mPEG-(aminopropoxy)acetocyclodextrin, tocopheryl-mPEG-(aminopropoxy)acetocyclodextrin, retinoyl-mPEG-(aminopropoxy)acetocyclodextrin, retinoyl-mPEG-(aminopropoxy)-acetocyclodextrin, cholecalciferol-mPEG (aminopropoxy)acetocyclo-dextrin, oleoylpropane-diaminecyclodextrin-mPEG, N$^ε$-cyclodextrin-N$^α$-oleoyl-mPEG-lysinate, N$^ε$-cyclodextrin-N$^α$-myristoyl-mPEG-lysinate, N$^ε$-cyclodextrin-N$^α$-stearoyl-mPEG-lysinate, stearoylpropanediamine-cyclodextrin-mPEG, oleoyldiethylenetriamine-bismPEG-cyclodextrin, palmitoyldiethyletri-amine-bismonomethoxyl-PEG-ether-cyclodextrin, oleoyltriethylenetetramine-β-cyclodextrin-bismPEG, palmitoyl-propanediamine-cyclodextrin-bismPEG, myristoylpropanediamine-cyclodextrin-mPEG, palmitoyl-propane-diamine-cyclodextrin-mPEG, cholestery-propane-diamine-cyclodextrin-mPEG, N$^ε$-cyclodextrin-N$^α$-cholesterol-mPEG-lysinate, cholesterydiethylenetriamine-cyclodextrin-mPEG, α-tocopheroltriethylenetetramine-bismonomethoxyl-PEG-ether-cyclodextrin, cholestertriethylene-tetramine-bismPEG-cyclodextrin, cholesterytriethylenetetramine-cyclodextrin-bismPEG, cholesterytriethylenetetramine-β-cyclodextrin-mPEG, tocopheryl-propanediamine-cyclodextrin-mPEG, retinoylpropanediamine-cyclodextrin-mPEG, retinoyldiethylenetriamine-cyclodextrin-mPEG, cholecalciferoldiethylenetriamine-cyclodextrin-mPEG, cholecalciferoldiethylenetriamine-bismPEG-cyclodextrin, cyclodextrin-tocopherylethylene-bismPEG-aminosalicylate, cholecalciferoldiethylenetriaminemono-bismPEG-cyclodextrin, cholesterylascorbyldiethylenetriamine-tryptophanyl-mPEG-cyclodextrin, cholesterolascorbyl-mPEG-propanediaminocyclodextrin, cholesterolaspartate-mPEG-cyclodextrin, cholesteryloleoylascorbyl-diethylenetriamine-mPEG-cyclodextrin, cholesterylretinoyldiethylene-triamine-mPEG-cyclodextrin, cholesterolascorbyltriethylenetetramine-bismonomethoxy-PEG-ether-cyclodextrin, cyclodextrin-tocopherol-mPEG-lysinate, cholesteroltriethylenetetramine-bismPEG-cyclodextrin, cholesterololeoyl-cyclodextrin-diethylenetriamine-mPEG, bismPEG-propanediamineserinol-N-cholesterol-N'-cyclodextrin, cyclodextrindiaminopropanolcholesterol-mPEG-ascorbate, cholecalciferolascorbyldiethylene-triamine-cyclodextrin-mPEG, $^\varepsilon$N-cyclodextrin-$^\varepsilon$N-cholesteryl-$^\alpha$N-acetyl-mPEG-lysinate, cholecalciferoldipropylenetriamine-mPEG-cyclodextrin, cholesteryldiethylenetriamine-tryptophanyl-mPEG-cyclodextrin, N-cyclodextrin-cholesterolaspartate-mPEG, cholesteryl-retinoyltriethylenetetramine-mPEG-cyclodextrin, cholesteryltriethylenetetramine-bis-mPEG-cyclodextrin, $^\varepsilon$N-cyclodextrin-$^\varepsilon$N-α-tocopherol-$^\alpha$N-acetylmonomethoxylPEG-ether-lysinate, α-tocopheroltriethylenetetramine-bis-mPEG-cyclodextrin, cholesterolascorboyldiethylenetriamine-mPEG-cyclodextrin, cholecalciferololeoylascorboyldiethylenetriamine-mPEG-cyclodextrin, and cholesteryloleoylascorboyldiethylenetriamine-mPEG-cyclodextrin.

Another feature or aspect of an illustrative example is believed at the time of the filing of this patent application to possibly reside broadly in a method for treating a disease or health condition in a mammal with a chemical compound carrier as disclosed above, the method comprising the steps of: 1) providing an aqueous solution or mixture; 2) adding the chemical compound chemical compound carrier, as described above, as a solubility or bioavailability enhancer to the aqueous solution; and 3) adding a pharmaceutical active ingredient (API) to the aqueous solution forming a prepared composition; and 4) treating the mammal with the prepared composition.

Yet another feature or aspect of an illustrative example is believed at the time of the filing of this patent application to possibly reside broadly in a method for treating a disease or health condition in a mammal with a chemical compound carrier as disclosed above, the method comprising treating cancer.

Still another feature or aspect of an illustrative example is believed at the time of the filing of this patent application to possibly reside broadly in a method for treating a disease or health condition in a mammal with a chemical compound carrier as disclosed above, the method comprising treating an infection or inflammation.

A further feature or aspect of an illustrative example is believed at the time of the filing of this patent application to possibly reside broadly in a method for treating a disease or health condition in a mammal with a chemical compound carrier as disclosed above, the method comprising treating a condition that relates to the cardiovascular or central nervous system.

Another feature or aspect of an illustrative example is believed at the time of the filing of this patent application to possibly reside broadly in a method for treating a disease or health condition in a mammal with a chemical compound carrier as disclosed above, the method comprising treating a condition that comprises organ transplantation.

Yet another feature or aspect of an illustrative example is believed at the time of the filing of this patent application to possibly reside broadly in a method for treating a disease or health condition in a mammal with a chemical compound carrier as disclosed above, the method comprising treating a condition that comprises general anesthesia or procedural sedation.

Another feature or aspect of an embodiment is to differentiate the present invention chemically and physically from the previous patent publications US2012/202,979 and US2012/202,890; in the present invention, a cyclodextrin is incorporated. As demonstrated in Tables 4, such structures increased lipophilic properties was not mentioned or utilized in the previous inventions. For instance, the PEG-CD-fatty acid conjugates, the PEG-CD-cholesterol conjugates and PEG-CD-lipo-vitamin conjugates were demonstrated for the first time.

While preferred embodiments of the present invention have been described, those skilled in the art will recognize that other and further changes and modifications may be made without departing from the spirit of the invention, and all such changes and modifications should be understood to fall within the scope of the invention.

The invention claimed is:

1. A chemical compound having a structure represented by Formula (A) below:

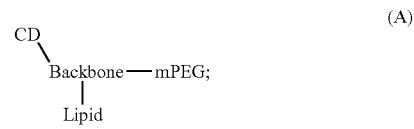

wherein:

Backbone is a molecule to which at least three carrier groups have been covalently bonded and which is not a drug moiety, said Backbone being selected from a group consisting of glycerol, diamines, triamines, tetraamines, polyamines, aminoalcohols, aminodiols, aminotriols, triols, tetraols, and carboxyl-containing diols;

Lipid is a lipophilic carrier group covalently bonded to Backbone, said Lipid being selected from a group consisting of fatty acids, sterols, stanols, cholecalciferols, ergocalciferol, retinoids, carotenoids, tocopherols, and tocotrienols;

CD is a cyclodextrin carrier group covalently bonded to Backbone, said CD being selected from a group consisting of α-cyclodextrin, β-cyclodextrin, and γ-cyclodextrin; and mPEG is a polymeric carrier group covalently bonded to Backbone, said mPEG being a methoxy terminated polyethylene glycol polymer.

2. The chemical compound of claim 1 wherein Lipid, CD and mPEG are each covalently bonded to Backbone via an expendable amino, hydroxyl, acryloyl or carboxylic group on Backbone.

3. The chemical compound of claim 1 wherein said Backbone is ethanediamine, propanediamine, butanediamine, pentanediamine, hexanediamine, diethylenetriamine, diethylenetriamine, bis(3-aminopropyl)-amine, bis(3-aminopropyl)-1,3-propanediamine or N,N'-bis(3-aminopropyl)-1,3-propanediamine, triethylenetetramine, 1,2-bis(3-aminopropylamino)ethane, spermine, tris(2-aminoethyl)amine, spermidine, bis(hexamethylene)triamine, tris(hydroxymethyl)-aminomethane, trimethylbis(hexamethylene)triamine, 3-amino-1,2-propanediol, DL-glyceric acid, diamino-propionic acid, 1,3-diamino-2-propanol and 2-(3-aminopropylamino)ethanol, 3((3-aminopropyl)-amino)propanol lysine, or serine.

4. The chemical compound of claim 1 wherein said mPEG comprises:
   a single PEG chain having between 5 and 115 subunits, or
   a branched PEG having two or more subchains, wherein each of said two or more subchains has between 5 and 115 subunits.

5. The chemical compound of claim 1 wherein said Lipid is selected from the group consisting of cholesterol, stigmasterol, ergosterol, phytosterol, sitosterol, campesterol, brassicasterol, avenasterol adosterol, retinols, retinal, retinoic acid, tretinoin, carotenoids, β-carotene, and ergocalciferol.

6. The chemical compound of claim 1 wherein said Lipid is a fatty acid having 5 to 22 carbons.

7. The chemical compound of claim 1, wherein said Lipid is myristic acid, palmitic acid, oleic acid, stearic acid, myristoleic acid, palmitoleic acid, sapienic acid, elaidic acid, vaccenic acid, linoleic acid, a tocopherol, a tocotrienol, a retinoid, a carotenoid, cholecalciferol, a steroid or a sterol, and said mPEG is mPEG$_n$ with n being a number of ethylene glycol subunits ranging from 5 to 115.

8. The chemical compound of claim 1, wherein said chemical compound is a compound selected from a group consisting of oleoyl-mPEG-(aminopropoxy)acetocyclodextrin, stearoyl-mPEG-(aminopropoxy)acetocyclodextrin, palmitoyl-mPEG-(aminopropoxy)acetocyclodextrin, myristoyl-mPEG-(aminopropoxy)aceto-cyclodextrin, cholestery-mPEG-(aminopropoxy)acetocyclodextrin, cholesterymPEG-(aminopropoxy)acetocyclodextrin, tocopheryl-mPEG-(aminopropoxy)acetocyclodextrin, retinoyl-mPEG-(aminopropoxy)acetocyclodextrin, retinoyl-mPEG-(aminopropoxy)-aceto-cyclodextrin, cholecalciferol-mPEG(aminopropoxy)acetocyclodextrin, oleoylpropanediamine-cyclodextrin-mPEG, N$^\varepsilon$-cyclodextrin-N$^\alpha$-oleoyl-mPEG-lysinate, N$^\varepsilon$-cyclodextrin-N$^\alpha$-myristoyl-mPEG-lysinate, N$^\varepsilon$-cyclodextrin-N$^\alpha$-stearoyl-mPEG-lysinate, stearoylpropanediamine-cyclodextrin-mPEG, oleoyl-diethylenetriamine-bismPEG-cyclodextrin, palmitoyldiethyletriamine-bismonomethoxyl-PEG-ether-cyclodextrin, oleoyltriethylenetetramine-β-cyclodextrin-bismPEG, palmitoylpropane-diamine-cyclodextrin-bismPEG, myristoylpropanediamine-cyclodextrin-mPEG, palmitoylpropane-diamine-cyclodextrin-mPEG, cholesterypropanediamine-cyclodextrin-mPEG, N$^\varepsilon$-cyclodextrin-N$^\alpha$-cholesterol-mPEG-lysinate, cholesterydiethylenetriamine-cyclodextrin-mPEG, α-tocopherol-triethylene-tetramine-bismonomethoxyl-PEG-ether-cyclodextrin, cholestertriethylenetetramine-bismPEG-cyclodextrin, cholesterytriethylenetetramine-cyclodextrin-bismPEG, cholestery-triethylenetetramine-β-cyclodextrin-mPEG, tocopherylpropanediamine-cyclodextrin-mPEG, retinoylpropanediamine-cyclodextrin-mPEG, retinoyldiethylenetriamine-cyclodextrin-mPEG, cholecalciferoldiethylenetriamine-cyclodextrin-mPEG, cholecalciferoldiethylenetriamine-bismPEG-cyclodextrin, cyclodextrintocopherylethylene-bismPEG-aminosalicylate, cholecalci-feroldiethylenetriaminemono-bismPEG-cyclodextrin, cholesterylascorbyldiethylenetriamine-tryptophanyl-mPEG-cyclodextrin, cholesterolascorbyl-mPEG-propanediaminocyclodextrin, cholesterolaspartate-mPEG-cyclodextrin, cholesteryloleoylascorbyl-diethylenetriamine-mPEG-cyclodextrin, cholesteryl-retinoyldiethylenetriamine-mPEG-cyclodextrin, cholesterolascorbyl-triethylenetetramine-bismonomethoxy-PEG-ether-cyclodextrin, cyclodextrin-tocopherol-mPEG-lysinate, cholesteroltriethylenetetramine-bismPEG-cyclodextrin, cholesterololeoyl-cyclodextrin-diethylenetriamine-mPEG, bismPEG-propanediamine-serinol-N-cholesterol-N'-cyclodextrin, cyclodextrindiamino-2-propanolcholesterolmPEG-ascorbate, cholecalciferolascorbyldiethylene-triamine-cyclodextrin-mPEG, EN-cyclodextrin-$^\varepsilon$N-cholesteryl-$^\alpha$N-acetyl-mPEG-lysinate, cholecalciferoldipropylenetriamine-mPEG-cyclodextrin, cholesteryldiethylenetriaminetryptophanyl-mPEG-cyclodextrin, N-cyclodextrin-cholesterolaspartate-mPEG, cholesterylretinoyltriethylene-tetramine-mPEG-cyclodextrin, cholesteryltriethylenetetramine-bis-mPEG cyclodextrin, $^\varepsilon$N-cyclodextrin-$^\varepsilon$N-α-tocopherol-$^\alpha$N-acetyl-monomethoxyl-PEG-ether-lysinate, α-tocopherol-triethylenetetramine-bismPEG-cyclodextrin, cholesterolascorboyldiethylenetriamine-mPEG-cyclodextrin, cholecalciferololeoylascorboyldiethylenetriamine-mPEG-cyclodextrin, and cholesteryloleoylascorboyldiethylenetriamine-mPEG-cyclodextrin.

9. A method for treating a disease or health condition in a mammal with the chemical compound of claim 1, the method comprising the steps of:
   1) providing an aqueous solution or mixture;
   2) adding the chemical compound of claim 1 as a solubility or bioavailability enhancer to the aqueous solution; and
   3) adding a pharmaceutical active ingredient (API) to the aqueous solution forming a prepared composition; and
   4) treating the mammal with the prepared composition.

10. The method of claim 9, wherein the disease or health condition is cancer.

11. The method of claim 9, wherein the disease or health condition is an infection or inflammation.

12. The method of claim 9, wherein the disease or health condition relates to cardiovascular or central nervous system.

13. The method of claim 9, wherein treatment of the disease or health condition comprises an organ transplantation.

14. The method of claim 9, wherein treatment of the disease or health condition comprises general anesthesia or procedural sedation.

15. The chemical compound according to claim 1, wherein a further carrier group D is covalently bonded to Backbone, and wherein D is the same as either the Lipid or the mPEG.

* * * * *